United States Patent
Xue et al.

(10) Patent No.: US 9,067,921 B2
(45) Date of Patent: *Jun. 30, 2015

(54) PIPERAZINYLPIPERIDINE DERIVATIVES AS CHEMOKINE RECEPTOR ANTAGONISTS

(71) Applicant: Incyte Corporation, Wilmington, DE (US)

(72) Inventors: Chu-Biao Xue, Hockessin, DE (US); Ganfeng Cao, Newark, DE (US); Taisheng Huang, Wilmington, DE (US); Lihua Chen, Boothwyn, PA (US); Ke Zhang, Wilmington, DE (US); Anlai Wang, Wilmington, DE (US); David J. Meloni, Bear, DE (US); Rajan Anand, Wilmington, DE (US); Joseph Glenn, Mount Royal, NJ (US); Brian W. Metcalf, Moraga, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,781

(22) Filed: Feb. 10, 2014

(65) Prior Publication Data

US 2014/0155404 A1    Jun. 5, 2014

Related U.S. Application Data

(63) Continuation of application No. 13/564,434, filed on Aug. 1, 2012, now Pat. No. 8,680,104, which is a continuation of application No. 12/422,517, filed on Apr. 13, 2009, now Pat. No. 8,268,826, which is a continuation of application No. 11/104,041, filed on Apr. 12, 2005, now Pat. No. 7,678,798.

(60) Provisional application No. 60/572,221, filed on May 18, 2004, provisional application No. 60/561,697, filed on Apr. 13, 2004.

(51) Int. Cl.

| | |
|---|---|
| A61K 31/497 | (2006.01) |
| C07D 401/14 | (2006.01) |
| A61K 31/496 | (2006.01) |
| A61K 45/06 | (2006.01) |
| C07D 401/06 | (2006.01) |
| C07D 417/14 | (2006.01) |
| C07D 471/04 | (2006.01) |
| A61K 31/502 | (2006.01) |
| A61K 31/506 | (2006.01) |

(52) U.S. Cl.
CPC ............ *C07D 401/14* (2013.01); *A61K 31/496* (2013.01); *A61K 45/06* (2013.01); *C07D 401/06* (2013.01); *C07D 417/14* (2013.01); *C07D 471/04* (2013.01); *A61K 31/502* (2013.01); *A61K 31/506* (2013.01)

(58) Field of Classification Search
CPC ... C07D 401/04; C07D 401/14; A61K 31/496
See application file for complete search history.

(56) References Cited

U.S. PATENT DOCUMENTS

| | | | |
|---|---|---|---|
| 5,510,332 | A | 4/1996 | Kogan et al. |
| 5,935,958 | A | 8/1999 | Kozlowski et al. |
| 6,387,930 | B1 | 5/2002 | Baroudy et al. |
| 6,391,865 | B1 | 5/2002 | Baroudy et al. |
| 6,635,646 | B1 | 10/2003 | Laughlin |
| 6,683,096 | B2 | 1/2004 | Pages Santacana et al. |
| 7,192,973 | B2 | 3/2007 | Tucker |
| 7,307,086 | B2 | 12/2007 | Xue et al. |
| 7,566,718 | B2 * | 7/2009 | Wong et al. .............. 514/253.01 |
| 7,678,798 | B2 | 3/2010 | Xue et al. |
| 8,268,826 | B2 | 9/2012 | Xue et al. |
| 2003/0008877 | A1 | 1/2003 | Miller |
| 2004/0132711 | A1 | 7/2004 | Miller et al. |
| 2004/0138226 | A1 | 7/2004 | Guzi et al. |
| 2004/0235855 | A1 | 11/2004 | Lagu et al. |

(Continued)

FOREIGN PATENT DOCUMENTS

| | | |
|---|---|---|
| WO | WO 95/15973 | 6/1995 |
| WO | WO 96/01644 | 1/1996 |

(Continued)

OTHER PUBLICATIONS

Abdi, et al., Diabetes, vol. 51, Aug. 2002, 2489-2495.
Akahoshi, T., et al., Arthritis Rheum., 36, 762 (1993).
Alam, R., et al., J. Clin. Invest., 89:723 (1992).
Allavena, P., et al., Eur. J. Immunol., 24:3233 (1994).
Aurust, P., et al., Circulation, 97:1136 (1998).
Baggiolini, M., et al., and Adv. Immunol., 55:97-179 (1994).
Billick et al., J. Virol., 78(8):4134 (2004).

(Continued)

*Primary Examiner* — Alexander R Pagano
(74) *Attorney, Agent, or Firm* — Fish & Richardson P.C.

(57) ABSTRACT

The present invention relates to compounds of Formula I:

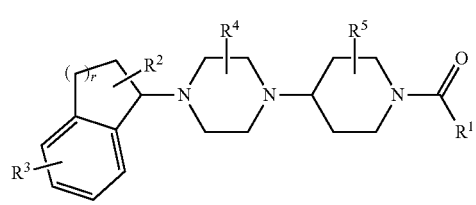

wherein variable substituents are defined herein, that modulate the activity of or bind to chemokine receptors such as CCR5. In some embodiments, the compounds of the invention are selective for CCR5. The compounds can be used, for example, to treat diseases associated with chemokine receptor expression or activity such as inflammatory diseases, immune diseases and viral infections.

7 Claims, No Drawings

(56) References Cited

U.S. PATENT DOCUMENTS

| | | |
|---|---|---|
| 2005/0004121 A1 | 1/2005 | Palani et al. |
| 2005/0192302 A1 | 9/2005 | Xue et al. |
| 2006/0004018 A1 | 1/2006 | Xue et al. |
| 2006/0020133 A1 | 1/2006 | Xue et al. |
| 2006/0105964 A1 | 5/2006 | Ramanathan et al. |
| 2006/0252751 A1 | 11/2006 | Xue et al. |
| 2007/0149532 A1 | 6/2007 | Xue |
| 2008/0108586 A1 | 5/2008 | Friedman et al. |
| 2008/0292589 A1 | 11/2008 | Anilkumar et al. |
| 2012/0295912 A1 | 11/2012 | Xue et al. |

FOREIGN PATENT DOCUMENTS

| | | |
|---|---|---|
| WO | WO 96/06108 | 2/1996 |
| WO | WO 96/20216 | 7/1996 |
| WO | WO 96/31206 | 10/1996 |
| WO | WO 97/16440 | 5/1997 |
| WO | WO 97/16445 | 5/1997 |
| WO | WO 97/22897 | 6/1997 |
| WO | WO 97/30941 | 8/1997 |
| WO | WO 98/00412 | 1/1998 |
| WO | WO 98/02151 | 1/1998 |
| WO | WO 98/53814 | 12/1998 |
| WO | WO 98/53817 | 12/1998 |
| WO | WO 98/54207 | 12/1998 |
| WO | WO 98/58902 | 12/1998 |
| WO | WO 00/05265 | 2/2000 |
| WO | WO 00/66558 | 11/2000 |
| WO | WO 00/66559 | 11/2000 |
| WO | WO 02/079157 | 10/2002 |
| WO | WO 02/079194 | 10/2002 |
| WO | WO 03/020716 | 3/2003 |
| WO | WO 03/061659 | 7/2003 |
| WO | WO 03/066593 | 8/2003 |
| WO | WO 03/084950 | 10/2003 |
| WO | WO 2004/002960 | 1/2004 |
| WO | WO 2004/031172 | 4/2004 |
| WO | WO 2004/033428 | 4/2004 |
| WO | WO 2004/050024 | 6/2004 |
| WO | WO 2004/056364 | 7/2004 |
| WO | WO 2004/056770 | 7/2004 |
| WO | WO 2004/056772 | 7/2004 |
| WO | WO 2004/056799 | 7/2004 |
| WO | WO 2004/056800 | 7/2004 |
| WO | WO 2004/056805 | 7/2004 |
| WO | WO 2004/110451 | 12/2004 |
| WO | WO 2004/113323 | 12/2004 |
| WO | WO 2005/042517 | 5/2005 |
| WO | WO 2006/071875 | 7/2006 |
| WO | WO 2006/071958 | 7/2006 |
| WO | WO 2006/074270 | 7/2006 |
| WO | WO 2006/088836 | 8/2006 |
| WO | WO 2006/088837 | 8/2006 |
| WO | WO 2006/088840 | 8/2006 |
| WO | WO 2006/088919 | 8/2006 |
| WO | WO 2006/088920 | 8/2006 |
| WO | WO 2006/088921 | 8/2006 |
| WO | WO 2006/091428 | 8/2006 |
| WO | WO 2006/091534 | 8/2006 |
| WO | WO 2006/091692 | 8/2006 |
| WO | WO 2007/050375 | 5/2007 |
| WO | WO 2007/100739 | 9/2007 |

OTHER PUBLICATIONS

Bischoff, S. C., et al., J. Exp. Med., 175:1271 (1992).
Boring, L., et al., J. Clin. Invest., 100:2552 (1997).
Boring, L., et al., Nature, 394:894 (1998).
Boyle and Palani, "Structure-Activity Relationship Studies: M2 and CCR5 Receptor Antagonists", Current Topics in Medicinal Chemistry, 3:1155-1169 (2003).
Bridger, et al. J. Med. Chem. 38:366-378 (1995).
Bridger, et al., J. Med. Chem. 42:3971-3981 (1999).
Carr, M. W., et al., Proc. Natl. Acad. Sci. USA, 91:3652 (1994).
Charo, I. F., et al., Proc. Natl. Acad. Sci. USA, 91:2752-2756 (1994).
Cleator et al., The Herpesviridae in, Principles and Practice of Clinical Virology 23-51 (Arie J. Zuckerman et al., eds., 5th ed., 2004).
Combadier, C., et al., The Journal of Biological Chemistry, 270:16491-16494 (1995).
Connor, R. et al, Virology, 206:935-944 (1995).
Conti, P., et al., Allergy and Asthma Proc., 19:121 (1998).
D'Ambrosio et al., J Immunol. Methods, 2003, 273:3-13.
De Clercq et al., Antivir. Chem. Chemother. 12 Suppl. 1:19 (2001).
De Clercq, et al., Antimicrob. Agents Chemother. 38:668-674 (1994).
De Clercq, et al., Proc. Natl. Acad. Sci. 89:5286-5290 (1992).
Dragic et al., Proc. Natl. Acad. Sci. USA, 97(10):5639 (2000).
Gao, J.-L., et al., J. Exp. Med., 185:1959 (1997).
Gerard, C., et al., J. Clin. Invest., 100:2022 (1997).
Gesualdo, L., et al., Kidney Int., 51:155 (1997).
Gillitzer, R., et al., J. Invest. Dermatol., 101:127 (1993).
Gong, J.-H., J. Exp., 4ed., 186:131 (1997).
Gonzalo, J.-A., et al., J. Exp. Med., 188:157 (1998).
Grimm, M. C., et al., J. Leukoc. Biol., 59:804 (1996).
Gu, L., et al., Moll. Cell, 2:275 (1998).
Guzman, L. A., et al., Circulation, 88 (suppl.), I-371 (1993).
Hancock et al., Current Opinion in Immunology, 2000, 12:511-516.
Hancock, et al., J. Exp. Med., vol. 193, #8, Apr. 16, 2001,975-980.
Hayes, I. M., et al., Arterioscler. Thromb. Vasc. Biol., 18:397 (1998).
Hesselgesser et al., J Biol. Chem. 273(25):15687-15692 (1998).
Holmes, W. E., et al., Science, 253:1278-1280 (1991).
Horster, et al., Infection 2006, 34 (2): 110-3.
Horuk, Trends Pharm. Sci., 15:159-165 (1994).
Jiang, Y., et al., J. Immunol., 148:2423-2428 (1992).
Jolicoeur, C., et al., Am. J. Pathol., 152:125-133 (1998).
Journal of Pharmaceutical Science, 66, 2 (1977).
Karina, M., et al., J. Invest. Allergol. Clin. Immunol., 7, 254 (1997).
Karpus, W. J., et al., J. Leukoc. Biol., 62, 681 (1997).
Kazmierski et al., 2003, Bioorg Med Chem., 11:2663-2676.
Kimura, H., et al., Lab. Invest., 78, 571 (1998).
Koch, A. E., et al., J. Clin. Invest., 90, 772 (1992).
Kuna, P., et al., J. Exp. Med., 175, 489 (1992).
Kurihara, T., et al., J. Exp. Med., 186, 1757 (1997).
Kuziel, W. A., et al., Proc. Natl. Acad. Sci., USA, 94, 12053 (1997).
Lahrtz, F., et al., Eur. J. Immunol., 27, 2484 (1997).
Li, et al., J Surg Res. Nov. 2009;157(1):81-90. Epub Feb. 14, 2009.
Lloyd, C. M., et al., J. Exp. Med., 185, 1371 (1997).
Lloyd, C., et al., Curr. Opin. Nephrol. Hypertens., 7, 281 (1998).
Loetscher, P., et al., FASEB J., 8, 1055 (1994).
Loetscher, P., et al., J. Immunol., 156, 322 (1996).
Lu, B., et al., J. Exp. Med., 187, 601 (1998).
Lukacs, N. W., J. Immunol., 158, 4398 (1997).
Luster, New Eng. J Med., 338:436-445 (1998).
MacDermott, R. P., et al., Inflammatory Bowel Diseases, 4, 54 (1998).
Marra, F., et al., Am. J. Pathol., 152, 423 (1998).
Matsushima, K., et al., J. Exp. Med., 169, 1485 (1989).
McManus, C., et al., J. Neuroimmunol., 86, 20 (1998).
Muller et al., Antiviral Strategies in, Antiviral Strategies 1-24 (H.G. Krausslich et al., eds., 2009).
Murphy P. M., et al., Science, 253:1280-1283 (1991).
Murphy, P. M., Annual Review of Immunology, 12:592-633 (1994).
Nelken, N. A., J. Clin. Invest., 88, 1121 (1991).
Neote, K. et al, Cell, 72:415-425 (1993).
Noris, M., et al., Lab. Invest., 73, 804 (1995).
Ogata, H., et al., J. Pathol., 182, 106 (1997).
Oppenheim, J. J. et al., Annu. Rev. Immunol., 9:617-648 (1991).
Oppermann, Cellular Signalling, 2004, 16:1201-1210.
Panzer, et al., Transplantation: Nov. 15, 2004, vol. 78, #9, 1341-1350.
Power, C. A., et al., J. Biol. Chem., 270:19495-19500 (1995).
Proudfoot, Nature Reviews Immunology, 2002, 2:106-116.
Rand, M. L., et al., Am. J. Pathol., 148, 855 (1996).
Ransohoff, R. M., et al., Trends Neurosci., 21, 154 (1998).
Reinecker, H. C., et al., Gastroenterology, 106, 40 (1995).
Remington's Pharmaceutical Sciences, 17:1418, Mack Publishing Company, Easton, Pa., (1985).
Robinson, E., et al., Clin. Exp. Immunol., 101, 398 (1995).

(56) References Cited

OTHER PUBLICATIONS

Roche, E., Bioreversible Carriers in Drug Design, ed. American Pharmaceutical Association and Pergamon Press (1987).
Rollins, B. J., et al., Blood, 78, 1112 (1991).
Rollins, B. J., et al., Proc. Natl. Acad. Sci. USA, 85, 3738 (1988).
Rollins, Blood, New Eng. J Med., 90:909-928 (1997).
Rovin, B. H., et al., Am. J. Kidney. Dis., 31, 1065 (1998).
Saitoh, A., et al., J. Clin. Lab. Anal., 12, 1 (1998).
Salkowski, C. A.; et al., Infect. Immun., 66, 3569 (1998).
Samson, M., et al., Biochemistry, 35:3362-3367 (1996).
Schall and Bacon, Curr. Opin. Immunol., 6:865-873 (1994).
Schimmer, R. C., et al., J. Immunol., 160, 1466 (1998).
Schnickel, et al., Transplantation Proceedings, 38, 3221-3224 (2006).
Schrier, D. J., J. Leukoc. Biol., 63, 359 (1998).
Seino, Y., et al., Cytokine, 7, 301 (1995).
Shin, N. et al. "INCB9471 is a Non-Competitive Small Molecule Antagonist of CCR5" Poster No. 751, 47th Annual Interscience Conference on Antimicrobial Agents and Chemotherapy, Chicago, Ill., Sep. 2007.
Solomon, K. et al. "INCB9471 is a Potent Inhibitor of R5-HIV-1 Infection In Vitro" Poster No. 818, 47th Annual Interscience Conference on Antimicrobial Agents and Chemotherapy, Chicago, Ill., Sep. 2007.
Sousa, A. R., et al., Am. J. Respir. Cell Mol. Biol., 10, 142 (1994).
Starr-Spires et al., Clin. Lab. Med., 22(3):681 (2002).
Stephene, T. H., Am. J. Respir. Crit. Care Med., 156, 1377 (1997).
Strizki et al, Proc. Natl. Acad. Sci. USA, 98(22):12718 (2001).
Sugiyama, Y., et al., Internal Medicine, 36, 856 (1997).
Supplementary European Search Report for Application No. EP 05 75 5295, dated Feb. 19, 2009.
T. Higuchi and V. Stella, "Pro-drugs as Novel Delivery Systems," vol. 14 of the A.C.S. Symposium Series.
T.W. Green and P.G.M. Wuts, Protective Groups in Organic Synthesis, 3rd. Ed., Wiley & Sons, Inc., New York (1999).
Takeya, M.. et al., Hum. Pathol., 24, 534 (1993).
Tremblay et al., Antimicrobial Agents and Chemotherapy, 46(5):1336 (2002).
Troy, S. et al. "Effect of Ritonavir on the Pharmacokinetics of INCB9471, a Potent Antagonist of CCR5 Co-Receptor" Poster No. H-1035, 47th Annual Interscience Conference on Antimicrobial Agents and Chemotherapy, Chicago, Ill., Sep. 2007.
Troy, S. et al. "Single and Multiple Dose Pharmacokinetics of INCB9471, a Potent Antagonist of CCR5 Co-Receptor" Poster No. H-1034, 47th Annual Interscience Conference on Antimicrobial Agents and Chemotherapy, Chicago, Ill., Sep. 2007.
Vaddi, K., et al., J. Immunol., 153, 4721 (1994).
Valente, A. J., et al., Biochemistry, 27, 4162 (1988).
Viola, Annual Rev. Pharma Toxicol., 2008, 48:171-197.
Wada, T., at al., Kidney Int., 49, 761 (1996).
Wada, T., et al., FASEB J., 10, 1418 (1996).
Westby et al., "CCR5 antagonists: host-targeted antivirals for the treatment of HIV infection", Antiviral Chemistry & Chemotherapy vol. 16:339-54 (2005).
Wong, M.; et al., J. Rheumatol., 24,1179 (1997).
Xue et al., "Discovery of INCB9471, a Potent, Selective, and Orally Bioavailable CCR5 Antagonist with Potent Anti-HIV-1 Activity", ACS Med. Chem. Lett. 1:483-487 (2010).
Yamagami, S., et al., Biochem. Biophys. Res. Commun., 202:1156-1162 (1994).
Yla-Herttuala, S., et al., Proc. Natl. Acad. Sci. USA, 88, 5252 (1991).
Yokoyama, H., et al., J. Leukoc. Biol., 1998, 63, 493.
Yoshimura, T., et al., J. Immunol., 142, 1956 (1989).
Yun et al., Circulation, 2004, 109:932-937.
Zeyneloglu, H. B., et al., Am. J. Obstet. Gynecol., 179, 438 (1998).
Zeyneloglu, H. B., et al., Human Reproduction, 13, 1194 (1998).

* cited by examiner

PIPERAZINYLPIPERIDINE DERIVATIVES AS CHEMOKINE RECEPTOR ANTAGONISTS

CROSS REFERENCE TO RELATED APPLICATIONS

This application is a continuation of and claims the benefit of priority under 35 U.S.C. §120 to U.S. application Ser. No. 13/564,434, filed Aug. 1, 2012, which is a continuation of U.S. application Ser. No. 12/422,517, filed Apr. 13, 2009, which is a continuation of U.S. application Ser. No. 11/104,041, filed Apr. 12, 2005. U.S. application Ser. No. 11/104,041 claims priority to U.S. Provisional Application Ser. No. 60/572,221, filed May 18, 2004 and to U.S. Provisional Application Ser. No. 60/561,697, filed Apr. 13, 2004. The disclosures of all of which are incorporated herein by reference in their entirety.

FIELD OF THE INVENTION

The present invention relates to compounds that modulate the activity of or bind to chemokine receptors such as CCR5. In some embodiments, the compounds are selective for CCR5. The compounds can be used, for example, to treat diseases associated with chemokine receptor expression or activity such as inflammatory diseases, immune diseases and viral infections.

BACKGROUND OF THE INVENTION

The migration and transport of leukocytes from blood vessels into diseased tissues is involved in the initiation of normal disease-fighting inflammatory responses. The process, also known as leukocyte recruitment, is also related to the onset and progression of life-threatening inflammatory, as well as debilitating autoimmune diseases. The resulting pathology of these diseases derives from the attack of the body's immune system defenses on normal tissues. Accordingly, preventing and blocking leukocyte recruitment to target tissues in inflammatory and autoimmune disease would be a highly effective approach to therapeutic intervention.

The different classes of leukocyte cells that are involved in cellular immune responses include monocytes, lymphocytes, neutrophils, eosinophils and basophils. In most cases, lymphocytes are the leukocyte class that initiates, coordinates, and maintains chronic inflammatory responses, and blockage of these cells from entering inflammatory sites is desirable. Lymphocytes attract monocytes to the tissue sites, which, collectively with lymphocytes, are responsible for most of the actual tissue damage that occurs in inflammatory disease. Infiltration of the lymphocytes and/or monocytes is known to lead to a wide range of chronic, autoimmune diseases, and also organ transplant rejection. These diseases include, but are not limited to, rheumatoid arthritis, chronic contact dermatitis, inflammatory bowel disease, lupus, systemic lupus erythematosus, multiple sclerosis, atherosclerosis, psoriasis, sarcoidosis, idiopathic pulmonary fibrosis, dermatomyositis, skin pemphigoid and related diseases, (e.g., *Pemphigus vulgaris, P. foliacious, P. erythematosis*), glomerulonephritides, vasculitides, hepatitis, diabetes, allograft rejection, and graft-versus-host disease.

The process by which leukocytes leave the bloodstream, accumulate at inflammatory sites, and start disease is believed to have at least three steps which have been described as (1) rolling, (2) activation/firm adhesion and (3) transendothelial migration [Springer, T. A., Nature 346:425-433 (1990); Lawrence and Springer, Cell 65:859-873 (1991); Butcher, E. C., Cell 67:1033-1036 (1991)]. The second step is mediated at the molecular level by chemoattractant receptors. Chemoattractant receptors on the surface of leukocytes then bind chemoattractant cytokines which are secreted by cells at the site of damage or infection. Receptor binding activates leukocytes increases the adhesiveness of the adhesion molecules that mediate transendothelial migration and promotes directed migration of the cells toward the source of the chemoattractant cytokine.

Chemotactic cytokines (leukocyte chemoattractant/activating factors) also known as chemokines, also known as intercrines and SIS cytokines are a group of inflammatory/immunomodulatory polypeptide factors of molecular weight 6-15 kDa that are released by a wide variety of cells such as macrophages, monocytes, eosinophils, neutrophiles, fibroblasts, vascular endothelial cells, smooth muscle cells, and mast cells, at inflammatory sites (reviewed in Luster, New Eng. J. Med., 338, 436-445 (1998) and Rollins, Blood, 90, 909-928 (1997)). Also, chemokines have been described in Oppenheim, J. J. et al., Annu. Rev. Immunol., 9:617-648 (1991); Schall and Bacon, Curr. Opin. Immunol., 6:865-873 (1994); Baggiolini, M., et al., and Adv. Immunol., 55:97-179 (1994). Chemokines have the ability to stimulate directed cell migration, a process known as chemotaxis. Each chemokine contains four cysteine residues (C) and two internal disulfide bonds. Chemokines can be grouped into two subfamilies, based on whether the two amino terminal cysteine residues are immediately adjacent (CC family) or separated by one amino acid (CXC family). These differences correlate with the organization of the two subfamilies into separate gene clusters. Within each gene cluster, the chemokines typically show sequence similarities between 25 to 60%. The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

MCP-1 (also known as MCAF (abbreviation for macrophage chemotactic and activating factor) or JE) is a CC chemokine produced by monocytes/macrophages, smooth muscle cells, fibroblasts, and vascular endothelial cells and causes cell migration and cell adhesion of monocytes (see for example Valente, A. J., et al., Biochemistry, 1988, 27, 4162; Matsushima, K., et al., J. Exp. Med., 1989, 169, 1485; Yoshimura, T., et al., J. Immunol., 1989, 142, 1956; Rollins, B. J., et al., Proc. Natl. Acad. Sci. USA, 1988, 85, 3738; Rollins, B. J., et al., Blood, 1991, 78, 1112; Jiang, Y., et al., J. Immunol., 1992, 148, 2423; Vaddi, K., et al., J. Immunol., 1994, 153, 4721), memory T lymphocytes (see for example Carr, M. W., et al., Proc. Natl. Acad. Sci. USA, 1994, 91, 3652), T lymphocytes (see for example Loetscher, P., et al., FASEB J., 1994, 8, 1055) and natural killer cells (see for example Loetscher, P., et al., J. Immunol., 1996, 156, 322; Allavena, P., et al., Eur. J. Immunol., 1994, 24, 3233), as well as mediating histamine release by basophils (see for example Alam, R., et al., J. Clin. Invest., 1992, 89, 723; Bischoff, S. C., et al., J. Exp. Med., 1992, 175, 1271; Kuna, P., et al., J. Exp. Med., 1992, 175, 489). In addition, high expression of MCP-1 has been reported in diseases where accumulation of monocyte/macrophage and/or T cells is thought to be important in the initiation or progression of diseases, such as atherosclerosis (see for example Hayes, I. M., et al., Arterioscler. Thromb. Vasc. Biol., 1998, 18, 397; Takeya, M. et al., Hum. Pathol., 1993, 24, 534; Yla-Herttuala, S., et al., Proc. Natl. Acad. Sci. USA, 1991, 88, 5252; Nelken, N. A., J. Clin. Invest., 1991, 88, 1121), rheumatoid arthritis (see for example Koch, A. E., et al., J. Clin. Invest., 1992, 90, 772; Akahoshi, T., et al., Arthritis Rheum., 1993, 36, 762; Robinson, E., et al., Clin. Exp. Immunol., 101, 398), nephritis (see for example Noris, M., et al., Lab. Invest., 1995, 73, 804; Wada, T., at al., Kidney Int., 1996, 49, 761; Gesualdo, L., et al., Kidney Int., 1997, 51, 155), nephropathy (see for example Saitoh, A., et al., J. Clin. Lab. Anal., 1998, 12, 1; Yokoyama, H., et al., J. Leukoc. Biol., 1998, 63, 493), pulmonary fibrosis, pulmonary sarcoidosis (see for example Sugiyama, Y., et al., Internal Medicine, 1997, 36, 856), asthma (see for example Karina, M., et al., J. Invest. Allergol. Clin. Immunol., 1997, 7, 254; Stephene, T. H., Am. J. Respir. Crit. Care Med., 1997, 156, 1377; Sousa, A. R., et al., Am. J. Respir. Cell Mol. Biol., 1994, 10, 142), multiple sclerosis (see for example McManus, C., et al., J. Neuroimmunol., 1998, 86, 20), psoriasis (see for example Gillitzer, R., et al., J. Invest. Dermatol., 1993, 101, 127), inflammatory bowel disease (see for example Grimm, M. C., et al., J. Leukoc. Biol., 1996, 59, 804; Reinecker, H. C., et al., Gastroenterology, 1995, 106, 40), myocarditis (see for example Seino, Y., et al., Cytokine, 1995, 7, 301), endometriosis (see for example Jolicoeur, C., et al., Am. J. Pathol., 1998, 152, 125), intraperitoneal adhesion (see for example Zeyneloglu, H. B., et al., Human Reproduction, 1998, 13, 1194), congestive heart failure (see for example Aurust, P., et al., Circulation, 1998, 97, 1136), chronic liver disease (see for example Marra, F., et al., Am. J. Pathol., 1998, 152, 423), viral meningitis (see for example Lahrtz, F., et al., Eur. J. Immunol., 1997, 27, 2484), Kawasaki disease (see for example Wong, M.; et al., J. Rheumatol., 1997, 24, 1179) and sepsis (see for example Salkowski, C. A.; et al., Infect. Immun., 1998, 66, 3569). Furthermore, anti-MCP-1 antibody has been reported to show an inhibitory effect or a therapeutic effect in animal models of rheumatoid arthritis (see for example Schimmer, R. C., et al., J. Immunol., 1998, 160, 1466; Schrier, D. J., J. Leukoc. Biol., 1998, 63, 359; Ogata, H., et al., J. Pathol., 1997, 182, 106), multiple sclerosis (see for example Karpus, W. J., et al., J. Leukoc. Biol., 1997, 62, 681), nephritis (see for example Lloyd, C. M., et al., J. Exp. Med., 1997, 185, 1371; Wada, T., et al., FASEB J., 1996, 10, 1418), asthma (see for example Gonzalo, J.-A., et al., J. Exp. Med., 1998, 188, 157; Lukacs, N. W., J. Immunol., 1997, 158, 4398), atherosclerosis (see for example Guzman, L. A., et al., Circulation, 1993, 88 (suppl.), I-371), delayed type hypersensitivity (see for example Rand, M. L., et al., Am. J. Pathol., 1996, 148, 855), pulmonary hypertension (see for example Kimura, H., et al., Lab. Invest., 1998, 78, 571), and intraperitoneal adhesion (see for example Zeyneloglu, H. B., et al., Am. J. Obstet. Gynecol., 1998, 179, 438). A peptide antagonist of MCP-1, MCP-1(9-76), has been also reported to inhibit arthritis in the mouse model (see Gong, J.-H., J. Exp., 4ed., 1997, 186, 131), as well as studies in MCP-1-deficient mice have shown that MCP-1 is essential for monocyte recruitment in vivo (see Lu, B., et al., J. Exp. Med., 1998, 187, 601; Gu, L., et al., Moll. Cell, 1998, 2, 275).

The literature indicates that chemokines such as MCP-1 and MIP-1α attract monocytes and lymphocytes to disease sites and mediate their activation and thus are thought to be intimately involved in the initiation, progression and maintenance of diseases deeply involving monocytes and lymphocytes, such as atherosclerosis, restenosis, rheumatoid arthritis, psoriasis, asthma, ulcerative colitis, nephritis (nephropathy), multiple sclerosis, pulmonary fibrosis, myocarditis, hepatitis, pancreatitis, sarcoidosis, Crohn's disease, endometriosis, congestive heart failure, viral meningitis, cerebral infarction, neuropathy, Kawasaki disease, and sepsis (see for example Rovin, B. H., et al., Am. J. Kidney. Dis., 1998, 31, 1065; Lloyd, C., et al., Curr. Opin. Nephrol. Hypertens., 1998, 7, 281; Conti, P., et al., Allergy and Asthma Proc., 1998, 19, 121; Ransohoff, R. M., et al., Trends Neurosci., 1998, 21, 154; MacDermott, R. P., et al., Inflammatory Bowel Diseases, 1998, 4, 54).

The chemokines bind to specific cell-surface receptors belonging to the family of G-protein-coupled seven-transmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration.

Genes encoding receptors of specific chemokines have been cloned, and it is known that these receptors are G protein-coupled seven-transmembrane receptors present on various leukocyte populations. So far, at least five CXC chemokine receptors (CXCR1-CXCR5) and eight CC chemokine receptors (CCR1-CCR8) have been identified. For example IL-8 is a ligand for CXCR1 and CXCR2, MIP-1α is that for CCR1 and CCR5, and MCP-1 is that for CCR2A and CCR2B (for reference, see for example, Holmes, W. E., et al., Science 1991, 253, 1278-1280; Murphy P. M., et al., Science, 253, 1280-1283; Neote, K. et al, Cell, 1993, 72, 415-425; Charo, I. F., et al., Proc. Natl. Acad. Sci. USA, 1994, 91, 2752-2756; Yamagami, S., et al., Biochem. Biophys. Res. Commun., 1994, 202, 1156-1162; Combadier, C., et al., The Journal of Biological Chemistry, 1995, 270, 16491-16494, Power, C. A., et al., J. Biol. Chem., 1995, 270, 19495-19500; Samson, M., et al., Biochemistry, 1996, 35, 3362-3367; Murphy, P. M., Annual Review of Immunology, 1994, 12, 592-633). It has been reported that lung inflammation and granuroma formation are suppressed in CCR1-deficient mice (see Gao, J.-L., et al., J. Exp. Med., 1997, 185, 1959; Gerard, C., et al., J. Clin. Invest., 1997, 100, 2022), and that recruitment of macrophages and formation of atherosclerotic lesion decreased in CCR2-deficient mice (see Boring, L., et al., Nature, 1998, 394, 894; Kuziel, W. A., et al., Proc. Natl. Acad. Sci., USA, 1997, 94, 12053; Kurihara, T., et al., J. Exp. Med., 1997, 186, 1757; Boring, L., et al., J. Clin. Invest., 1997, 100, 2552).

Chemokine receptors are also known as coreceptors for viral entry leading to viral infection such as, for example, HIV infection. Reverse transcription and protein processing are the classic steps of the viral life cycle which antiretroviral therapeutic agents are designed to block. Although many new drugs that are believed to block viral entry hold promise, there is currently no agent to which HIV-1 has not been able to acquire resistance. Multiple rounds of viral replication are required to generate the genetic diversity that forms the basis of resistance. Combination therapy in which replication is maximally suppressed remains a cornerstone of treatment with entry inhibitors, as with other agents. The targeting of multiple steps within the viral entry process is believed to have the potential for synergy (Starr-Spires et al., *Clin. Lab. Med.*, 2002, 22(3), 681.)

HIV-1 entry into CD4(+) cells requires the sequential interactions of the viral envelope glycoproteins with CD4 and a coreceptor such as the chemokine receptors CCR5 and CXCR4. A plausible approach to blocking this process is to use small molecule antagonists of coreceptor function. The TAK-779 molecule is one such antagonist of CCR5 that acts to prevent HIV-1 infection. TAK-779 inhibits HIV-1 replication at the membrane fusion stage by blocking the interaction of the viral surface glycoprotein gp120 with CCR5. The binding site for TAK-779 on CCR5 is located near the extracellular surface of the receptor, within a cavity formed between transmembrane helices 1, 2, 3, and 7 (Dragic et al., *Proc. Nail. Acad. Sci. USA,* 2000, 97(10), 5639).

The chemokine receptors CXCR4 and CCR5 are believed to be used as co-receptors by the T cell-tropic (X4) and macrophage-tropic (R5) HIV-1 strains, respectively, for entering their host cells. Propagation of R5 strains of HIV-1 on CD4 lymphocytes and macrophages requires expression of the CCR5 coreceptor on the cell surface. Individuals lacking CCR5 (CCR5 Delta 32 homozygous genotype) are phenotypically normal and resistant to infection with HIV-1. Viral entry can be inhibited by the natural ligands for CXCR4 (the CXC chemokine SDF-1) and CCR5 (the CC chemokines RANTES, MIP-1alpha and MIP-1beta). The first non-peptidic compound that interacts with CCR5, and not with CXCR4, is a quaternary ammonium derivative, called TAK-779, which also has potent but variable anti-HIV activity (De Clercq et al., *Antivir. Chem. Chemother.* 2001, 12 Suppl. 1, 19.

SCH—C(SCH 351125) is another small molecule inhibitor of HIV-1 entry via the CCR5 coreceptor. SCH—C, an oxime-piperidine compound, is a specific CCR5 antagonist as determined in multiple receptor binding and signal transduction assays. This compound specifically inhibits HIV-1 infection mediated by CCR5 in U-87 astroglioma cells but has no effect on infection of CXCR4-expressing cells. (Strizki et al, *Proc. Natl. Acad. Sci. USA,* 2001, 98(22), 12718 or Tremblay et al., *Antimicrobial Agents and Chemotherapy,* 2002, 46(5), 1336).

AD101, chemically related to SCH—C, also inhibits the entry of human immunodeficiency virus type 1 (HIV-1) via human CCR5. It has been found that AD101 inhibits HIV-1 entry via rhesus macaque CCR5 while SCH—C does not. Among the eight residues that differ between the human and macaque versions of the coreceptor, only one, methionine-198, accounts for the insensitivity of macaque CCR5 to inhibition by SCH—C. Position 198 is in CCR5 transmembrane (TM) helix 5 and is not located within the previously defined binding site for AD101 and SCH—C, which involves residues in TM helices 1, 2, 3, and 7. Based on studies of amino acid substitutions in CCR5, it has been suggested that the region of CCR5 near residue 198 can influence the conformational state of this receptor. (Billick et al., 2004, *J. Virol.,* 78(8), 4134).

Accordingly, drugs which inhibit the binding of chemokines to their respective receptors can be useful as pharmaceutical agents which inhibit the action of chemokines on target cells and/or block viral entry into cells expressing these receptors. The identification of compounds that modulate the activity of chemokine receptors or block the binding of viral proteins represents an excellent drug design approach to the development of pharmacological agents for the treatment of inflammatory conditions, viral infection and other diseases associated with chemokine receptor activation. The compounds of the present invention help fulfill these and other needs.

SUMMARY OF THE INVENTION

The present invention provides compounds of Formula I:

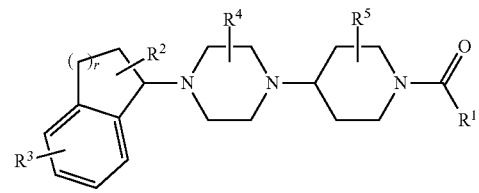

or pharmaceutically acceptable salt or prodrug thereof, wherein constituent members are defined herein.

The present invention further provides compositions comprising the compounds of Formula I and a pharmaceutically acceptable carrier.

The present invention further provides methods of modulating activity of a chemokine receptor comprising contacting the chemokine receptor with a compound of Formula I.

The present invention further provides methods of treating a disease associated with expression or activity of a chemokine receptor in a patient comprising administering to said patient a therapeutically effective amount of a compound of Formula I.

The present invention further provides methods of treating a disease or condition selected from an inflammatory disease, immune disorder, and viral infection in a patient comprising administering to the patient a therapeutically effective amount of a compound of Formula I.

The present invention further provides methods of treating HIV infection in a patient comprising administering to said patient a therapeutically effective amount of a compound of Formula I.

DETAILED DESCRIPTION

The present invention provides, inter alia, compounds of Formula I:

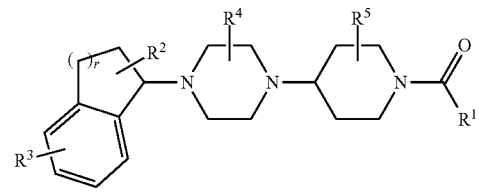

or pharmaceutically acceptable salt or prodrug thereof, wherein:

$R^1$ is heteroaryl optionally substituted by one or more $R^6$;

$R^2$ is H, halo, cyano, nitro, $C_1$-$C_6$ alkyl, $C_1$-$C_6$ haloalkyl, $C_2$-$C_6$ alkenyl, $C_2$-$C_6$ alkynyl, aryl, heteroaryl, $C_3$-$C_7$ cycloalkyl, heterocycloalkyl, $SOR^7$, $SO_2R^7$, $COR^8$, $OR^9$, $SR^9$, $COOR^9$, $NR^{10}R^{11}$ or $NR^{10}COR^8$;

$R^3$ is F, Cl, Br, I, $C_1$-$C_4$ haloalkyl, $C_1$-$C_4$ haloalkoxy or heteroaryl;

$R^4$ is H, $C_1$-$C_6$ alkyl, $C_2$-$C_6$ alkenyl, $C_2$-$C_6$ alkynyl or $C_1$-$C_6$ haloalkyl;

$R^5$ is H, $C_1$-$C_6$ alkyl, $C_2$-$C_6$ alkenyl, $C_2$-$C_6$ alkynyl or $C_1$-$C_6$ haloalkyl;

$R^6$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, amino, ($C_1$-$C_6$ alkyl)amino or di($C_1$-$C_6$ alkyl)amino;

$R^7$ is H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl, ($C_3$-$C_7$ cycloalkyl)alkyl, heterocycloalkylalkyl, or $NR^{12}R^{13}$;

$R^8$ is H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl, ($C_3$-$C_7$ cycloalkyl)alkyl, heterocycloalkylalkyl, or $NR^{12}R^{13}$;

$R^9$ is H, $C_1$-$C_6$ alkyl, $C_2$-$C_6$ alkenyl, $C_2$-$C_6$ alkynyl, $C_1$-$C_6$ haloalkyl, alkoxyalkyl, haloalkoxyalkyl, aryloxyalkyl, heteroaryloxyalkyl, cycloalkyloxyalkyl, heterocycloalkyloxyalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;

$R^{10}$ and $R^{11}$ are each, independently, H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;

or $R^{10}$ and $R^{11}$ together with the N atom to which they are attached form a 3-, 4-, 5-, 6-, or 7-membered heterocycloalkyl group;

$R^{12}$ and $R^{13}$ are each, independently, H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;

or $R^{12}$ and $R^{13}$ together with the N atom to which they are attached form a 3-, 4-, 5-, 6-, or 7-membered heterocycloalkyl group; and r is 1, 2 or 3.

In some embodiments, $R^1$ is a 5-, 6-, 9- or 10-membered heteroaryl group containing at least one ring-forming N atom, wherein said 5-, 6-, 9- or 10-membered heteroaryl group is optionally substituted by 1, 2, 3 or 4 $R^6$ groups.

In some embodiments, $R^1$ is a 9- or 10-membered heteroaryl group containing at least one ring-forming N atom, wherein said 6-membered heteroaryl group is optionally substituted by 1, 2, 3 or 4 $R^6$ groups.

In some embodiments, $R^1$ is a 6- or 5-membered heteroaryl group containing at least one ring-forming N atom, wherein said 5-membered heteroaryl group is optionally substituted by 1, 2, 3 or 4 $R^6$ groups.

In some embodiments, $R^1$ is a 6-membered heteroaryl group containing at least one ring-forming N atom, wherein said 6-membered heteroaryl group is optionally substituted by 1, 2, 3 or 4 $R^6$ groups.

In some embodiments, $R^1$ is a 5-membered heteroaryl group containing at least one ring-forming N atom, wherein said 5-membered heteroaryl group is optionally substituted by 1, 2, 3 or 4 $R^6$ groups.

In some embodiments, $R^1$ is quinolinyl, isoquinolinyl, naphthyridinyl, indolyl, indazolyl, pyridyl, pyrimidinyl, N-oxopyridyl, N-oxopyrimindinyl, isoxazole, pyrazole, pyrrolyl, imidazolyl, oxazolyl or thiazolyl, each optionally substituted by 1, 2, 3 or 4 $R^6$ groups.

In some embodiments, $R^1$ is quinolinyl, isoquinolinyl, naphthyridinyl, pyridyl, pyrimidinyl, N-oxopyridyl, isoxazole or pyrazole, each optionally substituted by 1, 2, 3 or 4 $R^6$ groups.

In some embodiments, $R^1$ is pyridyl, pyrimidinyl, N-oxopyridyl, N-oxopyrimindinyl, isoxazole, pyrazole, pyrrolyl, imidazolyl, oxazolyl or thiazolyl, each optionally substituted by 1, 2, 3 or 4 $R^6$ groups.

In some embodiments, $R^1$ is pyridyl, pyrimidinyl, N-oxopyridyl, isoxazole or pyrazole, each optionally substituted by 1, 2, 3 or 4 $R^6$ groups.

In some embodiments, $R^1$ is:

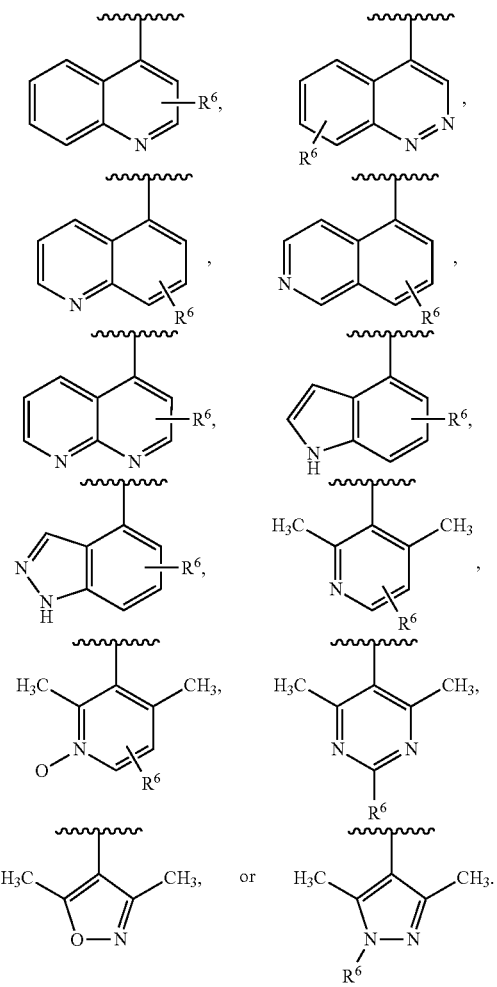

In some embodiments, $R^1$ is:

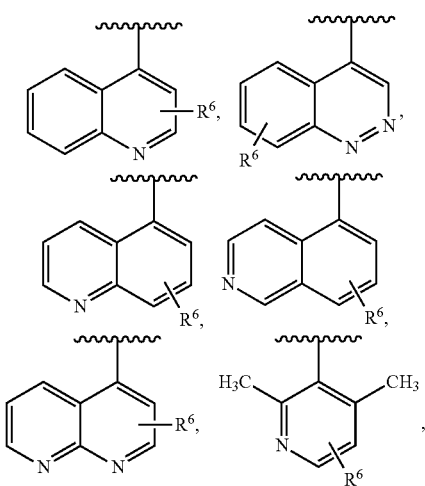

-continued

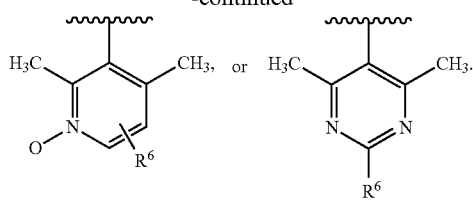 or 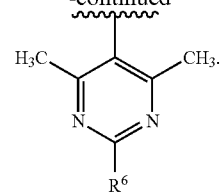

In some embodiments, $R^1$ is:

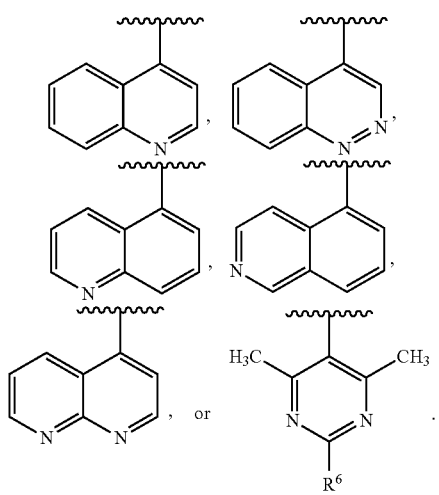

In some embodiments $R^1$ is

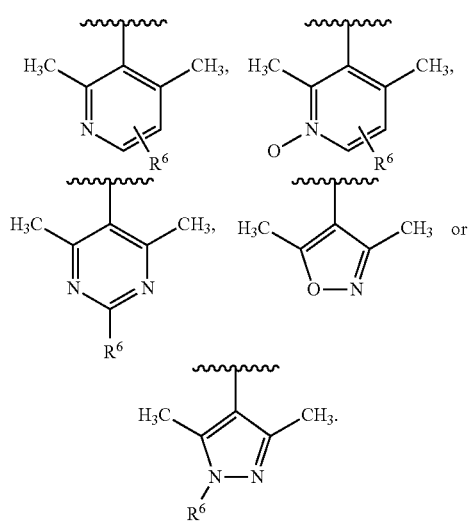

In some embodiments, $R^1$ is

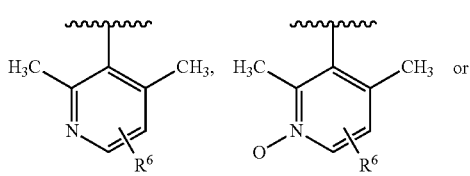

-continued

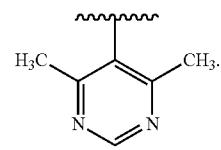 [SMILES: *c1c(C)ncnc1C]

In some embodiments, $R^1$ is

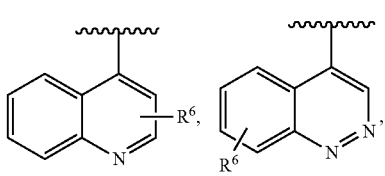

In some embodiments, $R^2$ is H, $C_1$-$C_6$ alkyl, $C_1$-$C_6$ haloalkyl, $OR^9$, $SR^9$ or $NR^{10}R^{11}$.

In some embodiments, $R^2$ is H or $OR^9$.

In some embodiments, $R^3$ is F, Br, $CF_3$, or 6- or 5-membered heteroaryl.

In some embodiments, $R^3$ is F, Br, $CF_3$, $OCF_3$, thiazolyl, pyrimidinyl, pyridyl.

In some embodiments, $R^3$ is F, Br, or $CF_3$.

In some embodiments, $R^4$ is $C_1$-$C_6$ alkyl.

In some embodiments, $R^4$ is methyl.

In some embodiments, $R^5$ is $C_1$-$C_6$ alkyl.

In some embodiments, $R^5$ is methyl.

In some embodiments, r is 1.

In some embodiments, r is 2.

In some embodiments, the compounds of the invention have Formula IIa or IIb:

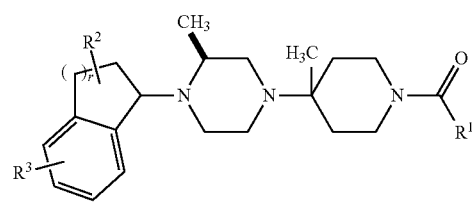

IIa

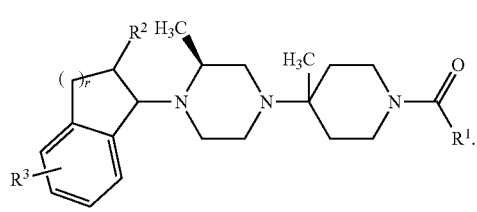

IIb

In some embodiments of compounds having Formula IIa or IIb, $R^1$ is:

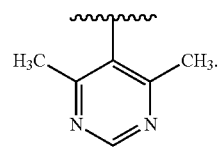 [SMILES: *c1c(C)ncnc1C]

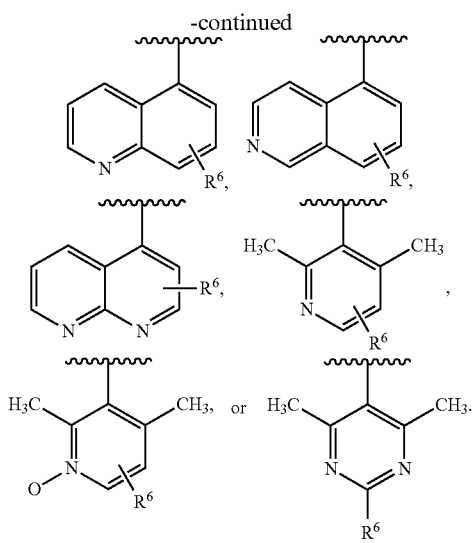

In some embodiments of compounds having Formula IIa or IIb, R$^1$ is:

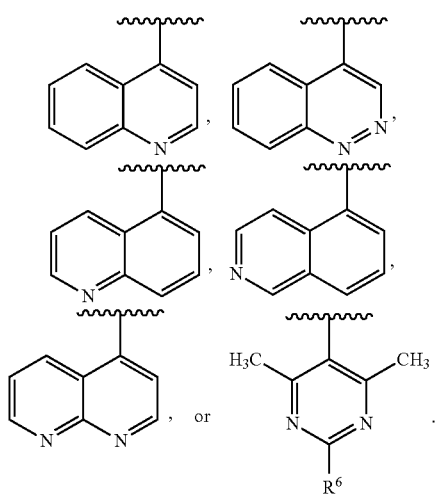

In some embodiments of compounds having Formula IIa or IIb, R$^1$ is:

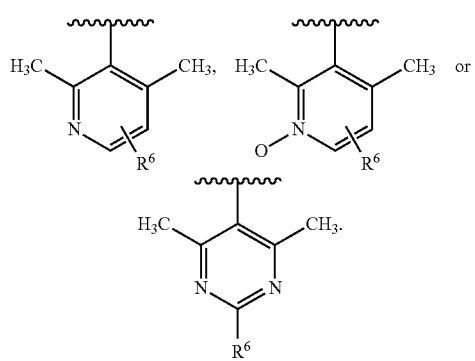

In some embodiments of compounds having Formula IIa or IIb, R$^1$ is

In some embodiments of compounds having Formula IIa or IIb, R$^2$ is H, C$_1$-C$_6$ alkyl, C$_1$-C$_6$ haloalkyl, OR$^9$, SR$^9$ or NR$^{10}$R$^{11}$.

In some embodiments of compounds having Formula IIa or IIb, R$^2$ is H or OR$^9$.

In some embodiments of compounds having Formula IIa or IIb, R$^3$ is F, Br, CF$_3$, 5- or 6-membered heteroaryl.

In some embodiments of compounds having Formula IIa or IIb, R$^3$ is F, Br, or CF$_3$.

It is appreciated that certain features of the invention, which are, for clarity, described in the context of separate embodiments, can also be provided in combination in a single embodiment. Conversely, various features of the invention which are, for brevity, described in the context of a single embodiment, may also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include ethynyl, propynyl, butynyl, pentynyl, and the like.

As used herein, "haloalkyl" refers to an alkyl group having one or more halogen substituents. Example haloalkyl groups include CF$_3$, C$_2$F$_5$, CHF$_2$, CCl$_3$, CHCl$_2$, C$_2$Cl$_5$, and the like. An alkyl group in which all of the hydrogen atoms are replaced with halogen atoms can be referred to as "perhaloalkyl." Example perhaloalkyl groups include CF$_3$ and C$_2$F$_5$.

As used herein, "aryl" refers to monocyclic or polycyclic aromatic hydrocarbons such as, for example, phenyl, naphthyl, anthracenyl, phenanthrenyl, indanyl, indenyl, and the like. In some embodiments, aryl groups have from 6 to about 18 carbon atoms.

As used herein, "cycloalkyl" refers to non-aromatic cyclic hydrocarbons, including cyclized alkyl, alkenyl, and alkynyl groups. Cycloalkyl groups can include bi- or poly-cyclic ring systems and can optionally contain unsaturations. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like. Cycloalkyl groups can have from about 3 to about 20, 3 to about 12, or 3 to about 7 carbon atoms.

As used herein, "heteroaryl" groups are monocyclic and polycyclic aromatic hydrocarbons that have at least one heteroatom ring member such as sulfur, oxygen, or nitrogen. Heteroaryl groups include, without limitation, pyridyl, N-oxopyridyl, pyrimidinyl, N-oxopyrimidinyl, pyrazinyl, pyridazinyl, triazinyl, naphthyridinyl, furyl, quinolyl, isoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms. In some embodiments, the heteroaryl group has 5 to 50, 5 to 20, 5 to 14 or 5 to 7 ring members. In some embodiments, the heteroaryl group is a 5-, 6-, 9-, or 10-membered group. In some embodiments, the heteroaryl group contains at least one ring-forming N atom.

As used herein, "heterocycloalkyl" refers to a cyclized, non-aromatic hydrocarbon including cyclized alkyl, alkenyl, and alkynyl groups where one or more of the ring-forming carbon atoms is replaced by a heteroatom such as an O, N, or S atom. Example heterocycloalkyl groups include piperidinyl, pyrrolidinyl, morpholino, tetrahydrofuranyl, and the like. Also included in the definition of heterocycloalkyl are moieties that have one or more aromatic rings fused (i.e., having a bond in common with) to the non-aromatic heterocyclic ring, for example phthalimidyl, naphthalimidyl pyromellitic diimidyl, phthalanyl, and benzo derivatives of saturated heterocycles such as indolene and isoindoline groups. In some embodiments, the heterocycloalkyl group has 3 to 20, 3 to 14 or 3 to 7 ring members.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like. "Haloalkoxy" refers to an —O-haloalkyl group.

As used here, "arylalkyl" refers to an alkyl group substituted by at least one aryl group. An example arylalkyl group is benzyl.

As used herein, "cycloalkylalkyl" refers to an alkyl group substituted by at least one cycloalkyl group.

As used herein, "heteroarylalkyl" refers to an alkyl group substituted by at least one heteroaryl group.

As used herein, "heterocycloalkylalkyl" refers to an alkyl group substituted by at least one heterocycloalkyl group.

As used herein, "aryloxy" refers to —O-aryl.

As used herein, "heteroaryloxy" refers to —O-heteroaryl.

As used herein, "cycloalkyloxy" refers to —O-cycloalkyl.

As used herein, "heterocycloalkyloxy" refers to —O-heterocycloalkyl.

As used herein, "alkoxyalkyl" refers to an alkyl group substituted by at least one alkoxy group. Example alkoxyalkyl groups include methoxymethyl, methoxyethyl, methoxypropyl and the like.

As used herein, "haloalkoxyalkyl" refers to an alkyl group substituted by at least one haloalkoxy group.

As used herein, "arylalkoxyalkyl" refers to an alkyl group substituted by at least one aryloxy group.

As used herein, "cycloalkyloxyalkyl" refers to an alkyl group substituted by at least one cycloalkyloxy group.

As used herein, "heteroaryloxyalkyl" refers to an alkyl group substituted by at least one heteroaryloxy group.

As used herein, "heterocycloalkloxyalkyl" refers to an alkyl group substituted by at least one heterocycloalkyloxy group.

As used herein, the term "amino" refers to $NH_2$. Similarly, the term "alkylamino" refers to an amino group substituted by an alkyl group, and the term "dialkylamino" refers to an amino group substituted by two alkyl groups.

As used herein, "substituted" indicates that at least one hydrogen atom of a chemical group is replaced by a non-hydrogen moiety. When a chemical group herein is "substituted" it may have up to the full valance of substitution, provided the resulting compound is a stable compound or stable structure; for example, a methyl group may be substituted by 1, 2, or 3 substituents, a methylene group may be substituted by 1 or 2 substituents, a phenyl group may be substituted by 1, 2, 3, 4, or 5 substituents, and the like.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include tautomeric forms, such as keto-enol tautomers. Tautomeric forms can be in equilibrium or sterically locked into one form by appropriate substitution.

Compounds of the invention also include hydrates and solvates.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Synthesis

Compounds of the invention, including salts, hydrates, and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Example synthetic routes to compounds of the invention are provided in Schemes 1-5 below, where constituent members of the depicted formulae are defined herein.

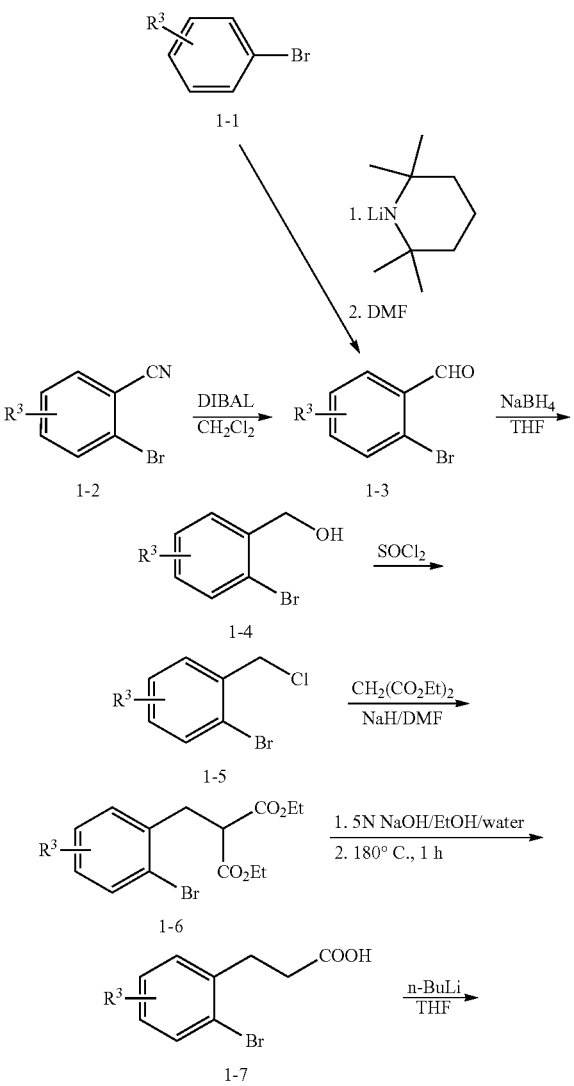

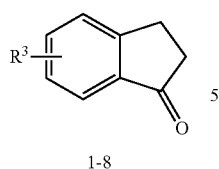

1-8

Indanone intermediates of Formula 1-8 can be synthesized using procedures outlined in Scheme 1. For example, the benzaldehyde 1-3 can be generated by deprotonation of the bromobenzene (1-1) with a strong base such as 2,2,6,6-tetramethylpiperidine/n-butyllithium followed by quenching, such as with DMF. Alternatively, the benzaldehyde 1-3 can be generated by reduction of the benzonitrile (1-2) using an appropriate reducing agent such as diisobutylaluminum hydride (DIBAL). Following reduction of the aldehyde to alcohol using a further reducing agent such as sodium borohydride, the resulting alcohol 1-4 can be converted to a chloride by treatment with a suitable chlorinating agent such as thionyl chloride. Displacement of the chloride 1-5 with diethyl malonate using a suitable base (e.g., sodium hydride) produces the diester 1-6. Saponification of the diester using a base such as sodium hydroxide followed by decarboxylation yields the monocarboxylic acid 1-7. Treatment of 1-7 with an appropriate cyclizing agent such as n-butyl lithium affords the cyclized product indan-1-one 1-8.

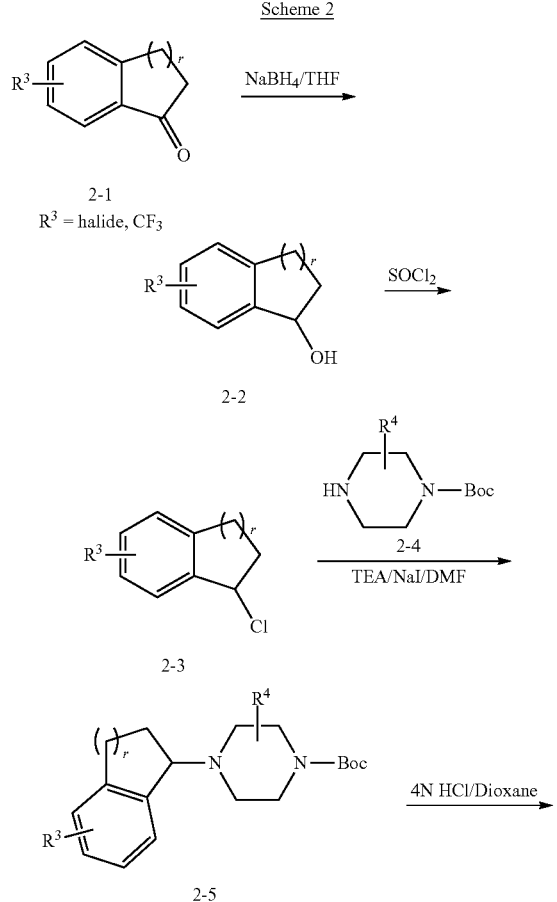

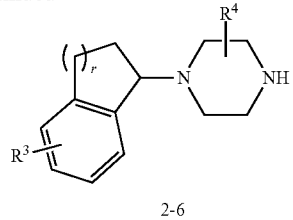

2-6

Intermediates of Formula 2-6 can be synthesized using the methods depicted in Scheme 2. A ketone derivative of Formula 2-1 can be subjected to a reduction using a suitable reducing agent such as sodium borohydride to give the alcohol 2-2. After conversion of the alcohol to chloride using an appropriate chlorinating reagent such as $SOCl_2$, the chloride 2-3 is reacted with a piperazine derivative of Formula 2-4 to afford 2-5. Removal of Boc protecting group using an acid such as 4 N HCl in dioxane results in intermediates of Formula 2-6.

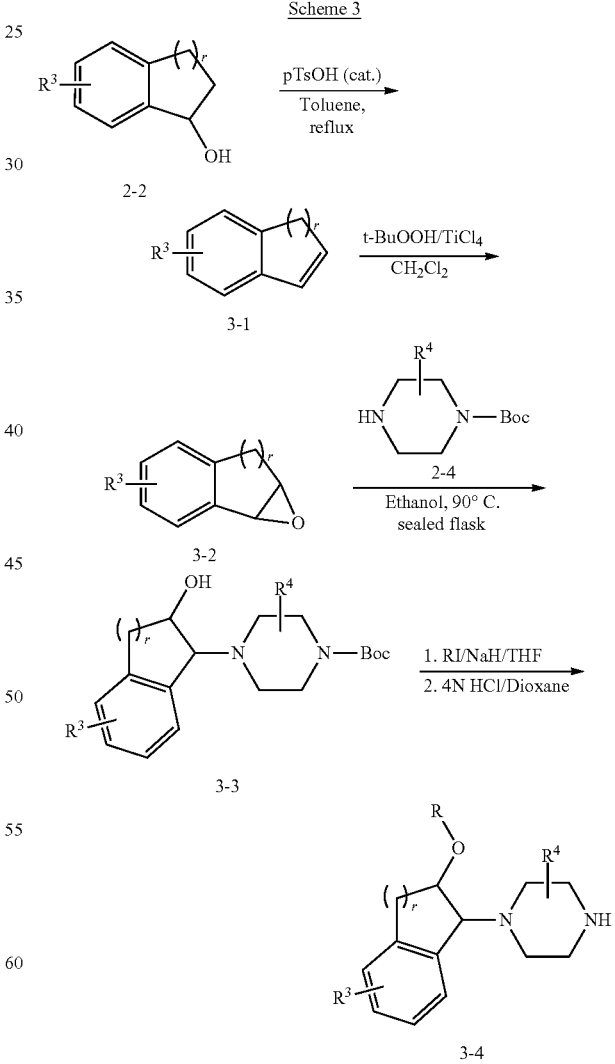

Intermediates of Formula 3-4 can be prepared using a sequence outlined in Scheme 3. The alcohol intermediate 2-2 is subjected to a dehydration under suitable conditions (e.g., p-TsOH, reflux in toluene) to give the indene 3-1. Epoxidation using an appropriate oxidant such as tert-butyl hydroperoxide yields the epoxide 3-2. Ring opening of the epoxide with a piperazine derivative of Formula 2-4 provides 3-3. Alkylation of the alcohol in 3-3 with an alkylating reagent such as alkyl iodide (RI) followed by removal of Boc using an acid affords intermediates of Formula 3-4 (wherein R is an alkyl group).

Scheme 4

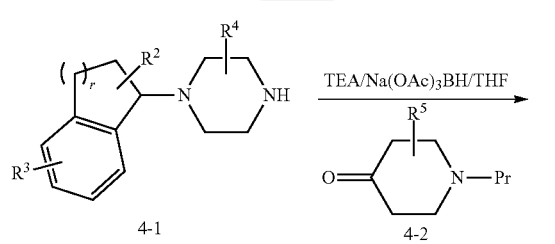

4-1    4-2

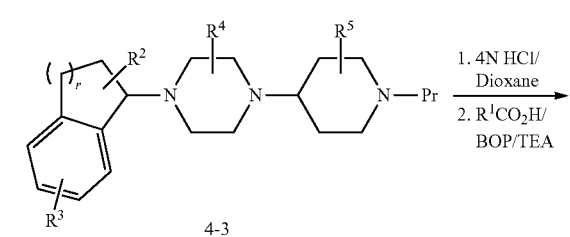

4-3

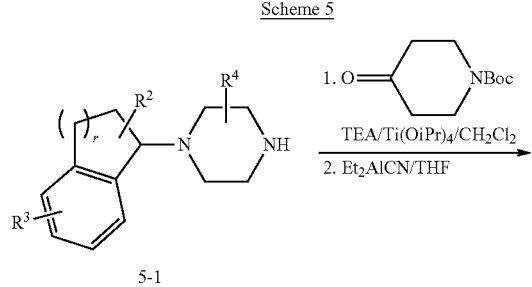

4-4

Compounds of Formula 4-4 can be prepared using the procedures described in Scheme 4. Reaction of the piperazine derivative of Formula 4-1 with the protected piperidine of Formula 4-2 (Pr is an amino protecting group such as Boc) provides derivative 4-3. Upon removal of the amino protecting group (Pr) using a suitable reagent (e.g., acid such as 4 N HCl in dioxane), the resulting free amine can be coupled with a carboxylic acid using a suitable coupling agent such as BOP to generate compounds of Formula 4-4.

Scheme 5

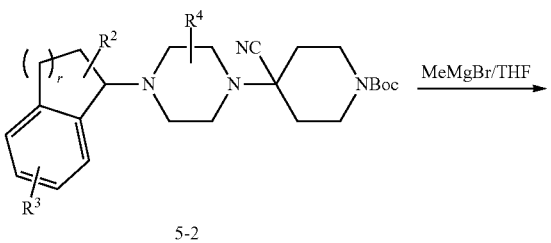

5-1

5-2

5-3

5-4

Compounds of Formula 5-4 can be prepared using the procedures described in Scheme 5. Reaction of the piperazine derivative of Formula 5-1 with tert-butyl 4-oxo-1-piperidinecarboxylate followed by treatment with diethylaluminum cyanide gives rise to the cyano derivative 5-2. Displacement of the cyano residue with methylmagnesium bromide yields 5-3. Upon removal of the Boc group using an acid such as 4 N HCl in dioxane, the resulting amine can be coupled with a carboxylic acid using a coupling agent such as BOP to generate compounds of Formula 5-4.

Scheme 6

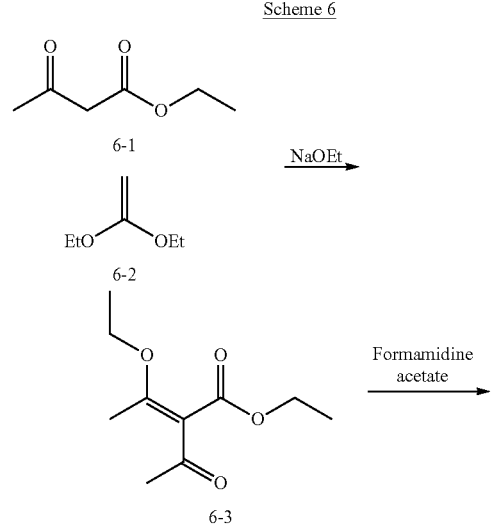

6-1

6-2

6-3

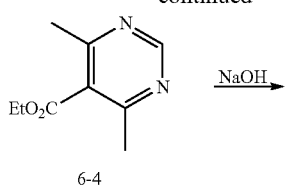

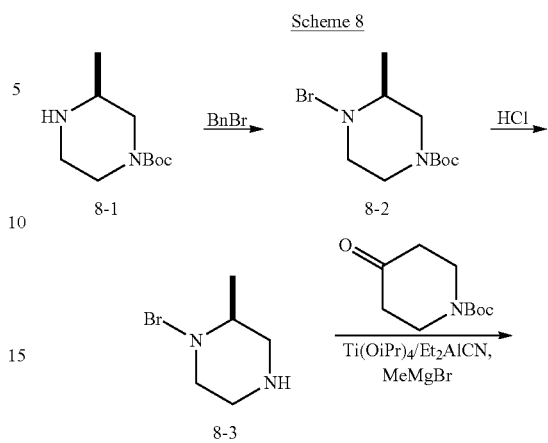

Scheme 8

4,6-Dimethylpyrimidine-5-carboxylic acids (6-5) can be prepared using the procedures outlined in Scheme 6. Reaction of ethyl acetoacetate with ketene diethylacetal in the presence of a base such as sodium ethoxide gives rise to the intermediate 6-3. Cyclization of 6-3 with formamidine acetate provides the ethyl ester 6-4 which is saponified to give the carboxylic acid 6-5.

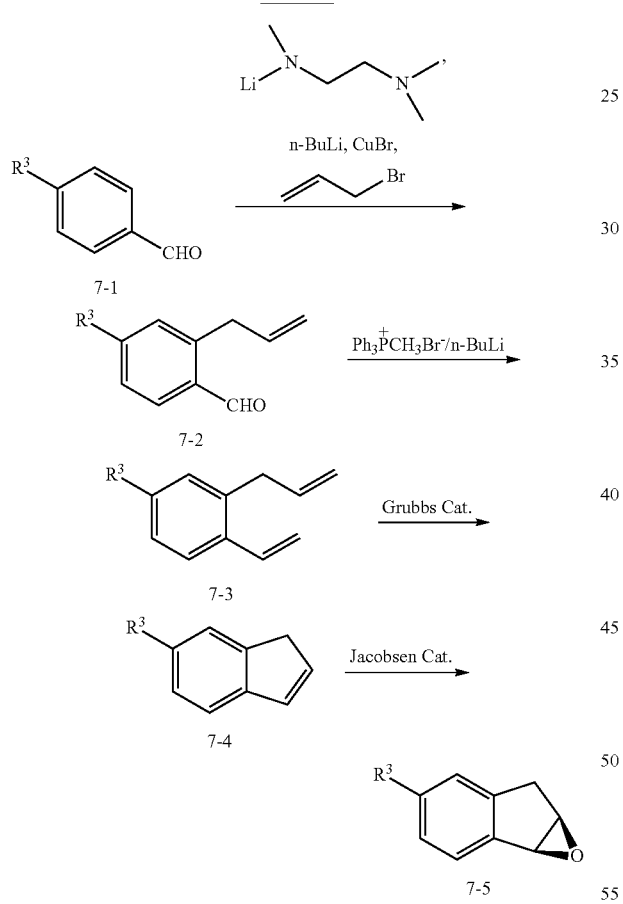

Alkylation of 4-Boc-2-methylpiperazine 8-1 with benzyl bromide followed by removing the Boc using an acid such HCl provides 8-3. Intermediate 8-3 can be converted to 8-4 using the method described in Scheme 5. Removal of the benzyl group in 8-4 by hydrogenation using Pd(OH)$_2$ as catalyst generates the intermediate 8-5.

Scheme 9

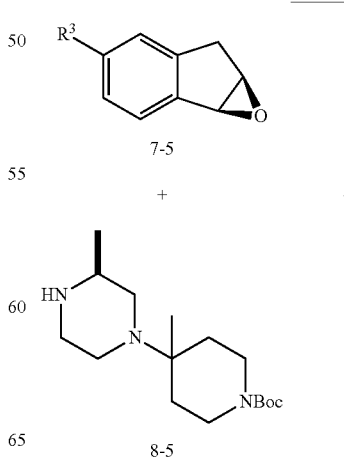

Alternatively, compounds of formula I can be synthesized using the procedures depicted in Schemes 7-9. Lithiation of a benzaldehyde derivative 7-1 with n-butyl lithium in the presence of N,N,N'-trimethylethane-1,2-diamine followed by quenching with allyl bromide provides the allyl derivative 7-2. Following conversion of the aldehyde to olefin by treatment with Ph$_3$PCH$_3$Br/n-BuLi, 7-3 is cyclized using Grubbs catalyst to give the indene derivative 7-4. Asymmetric epoxidation using Jacobsen's catalyst affords the epoxide 7-5.

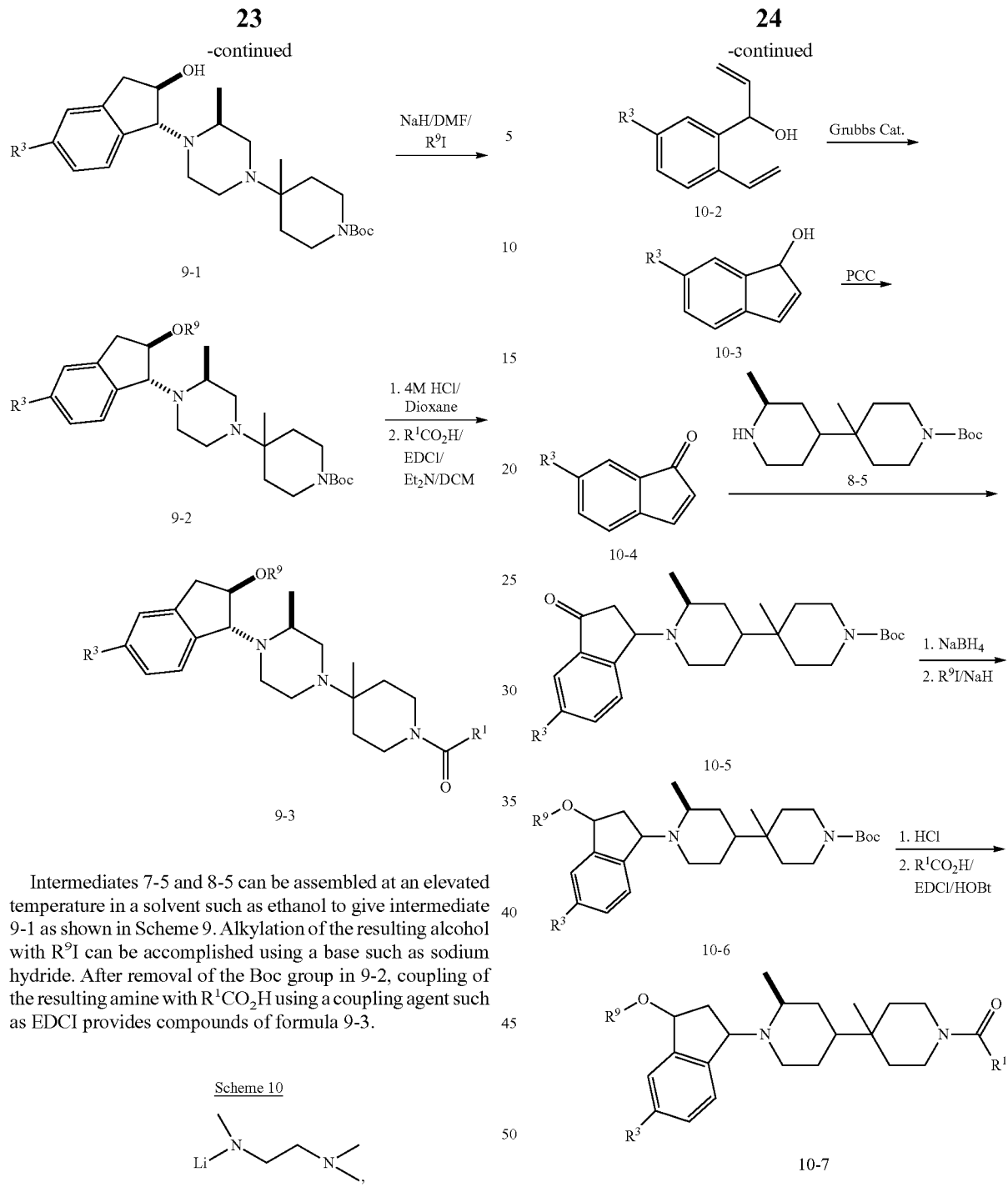

Intermediates 7-5 and 8-5 can be assembled at an elevated temperature in a solvent such as ethanol to give intermediate 9-1 as shown in Scheme 9. Alkylation of the resulting alcohol with $R^9I$ can be accomplished using a base such as sodium hydride. After removal of the Boc group in 9-2, coupling of the resulting amine with $R^1CO_2H$ using a coupling agent such as EDCI provides compounds of formula 9-3.

Alternatively, compounds of formula I can be prepared as shown in Scheme 10. A benzaldehyde derivative 7-1 can be alkylated by treatment with n-butyllithium in the presence of N,N,N'-trimethylethane-1,2-diaminene followed by quenching with acrolein. The resulting semiacetal 10-1 can be converted to an olefin by treating with $Ph_3PCH_3Br$/n-butyllithium. Cyclization using Grubbs catalyst gives rise to 3-hydroxyindene derivative 10-3 which can be subjected to an oxidation using an oxidant such as pyridinium chlorochromate (PCC). Michael addition of intermediate 8-5 to the resulting ketone 10-4 affords intermediate 10-5. Following reduction of the ketone to alcohol, alkylation with $R^9I$ can be accomplished using a base such as sodium hydride. Removal of Boc followed by coupling with $R^1CO_2H$ using a coupling agent such as EDCI/HOBt affords compounds of formula 10-7.

Methods

In some embodiments, compounds of the invention can modulate activity of one or more chemokine receptors. The term "modulate" is meant to refer to an ability to increase or decrease activity of a receptor. Accordingly, compounds of the invention can be used in methods of modulating a chemokine receptor by contacting the receptor with any one or more of the compounds or compositions described herein. In some embodiments, compounds of the present invention can act as inhibitors of chemokine receptors. In further embodiments, the compounds of the invention can be used to modulate activity of a chemokine receptor in an individual in need of modulation of the receptor by administering a modulating amount of a compound of Formula I.

In some embodiments, compounds of the invention can bind to a chemokine receptor in such a way to block or inhibit binding of endogenous and other chemokine receptor ligands. In some embodiments, the compounds of the invention can block or inhibit binding of exogenous ligands including viral proteins involved in viral entry into cells expressing the chemokine receptor. Accordingly, compounds of the invention can block viral entry and inhibit viral infection. In some embodiments, compounds of the invention can inhibit human immuno-deficiency virus (HIV) infection by, for example, blocking interaction of a chemokine receptor (e.g., CCR5) with HIV glycoprotein120 (gp120).

Chemokine receptors to which the present compounds bind and/or modulate include any chemokine receptor. In some embodiments, the chemokine receptor belongs to the CC family of chemokine receptors including, for example, CCR1, CCR2, CCR3, CCR4, CCR5, CCR6, CCR7, and CCR8. In some embodiments, the chemokine receptor is CCR2. In some embodiments, the chemokine receptor is CCR5.

The compounds of the invention can be selective. By "selective" is meant that the compound binds to or inhibits a chemokine receptor with greater affinity or potency, respectively, compared to at least one other chemokine receptor.

Compounds of the invention can be selective binders of CCR5, meaning that the compounds of the invention can bind to CCR5 with greater affinity than for another chemokine receptor such as at least one of CCR1, CCR2, CCR3, CCR4, CCR6, CCR7 and CCR8. In some embodiments, the compounds of the invention have binding selectivity for CCR5 over CCR2. In some embodiments, the compounds of the invention have binding selectivity for CCR5 over CCR1. In some embodiments, the compounds of the invention have binding selectivity for CCR5 over any other CCR. Selectivity can be at least about 10-fold, at least about 20-fold, at least about 50-fold, at least about 100-fold, at least about 200-fold, at least about 500-fold or at least about 1000-fold. In some embodiments, the compounds of the invention have binding affinity for CCR5 that is at least about 10-fold, at least about 20-fold, at least about 50-fold, at least about 100-fold, at least about 200-fold, at least about 500-fold or at least about 1000-fold greater than binding affinity for CCR1, CCR2 or any other chemokine receptor. Binding affinity can be measured according to routine methods in the art, such as according to the assays provided herein.

In some embodiments, the compounds of the invention can be selective inhibitors of CCR5, meaning that the compounds of the invention can inhibit activity of CCR5 more potently than for at least one other chemokine receptors such as, for example, CCR1, CCR2, CCR3, CCR4, CCR6, CCR7 and CCR8. In some embodiments, the compounds of the invention have inhibition selectivity for CCR5 over CCR2. In some embodiments, the compounds of the invention have inhibition selectivity for CCR5 over CCR1. In some embodiments, the compounds of the invention have inhibition selectivity for CCR5 over any other CCR. Selectivity can be at least about 10-fold, at least about 20-fold, at least about 50-fold, at least about 100-fold, at least about 200-fold, at least about 500-fold or at least about 1000-fold. In some embodiments, the compounds of the invention have inhibition affinity for CCR5 that is at least about 10-fold, at least about 20-fold, at least about 50-fold, at least about 100-fold, at least about 200-fold, at least about 500-fold or at least about 1000-fold greater than binding affinity for CCR1, CCR2 or any other chemokine receptor Inhibitor potency can be measured according to routine methods in the art, such as according to the assays provided herein.

Another aspect of the present invention pertains to methods of treating a chemokine receptor-associated disease or disorder in an individual (e.g., patient) by administering to the individual in need of such treatment a therapeutically effective amount or dose of a compound of the present invention or a pharmaceutical composition thereof. A chemokine receptor-associated disease can include any disease, disorder or condition that is directly or indirectly linked to expression or activity of the chemokine receptor. A chemokine receptor-associated disease can also include any disease, disorder or condition that can be prevented, ameliorated, or cured by modulating chemokine receptor activity. A chemokine receptor-associated disease can further include any disease, disorder or condition that is characterized by binding of an infectious agent such as a virus or viral protein with a chemokine receptor. In some embodiments, the chemokine receptor-associated disease is a CCR5-associated disease such as HIV infection.

Example chemokine receptor-associated diseases, disorders and conditions include inflammation and inflammatory diseases, immune disorders and viral infections. Example inflammatory diseases include diseases having an inflammatory component such as asthma, allergic rhinitis, restenosis, atherosclerosis, multiple sclerosis, Crohn's disease, ulcerative colitis, hypersensitivity lung diseases, hypersensitivity pneumonitis, eosinophilic pneumonias, delayed-type hypersensitivity, asthma, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis) and the like. Example immune disorders include rheumatoid arthritis, psoriatic arthritis, systemic lupus erythematosus, myastenia gravis, juvenile onset diabetes; glomerulonephritis, autoimmune throiditis, organ transplant rejection including allograft rejection and graft-versus-host disease. Example viral infections include HIV infection.

As used herein, the term "contacting" refers to the bringing together of indicated moieties in an in vitro system or an in vivo system. For example, "contacting" the chemokine receptor with a compound of the invention includes the administration of a compound of the present invention to an individual or patient, such as a human, having a chemokine receptor, as well as, for example, introducing a compound of the invention into a sample containing a cellular or purified preparation containing the chemokine receptor.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting further development of the pathology and/or symptomatology) such as stabilizing viral load in the case of a viral infection; and (3) ameliorating the disease; for example, ameliorating a disease, condition or disorder in an individual that is experiencing or displaying the pathology or symptomatology of the disease, condition or disorder (i.e., reversing the pathology and/or symptomatology) such as lowering viral load in the case of a viral infection.

One or more additional pharmaceutical agents such as, for example, anti-viral agents, antibodies, anti-inflammatory agents, and/or immunosuppressants can be used in combination with the compounds of the present invention for treatment of chemokine receptor-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(-)-FTC]; beta-L-FD4 (also called beta-L-D4C and named beta-L-2',3'-dicleoxy-5-fluoro-cytidene); DAPD, ((-)-beta-D-2,6,-diamino-purine dioxolane); and lodenosine (FddA).

Typical suitable NNRTIs include nevirapine (BI-RG-587); delaviridine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidi nedione); and (+)-calanolide A (NSC-675451) and B.

Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1 549.

Other antiviral agents include hydroxyurea, ribavirin, IL-2, IL-12, pentafuside and Yissum Project No. 11607.

In some embodiments, anti-inflammatory or analgesic agents contemplated for use in combination with the compounds of the present invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin-I inhibitor, an NNMA antagonist, an inhibitor of nitric oxide or an inhibitor of the synthesis of nitric oxide, a non-steroidal antiinflammatory agent, or a cytokine-suppressing antiinflammatory agent, for example, such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds can be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antfitussive such as codeine, hydrocodone, caramiphen, carbetapentane, or dextramethorphan; a diuretic; and a sedating or non-sedating antihistamine.

In some embodiments, pharmaceutical agents contemplated for use in combination with the compounds of the present invention can comprise (a) VLA-4 antagonists such as those described in U.S. Pat. No. 5,510,332, W095/15973, W096/01644, W096/06108, W096/20216, W096/229661, W096/31206, W096/4078, W097/030941, W097/022897 WO 98/426567 W098/53814, W098/53817, W098/538185, W098/54207, and W098/58902; (b) sterolds such as beclornethasone, methylpi-ednisolone, betamethasone, prednisone, dexamethasone, and hydrocortisone; (c) immunosuppressants such as cyclosporin, tacrolimus, raparnycin and other FK506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, asternizole, terfenadine, loratadine, cetirizine, fexofenadine, descarboethoxyloratadine, and the like; (e) non-steroidal anti-asthmatics such as terbutaline, metaproterenol, fenoterol, isoethaiine, albuterol, bitolterol, pirbuterol, theophylline, cromolyn sodium, atropine, ipratropium bromide, leukotriene antagonists (e.g., zafirlukast, montelukast, pranlukast, iralukast, pobilukast, SKB-106,203), leukotriene biosynthesis inhibitors (e.g., zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acernetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, rnefenamic acid, niflumic acid and tolfenarnic acid), biphenylcarboxylic acid derivatives (diflunisal and flufenisal), oxicarns (isoxicarn, piroxicam, sudoxicam and tenoxican), salicylates (acetyl salicylic acid, sulfasalazine) and the pyrazolones (apazone, benzpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chernokine receptors, especially CXCR-4, CCRI, CCR2, CCR3 and CCR5; (j) cholesterol lowering agents such as HMG-CoA reductase inhibitors (lovastatin, sirrivastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), U.-glucosidase inhibitors (acarbose) and orlitazones (troglitazone and pioglitazone); (l) preparations of interferon beta (interferon beta-lo., interferon beta-1 P);

(m) other compounds such as aminosalicylic acids, antimetabolites such as azathioprine and 6-mercaptopurine, and cytotoxic cancer chemotherapeutic agents. The weight ratio of the compound of the present invention to the second active ingredient may be varied and will depend upon the effective dose of each ingredient.

Pharmaceutical Formulations and Dosage Forms

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of Formula I above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, antibodies, immune suppressants, anti-inflammatory agents and the like. In some embodiments, the compounds of the invention are formulated in combination with one or more anti-viral agents including protease inhibitors and other agents used for anti-HIV therapy.

Labeled Compounds and Assay Methods

Another aspect of the present invention relates to radio-labeled compounds of Formula I that would be useful not only in radio-imaging but also in assays, both in vitro and in vivo, for localizing and quantitating the chemokine receptor in tissue samples, including human, and for identifying chemokine receptor ligands by inhibition binding of a radio-labeled compound. Accordingly, the present invention includes chemokine receptor assays that contain such radio-labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. The radionuclide that is incorporated in the instant radio-labeled compounds will depend on the specific application of that radio-labeled compound. For example, for in vitro chemokine receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the chemokine receptor. Accordingly, the ability of a test compound to compete with the radio-labeled compound for binding to the chemokine receptor directly correlates to its binding affinity.

Kits

The present invention also includes pharmaceutical kits useful, for example, in the treatment or prevention of chemokine-associated diseases or disorders, such as HIV infection, which include one or more containers containing a pharmaceutical composition comprising a therapeutically effective amount of a compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

5-({4-[(3S)-4-(5-Bromo-2,3-dihydro-1H-inden-1-yl)-3-methylpiperazin-1-yl]-4-methylpiperidin-1-yl}carbonyl)-4,6-dimethylpyrimidine

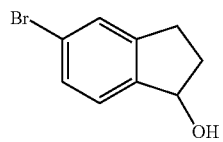

Step A

5-Bromo-1-indanol

To a solution of 5-bromo-1-indanone (2.0 g, 9.5 mmol) in THF (20 mL) was added NaBH$_4$ (0.5 g, 12.8 mmol). After stirring at room temperature overnight, the solution was quenched by addition of water. The resulting solution was extracted with EtOAc twice. The combined EtOAc layers were dried over Na$_2$SO$_4$ and concentrated under vacuum to give 2.0 g of the title compound as a solid. MS calculated for C$_9$H$_9$BrO: (M+H)$^+$212.9; found 194.9 (M+H—H$_2$O)$^+$, 197.0 (M+H—H$_2$O)$^+$.

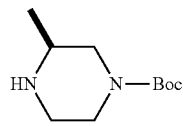

Step B tert-Butyl (3S)-3-methylpiperazine-1-carboxylate

To a solution of (2S)-2-methylpiperazine (20.0 g, 0.200 mol) in methylene chloride (300 mL) and triethylamine (20.4 g, 0.202 mol) was added dropwise a solution of di-tert-butyl dicarbonate (44.0 g, 0.202 mol) in CH$_2$Cl$_2$ (100 mL) over 5 hrs. The mixture was washed with water, brine, and then dried over MgSO$_4$ and concentrated. Column chromatography on silica (10-20% MeOH in EtOAc) afforded 32.0 g (80%) of the title compound as an oil.

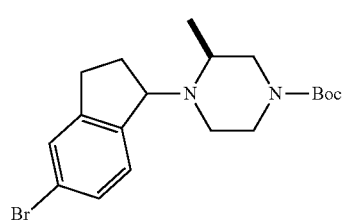 [SMILES: C[C@H]1CN(C(=O)OC(C)(C)C)CCN1C1CCc2cc(Br)ccc21]

Step C tert-Butyl (3S)-4-(5-bromo-2,3-dihydro-1H-inden-1-yl)-3-methylpiperazine-1-carboxylate 5-Bromo-1-indanol (1.0 g, 4.7 mmol) of Step A was dissolved in thionyl chloride (10 mL). After stirring at room temperature for 2 hrs, the solution was concentrated under vacuum. The residue was taken up in DMF (10 mL). To the mixture were added tert-butyl (3S)-3-methylpiperazine-1-carboxylate (0.94 g, 4.7 mmol), NaI (2 g, 13 mmol) and triethylamine (1.5 mL, 10 mmol). The resulting solution was stirred at 70° C. overnight. After cooling to room temperature, water was added. The solution was extracted with EtOAc twice. The combined EtOAc layers were washed with brine, dried over MgSO$_4$ and concentrated. Column chromatography on silica (50% EtOAc in hexane) provided two isomers. Isomer 1 (fast moving isomer): 0.36 g; MS calculated for C$_{19}$H$_{27}$BrN$_2$O$_2$ (M+H)$^+$395; found 395.1, 397.0. Isomer 2 (slow moving isomer): 0.33 g; MS found 395.1, 397.0.

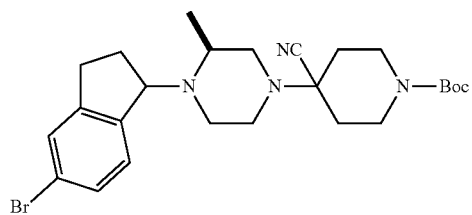 [SMILES: C[C@H]1CN(C2(C#N)CCN(C(=O)OC(C)(C)C)CC2)CCN1C1CCc2cc(Br)ccc21]

Step D tert-Butyl 4-[(3S)-4-(5-bromo-2,3-dihydro-1H-inden-1-yl)-3-methylpiperazin-1-yl]-4-cyanopiperidine-1-carboxylate Isomer 1 from Step C (0.33 g, 0.83 mmol) was dissolved in 4 N HCl in dioxane (4 mL). After stirring at room temperature for 2 h, the solution was concentrated. The residue was taken up in CH$_2$Cl$_2$ (5 mL). To it were added tert-butyl 4-oxo-1-piperidinecarboxylate (0.17 g, 0.85 mmol), Ti(Oi-Pr)$_4$ (0.87 mL) and triethylamine (0.6 mL). The mixture was stirred at room temperature overnight and the volatiles were removed under vacuum. The residue was dissolved in THF (5 mL). To the mixture was added a 1.0 M solution of diethylaluminum cyanide (1 mL). The resulting solution was stirred at 30° C. for 5 h and concentrated to provide the crude title compound (0.32 g) that was used for the next reaction without purification. MS calculated for C$_{25}$H$_{35}$BrN$_4$O$_2$: (M+H)$^+$503; found 503.1, 505.1.

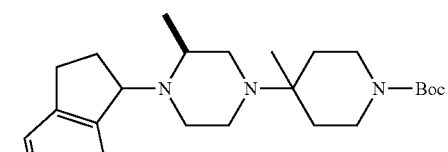

Step E tert-Butyl 4-[(3S)-4-(5-bromo-2,3-dihydro-1H-inden-1-yl)-3-methylpiperazin-1-yl]-4-methylpiperidine-1-carboxylate To a solution of tert-butyl 4-[(3S)-4-(5-bromo-2,3-dihydro-1H-inden-1-yl)-3-methylpiperazin-1-yl]-4-cyanopiperidine-1-carboxylate (0.32 g, 0.64 mmol) in THF (2 mL) was added a 3 M solution of methylmagnesium bromide (1.1 mL, 3.3 mmol). After stirring at room temperature overnight, the solution was concentrated. Purification on silica (2:1 hexane/EtOAc) afforded the title compound (0.25 g). MS calculated for $C_{25}H_{37}BrN_3O_2$: $(M+H)^+$491; found 491.2, 494.2.

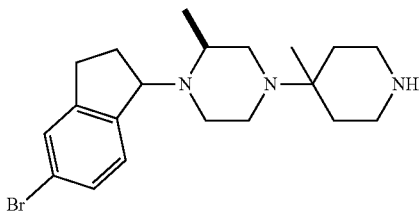 [SMILES: C[C@H]1CN(C2(C)CCNCC2)CCN1C1CCc2cc(Br)ccc21]

Step F (2S)-1-(5-Bromo-2,3-dihydro-1H-inden-1-yl)-2-methyl-4-(4-methylpiperidin-4-yl)piperazine The intermediate obtained from step E (0.23 g) was dissolved in a solution of 4 N HCl in dioxane (3 mL). After being stirred at room temperature for 2 h, the solution was concentrated to provide the title compound as a trihydrochloride salt (0.23 g). MS calculated for $C_{20}H_{30}BrN_3$: $(M+H)^+$392; found 392.2, 394.2.

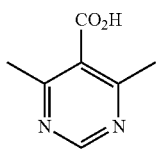

Step G 4,6-Dimethylpyrimidine-5-carboxylic acid.

Ethyl 2-Acetyl-3-ethoxybut-2-enoate. A 5 L 4-neck flask equipped with a mechanical stirrer, condenser, thermowell, addition funnel and $N_2$ inlet was charged with ethyl acetoacetate (493.1 g, 483 mL, 3.7931 mol, 1.0 equiv) and sodium ethoxide (3.1 g, 0.046 mol, 1.2 mol %). Ketene diethylacetal (880.0 g, 1000 mL, 7.5862 mol, 2.0 equiv) was added over 1 hr maintaining the reaction temperature at <22° C. by external cooling. When addition was complete, the reaction mixture was heated at 85° C.±5° C. for 7.5 hr. The yellow brown reaction mixture was cooled to room temperature and stirred overnight. Much of the lower boiling components [EtOH, EtOAc, Me(OEt)$_3$] were stripped on a roto-evaporator (bath temperature ~65° C.). The residual yellow-orange oil was distilled, collecting the fraction with bp 100-107° C. (1.8-2.1 Torr) to give 675.2 g (89%) of product as a yellow liquid.

Ethyl 4,6-Dimethylpyrimidine-5-carboxylate. Ethyl 2-acetyl-3-ethoxybut-2-enoate (10.7 g, 0.0537 mol), formamidine acetate (5.6 g, 0.054 mol) and sodium ethoxide (2.7 M in ethanol, 20.0 mL) were mixed in ethanol (30 mL) and the mixture was stirred at 90° C. for 4 h. The reaction mixture was cooled, quenched with water and concentrated. The crude material was purified by flash chromatography on silica gel, eluting with 10%, 50% ethyl acetate/hexane to afford the desired product (7.4 g, 76%) as a yellow oil. MS (EI) 181.1 (M+1). $^1$H NMR (300 MHz, CDCl$_3$) δ (ppm) 8.97 (s, 1H), 4.44 (q, 2H), 2.56 (s, 6H), 1.42 (t, 3H).

4,6-Dimethyl-pyrimidine-5-carboxylic acid. Ethyl 4,6-dimethylpyrimidine-5-carboxylate (10.9 g, 0.0605 mol) was mixed with a solution of sodium hydroxide (4.0 g, 0.10 mol) in water (70 mL). The mixture was stirred at room temperature overnight. The aqueous reaction was acidified using concentrated hydrochloric acid, and then concentrated to dryness. To this residue, acetone (100 mL) was added. The insoluble sodium chloride was filtered out and washed with methanol (100 mL). The filtrate was concentrated to dryness. The residue was washed with ACN to give 8.5 g (92%) of product as a solid. MS (EI) 153.1 (M+1). $^1$H NMR (400 MHz, CD$_3$OD) δ (ppm) 8.89 (s, 1H), 2.56 (s, 6H).

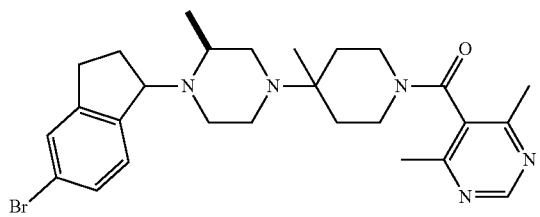 [SMILES: Cc1ncnc(C)c1C(=O)N1CCC(C)(N2CCN(C3CCc4cc(Br)ccc43)[C@@H](C)C2)CC1]

Step H 5-({4-[(3S)-4-(5-Bromo-2,3-dihydro-1H-inden-1-yl)-3-methylpiperazin-1-yl]-4-methylpiperidin-1-yl}carbonyl)-4,6-dimethylpyrimidine To a solution of (2S)-1-(5-bromo-2,3-dihydro-1H-inden-1-yl)-2-methyl-4-(4-methylpiperidin-4-yl)piperazine trihydrochloride (30 mg, 0.06 mmol) and 4,6-dimethyl-pyrimidine-5-carboxylic acid (9 mg, 0.06 mmol) in DMF (2 mL) was added benzotriazol-1-yloxytris(dimethylamino)phosphonium hexafluorophosphate (30 mg, 0.06 mmol) followed by triethylamine (30 mg, 0.3 mmol). After being stirred at room temperature for 5 h, the mixture was diluted with EtOAc and a solution of Na$_2$CO$_3$ in water. The organic layer was separated, washed with water several times, dried over Na$_2$SO$_4$ and concentrated. Purification on reverse phase HPLC and lyophilization gave the final product as a TFA salt (20 mg). MS calculated for $C_{27}H_{36}BrN_5O$: $(M+H)^+$526; found 526.1, 528.1.

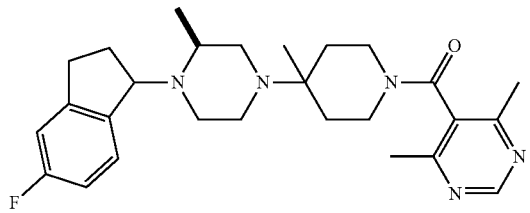 [SMILES: Cc1ncnc(C)c1C(=O)N1CCC(C)(N2CCN(C3CCc4cc(F)ccc43)[C@@H](C)C2)CC1]

Example 2

5-({4-[(3S)-4-(5-Fluoro-2,3-dihydro-1H-inden-1-yl)-3-methylpiperazin-1-yl]-4-methylpiperidin-1-yl}carbonyl)-4,6-dimethylpyrimidine This compound was prepared substantially as described in Example 1 using appropriate starting materials. MS calculated for $C_{27}H_{36}FN_5O$: $(M+H)^+$466; found 466.2.

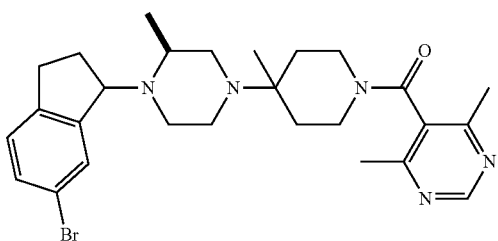 [SMILES: Cc1ncnc(C)c1C(=O)N1CCC(C)(N2CCN(C3CCc4ccc(Br)cc43)[C@@H](C)C2)CC1]
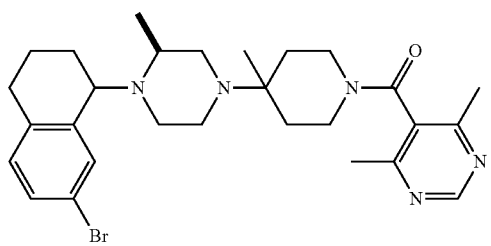 [SMILES: Cc1ncnc(C)c1C(=O)N1CCC(C)(N2CCN(C3CCCc4ccc(Br)cc43)[C@@H](C)C2)CC1]

Example 3

5-({4-[(3S)-4-(6-Bromo-2,3-dihydro-1H-inden-1-yl)-3-methylpiperazin-1-yl]-4-methylpiperidin-1-yl}carbonyl)-4,6-dimethylpyrimidine This compound was prepared substantially as described in Example 1 using appropriate starting materials. MS calculated for $C_{27}H_{36}BrN_5O$: $(M+H)^+$526; found 526.1, 528.1.

Example 6

5-({4-[(3S)-4-(7-Bromo-1,2,3,4-tetrahydronaphthalen-1-yl)-3-methylpiperazin-1-yl]-4-methylpiperidin-1-yl}carbonyl)-4,6-dimethylpyrimidine This compound was prepared substantially as described in Example 1 using appropriate starting materials. MS calculated for $C_{28}H_{38}BrN_5O$: $(M+H)^+$540; found 540.2, 542.1.

Example 7

4,6-Dimethyl-5-[(4-methyl-4-{(3S)-3-methyl-4-[6-(trifluoromethyl)-2,3-dihydro-1H-inden-1-yl]piperazin-1-yl}piperidin-1-yl)carbonyl]pyrimidine

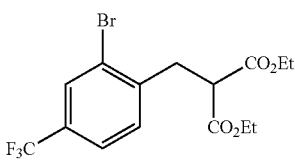 [SMILES: CCOC(=O)C(Cc1ccc(C(F)(F)F)cc1Br)C(=O)OCC]

Step A

Diethyl[2-bromo-4-(trifluoromethyl)benzyl]malonate

Into a suspension of sodium hydride (1.4 g, 58 mmol) in DMF (37 mL) at 10° C. was dropwise added ethyl malonate (14 g, 88 mmol). After addition the mixture was stirred for 1 hr at room temperature. To it was slowly added a solution of 2-bromo-1-(chloromethyl)-4-(trifluoromethyl)benzene (10.0 g, 36.6 mmol) in DMF (20 mL). After being stirred at room temperature overnight, the mixture was poured into ice water (300 mL). The resulting solution was extracted twice with ether. The combined extracts were washed with water and brine, dried over $MgSO_4$ and concentrated. Column chromatography on silica (5-10% EtOAc in hexane) afforded the title compound as an oil (13.5 g, 93%). MS calculated for $C_{15}H_{16}BrF_3O_4$: $(M+H)^+$397; found 397.0, 399.0.

Example 4

5-({4-[(3S)-4-(6-Fluoro-2,3-dihydro-1H-inden-1-yl)-3-methylpiperazin-1-yl]-4-methylpiperidin-1-yl}carbonyl)-4,6-dimethylpyrimidine This compound was prepared substantially as described in Example 1 using appropriate starting materials. MS calculated for $C_{27}H_{36}FN_5O$: $(M+H)^+$466; found 466.2.

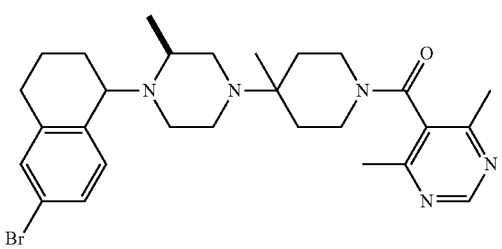

Example 5

5-({4-[(3S)-4-(6-Bromo-1,2,3,4-tetrahydronaphthalen-1-yl)-3-methylpiperazin-1-yl]-4-methylpiperidin-1-yl}carbonyl)-4,6-dimethylpyrimidine This compound was prepared substantially as described in Example 1 using appropriate starting materials. MS calculated for $C_{28}H_{38}BrN_5O$: $(M+H)^+$540; found 540.2, 542.1.

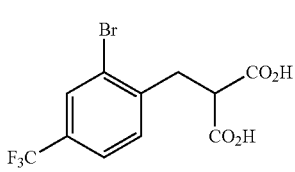

Step B

2-Bromo-4-(trifluoromethyl)benzyl]malonic acid

To a solution of diethyl[2-bromo-4-(trifluoromethyl)benzyl]malonate (13.5 g, 34 mmol) in ethanol (60 mL) and water (28 mL) was added a 5 M solution of sodium hydroxide in water (20 mL). After being stirred at room temperature overnight, ethanol was removed in vacuo. The water solution was diluted by addition of more water and extracted with ether twice. The resulting water layer was acidified to pH=3 with concentrated HCl and extracted with ether 3 times. The combined ether layers were washed with water and brine, dried over $MgSO_4$ and concentrated to give the title compound as a white solid (9.8 g, 84%). MS calculated for $C_{11}H_8BrF_3O_4$: $(M+H)^+341$; found 363 $(M+Na)^+$.

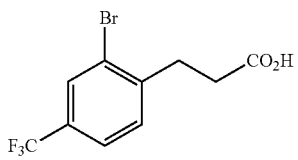 [SMILES: O=C(O)CCc1ccc(C(F)(F)F)cc1Br]

Step C

3-[2-Bromo-4-(trifluoromethyl)phenyl]propanoic acid

[2-Bromo-4-(trifluoromethyl)benzyl]malonic acid (9.80 g, 28.7 mmol) in a round-bottom flask was heated to 180° C. and heating was continued at 180° C. for 1.5 hrs. After cooling to room temperature, the solid was dissolved in ether. The resulting solution was dried over $MgSO_4$ and concentrated. The solid was washed with hexane to give the title compound (7.20 g, 85%). MS calculated for $C_{10}H_8BrF_3O_2$: $(M+H)^+297$; found 297.0, 299.0.

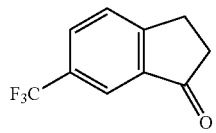 [SMILES: O=C1CCc2ccc(C(F)(F)F)cc21]

Step D

6-(Trifluoromethyl)indan-1-one

To a solution of 3-[2-bromo-4-(trifluoromethyl)phenyl]propanoic acid (6.40 g, 21.5 mmol) in THF (300 mL) and hexane (80 mL) at −78° C. was added a 2.5 M solution of n-butyllithium in hexane (19 mL). After being stirred for 15 min, the mixture was poured into a 2 N HCl solution (150 mL). The two layers were separated and the water layer was extracted by ether. The combined organic layers were washed with $NaHCO_3$ solution, water, brine, dried over $MgSO_4$ and concentrated. Column chromatography on silica (10-20% EtOAC in hexane) provided the title compound (2.2 g, 51%) as an oil. MS calculated for $C_{10}H_7F_3O$: $(M+H)^+201$; found 201.0.

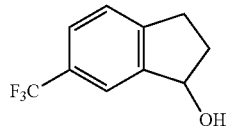 [SMILES: OC1CCc2ccc(C(F)(F)F)cc21]

Step E

6-(Trifluoromethyl)indan-1-ol

To a solution of 6-(trifluoromethyl)indan-1-one (2.20 g, 11 mmol) in THF (30 mL) was added sodium borohydride (0.50 g, 13 mmol). After being stirred for 30 min, methanol (10 mL) was added slowly. Stirring was continued for 2 hrs. The reaction was quenched by addition of an aqueous ammonium chloride solution. The two layers were separated and the water layer was extracted by ether. The combined organic layers were washed with water, brine, dried over $MgSO_4$ and concentrated. Column chromatography on silica (10-15% EtOAC in hexane) gave the title compound (1.52 g, 68%) as an oil. MS calculated for $C_{10}H_9F_3O$: $(M+H)^+203$; found 185.0 $(M-H_2O+1)^+$.

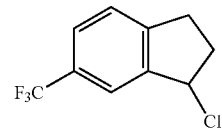 [SMILES: FC(F)(F)c1ccc2c(c1)C(Cl)CC2]

Step F

1-Chloro-6-(trifluoromethyl)indane 6-(Trifluoromethyl)indan-1-ol (1.52 g, 7.5 mmol) was dissolved in thionyl chloride (15 mL). After being stirred at room temperature for 2 hrs, the solution was concentrated in vacuo to provide the title compound (1.5 g, 90%).

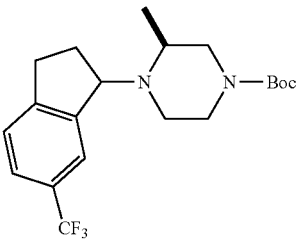 [SMILES: C[C@H]1CN(C(=O)OC(C)(C)C)CCN1C1CCc2ccc(C(F)(F)F)cc21]

Step G tert-Butyl (3S)-3-Methyl-4-[6-(trifluoromethyl)-2,3-dihydro-1H-inden-1-yl]piperazine-1-carboxylate A solution of 1-chloro-6-(trifluoromethyl)indane (1.52 g, 6.89 mmol), tert-butyl (3S)-3-methylpiperazine-1-carboxylate (2.1 g, 10 mmol), sodium iodide (3 g, 20 mmol) and triethylamine (3 g, 30 mmol) in DMF (20 mL) was stirred at 60° C. overnight. After cooling to room temperature, water was added. The resulting solution was extracted with EtOAc twice. The combined extracts were washed with water and brine, dried over $MgSO_4$ and concentrated. Column chromatography on silica (10%-30% EtOAc in hexane) afforded two isomers. Isomer 1: 0.52 g (brown oil). MS calculated for $C_{20}H_{27}F_3N_2O_2$: (M+H)$^+$385; found 385.2. Isomer 2: 0.41 g (brown oil). MS: (M+H)$^+$385.2

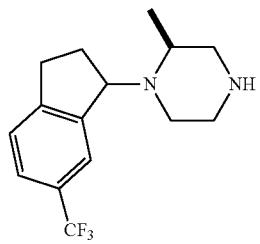 [SMILES: C[C@H]1CNCCN1C1CCc2ccc(C(F)(F)F)cc21]

Step H

(2S)-2-Methyl-1-[6-(trifluoromethyl)-2,3-dihydro-1H-inden-1-yl]piperazine tert-Butyl (3S)-3-methyl-4-[6-(trifluoromethyl)-2,3-dihydro-1H-inden-1-yl]-piperazine-1-carboxylate (isomer 1 from step G, 0.52 g, 1.4 mmol) was dissolved in a 4 M solution of HCl in 1,4-dioxane (10 mL). After being stirred at room temperature for 2 hrs, the solution was concentrated in vacuo to provide the title compound as a dihydrochloride salt (0.48 g, 100%). MS calculated for $C_{15}H_{19}F_3N_2$: (M+H)$^+$285; found 285.1.

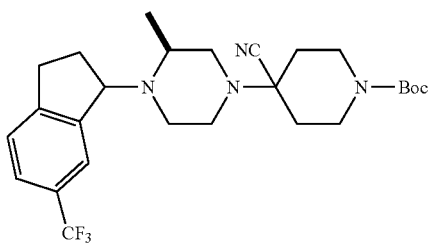 [SMILES: C[C@H]1CN(C2(C#N)CCN(C(=O)OC(C)(C)C)CC2)CCN1C1CCc2ccc(C(F)(F)F)cc21]

Step I tert-Butyl 4-Cyano-4-{(3S)-3-methyl-4-[6-(trifluoromethyl)-2,3-dihydro-1H-inden-1-yl]piperazin-1-yl}piperidine-1-carboxylate (2S)-2-Methyl-1-[6-(trifluoromethyl)-2,3-dihydro-1H-inden-1-yl]piperazine dihydrochloride (0.38 g, 1.3 mmol) was dissolved in dichloromethane. The solution was washed with saturated NaHCO$_3$ solution, dried over MgSO$_4$ and concentrated. The residue was taken up in dichloromethane (20 mL). To it were added tert-butyl 4-oxo-1-piperidinecarboxylate (0.32 g, 1.6 mmol) and titanium tetraisopropoxide (0.8 g, 3 mmol). The mixture was stirred at room temperature overnight and concentrated in vacuo. The residue was taken up in THF (20 mL). Diethylaluminum cyanide (0.18 g, 1.6 mmol) was added. After being stirred at room temperature for 5 hrs, the solution was quenched by addition of water (3 mL). The resulting solution was filtered through Celite and the Celite was washed with dichloromethane several times. The filtrate was dried over MgSO$_4$ and concentrated to give the title compound (0.72 g, 98%) as a brown viscous oil. MS calculated for $C_{26}H_{35}F_3N_4O_2$: (M+H)$^+$493; found 493.2.

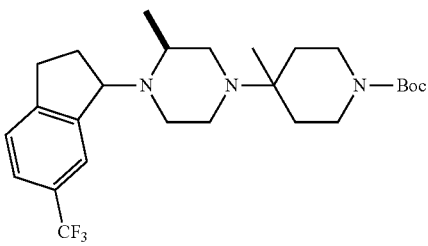 [SMILES: C[C@H]1CN(C2(C)CCN(C(=O)OC(C)(C)C)CC2)CCN1C1CCc2ccc(C(F)(F)F)cc21]

Step J tert-Butyl 4-Methyl-4-{(3S)-3-methyl-4-[6-(trifluoromethyl)-2,3-dihydro-1H-inden-1-yl]piperazin-1-yl}piperidine-1-carboxylate To a solution of tert-butyl 4-cyano-4-{(3S)-3-methyl-4-[6-(trifluoromethyl)-2,3-dihydro-1H-inden-1-yl]piperazin-1-yl}piperidine-1-carboxylate (0.72 g, 1.3 mmol) in THF (20 mL) was added a 3 M solution of methylmagnesium bromide in ether (4.0 mL). After being stirred at room temperature overnight, the reaction was quenched by addition of water. The resulting solution was extracted with EtOAc twice. The combined EtOAc layers were dried and concentrated. Column chromatography on silica (20-30% EtOAc in hexane) provided the title compound (0.32 g, 50%) as a viscous oil. MS calculated for $C_{26}H_{38}F_3N_3O_2$: (M+H)$^+$482; found 482.3.

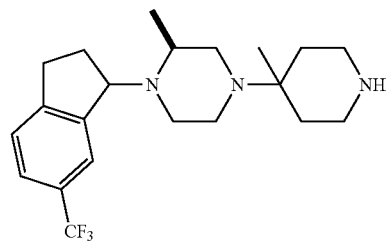 [SMILES: C[C@H]1CN(C2(C)CCNCC2)CCN1C1CCc2ccc(C(F)(F)F)cc21]

Step K

(2S)-2-Methyl-4-(4-methylpiperidin-4-yl)-1-[6-(trifluoromethyl)-2,3-dihydro-1H-inden-1-yl]piperazine tert-Butyl 4-methyl-4-{(3S)-3-methyl-4-[6-(trifluoromethyl)-2,3-dihydro-1H-inden-1-yl]piperazin-1-yl}piperidine-1-carboxylate (0.32 g, 0.6 mmol) was dissolved in a 4 M solution of HCl in dioxane (8.0 mL). After being stirred at room temperature for 2 hrs, the solution was concentrated to give the title compound (0.35 g) as a trihydrochloride salt. MS calculated for $C_{21}H_{30}F_3N_3$: (M+H)$^+$382; found 382.2.

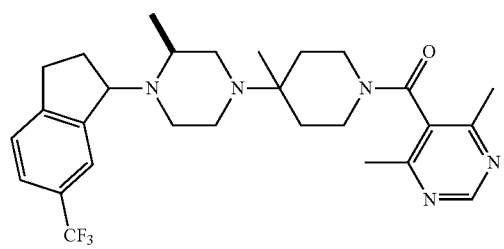 [SMILES: Cc1ncnc(C)c1C(=O)N1CCC(C)(N2CCN(C3CCc4ccc(C(F)(F)F)cc43)[C@@H](C)C2)CC1]

Step L 4,6-Dimethyl-5-[(4-methyl-4-{(3S)-3-methyl-4-[6-(trifluoromethyl)-2,3-dihydro-1H-inden-1-yl]piperazin-1-yl}piperidin-1-yl)carbonyl]pyrimidine To a solution of (2S)-2-methyl-4-(4-methylpiperidin-4-yl)-1-[6-(trifluoromethyl)-2,3-dihydro-1H-inden-1-yl]piperazine trihydrochloride (100 mg, 0.183 mmol), 4,6-dimethyl-pyrimidine-5-carboxylic acid (67 mg, 0.22 mmol) in DMF (5 mL) was added benzotriazol-1-yloxytris(dimethylamino)phosphonium hexafluorophosphate (97 mg, 0.22 mmol) followed by triethylamine (90 mg, 0.9 mmol). After being stirred at room temperature overnight, a solution of NaHCO$_3$ in water was added. The resulting solution was extracted with EtOAc twice. The combined EtOAc layers were washed with brine, dried over MgSO$_4$ and concentrated. Column chromatography on silica (10-20% MeOH in EtOAc) afforded the title compound (60 mg) as an oil. MS calculated for C$_{28}$H$_{36}$F$_3$N$_5$O: (M+H)$^+$516; found 516.2.

Example 8

4,6-Dimethyl-5-[(4-methyl-4-{(3S)-3-methyl-4-[5-(trifluoromethyl)-2,3-dihydro-1H-inden-1-yl]piperazin-1-yl}piperidin-1-yl)carbonyl]pyrimidine

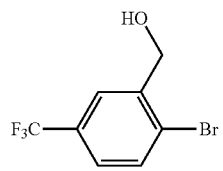

Step A

[2-Bromo-5-(trifluoromethyl)phenyl]methanol

To a solution of 2-bromo-5-(trifluoromethyl)benzonitrile (10.0 g, 40 mmol) in dichloromethane (100 mL) was dropwise added a 1.0 M solution of diisobutylaluminum hydride in hexane (48 mL). The resulting solution was stirred under nitrogen at ambient temperature for 1 h and was then diluted by addition of ether (100 mL). After cooling in an ice bath, a 3 N solution of HCl was carefully added, and the mixture was vigorously stirred at ambient temperature for 15 min. The organic layer was washed with brine, dried (MgSO$_4$) and evaporated. The resulting oil was purified by flash chromatography (5% EtOAc/hexane) affording 5 g of 2-bromo-5-trifluoromethylbenzaldehyde. $^1$H NMR (CDCl$_3$) δ 10.39 (s, 1H), 8.18 (d, J=2 Hz, 1H), 7.82 (d, J=8.8 Hz, 1H), 7.70 (dd, J=8.5 Hz, 2 Hz, 1H).

To a mixture of 2-bromo-5-(trifluoromethyl)benzaldehyde (5 g, 20 mmol) in THF (20 mL) at 0° C. was added sodium borohydride (0.8 g, 20 mmol). The resulting mixture was stirred at 0° C. to ambient temperature for 1 h. The reaction was quenched by addition of an aqueous solution of NaHCO$_3$. The resulting solution was extracted with EtOAc twice. The combined extracts were washed with brine, dried (MgSO$_4$), filtered and concentrated to give the desired alcohol as a white solid (4.4 g). $^1$H NMR (CDCl$_3$) δ 7.81 (s, 1H), 7.66 (d, J=8.3 Hz, 1H), 7.42 (dd, J=8.3 Hz, 2.0 Hz, 1H), 4.81 (d, J=6.3 Hz, 2H), 2.03 (m, 1H).

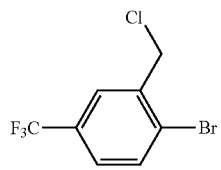

Step B

1-Bromo-2-(chloromethyl)-4-(trifluoromethyl)benzene

To [2-bromo-5-(trifluoromethyl)phenyl]methanol (4.4 g, 17 mmol) was added thionyl chloride (5 mL) and the resulting mixture was stirred at room temperature for 1 h. Evaporation in vacuo gave the crude product as an oil. $^1$H NMR (CDCl$_3$) δ 7.77 (d, J=8.3 Hz, 1H), 7.73 (d, J=2.0 Hz, 1H), 7.53 (dd, J=8.5, 2.2 Hz, 1H), 5.66 (d, J=12.7 Hz, 1H), 5.46 (d, J=12.2 Hz).

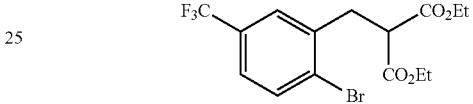

Step C

Diethyl[2-Bromo-5-(trifluoromethyl)benzyl]malonate

To a solution of ethyl malonate (23 g, 140 mmol) in DMF (70 mL) at 0° C. was added sodium hydride (3.9 g, 60% in mineral oil, 97 mmol), and the resulting mixture was stirred at ambient temperature for 30 min. To the mixture was added a solution of 1-bromo-2-(chloromethyl)-4-(trifluoromethyl)benzene (16 g, 60 mmol) in DMF (20 mL). The reaction mixture was stirred at room temperature for 3 h and quenched with ice water. The resulting solution was extracted with EtOAc twice. The extracts were washed with brine, dried (MgSO$_4$), filtered and concentrated. The crude material was purified by flash chromatography on silica eluting with 3% then 5% EtOAc/hexane to afford the desired product (15.2 g, 64%) as an oil. LC/MS calculated for C$_{15}$H$_{16}$BrF$_3$O$_4$: (M+H)$^+$397; found 397.1/399.1.

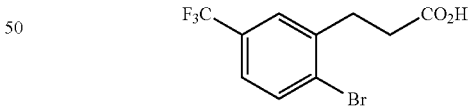

Step D

3-[2-Bromo-5-(trifluoromethyl)phenyl]propanoic acid

To a solution of diethyl[2-bromo-5-(trifluoromethyl)benzyl]malonate (22.9 g, 57.6 mmol) in ethanol (100 mL) and water (50 mL) was added a 5 M solution of sodium hydroxide in water (30 mL). The mixture was heated to reflux for 2 h. Ethanol was removed by evaporation. The aqueous layer was extracted with ether and then acidified with concentrated HCl to pH 5 at which time a lot of white solid precipitated out. The solid was collected by filtration. The filtrate was extracted with ethyl acetate twice, and the extracts were washed with brine, dried (MgSO$_4$) and concentrated to give a white solid.

The combined solid was decarboxylated by heating in an oil bath to 180° C. for about 1 h. The resulting yellow oil was cooled and pumped in vacuo to afford the desired mono-acid (11.5 g, 67%). LC/MS calculated for C$_{10}$H$_8$BrF$_3$O$_2$: (M+H)$^+$ 297; found 297.1/299.1.

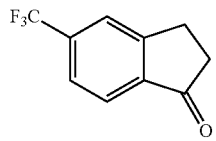

Step E 5-(Trifluoromethyl)indan-1-one

To a solution of 3-[2-bromo-5-(trifluoromethyl)phenyl] propanoic acid (2.8 g, 9.4 mmol) in THF (100 mL) and hexane (20 mL) at −78° C. was dropwise added a 2.5 M solution of n-butyllithium in hexane (8.3 mL). After the addition had been completed, the reaction was quenched with saturated NH$_4$Cl. The resulting solution was extracted with ethyl acetate twice. The extracts were washed with saturated NaHCO$_3$, brine, dried over MgSO$_4$ and concentrated. The crude material was purified by flash chromatography on silica eluting with 10-20% EtOAc/hexane to afford the desired product as a white solid (0.7 g, 37%). LC/MS calculated for C$_{10}$H$_7$F$_3$O: (M+H)$^+$201; found 201.1.

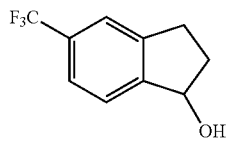 [SMILES: OC1CCc2cc(C(F)(F)F)ccc21]

Step F 5-(Trifluoromethyl)indan-1-ol

To a solution of 5-(trifluoromethyl)indan-1-one (0.7 g, 3 mmol) in THF (5 mL) cooled in an ice bath was added sodium borohydride (0.1 g, 3 mmol) followed by MeOH (1 mL). After being stirred for 30 min, the reaction was quenched with aqueous NaHCO$_3$. The resulting solution was extracted with EtOAc twice. The extracts were washed with brine, dried (MgSO$_4$), filtered and concentrated. The crude material was purified by flash chromatography on silica eluting with 20% EtOAc/hexane to afford the desired product (0.65 g, 92%) as an oil. LC/MS calculated for C$_{10}$H$_9$F$_3$O: (M+H)$^+$203; found 185.1 (M+H—H$_2$O)$^+$.

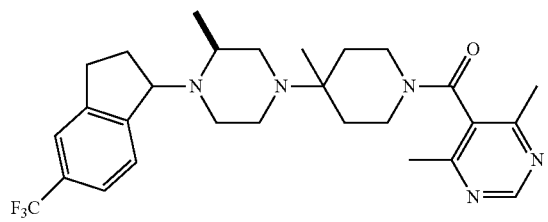 [SMILES: Cc1ncnc(C)c1C(=O)N1CCC(C)(N2CCN(C3CCc4cc(C(F)(F)F)ccc43)[C@@H](C)C2)CC1]

Step G 4,6-Dimethyl-5-[(4-methyl-4-{(3S)-3-methyl-4-[5-(trifluoromethyl)-2,3-dihydro-1H-inden-1-yl]piperazin-1-yl}piperidin-1-yl)carbonyl]pyrimidine Starting from 5-(trifluoromethyl)indan-1-ol, the title compound was prepared following the procedures described for Example 7. MS calculated for C$_{28}$H$_{36}$F$_3$N$_5$O: (M+H)$^+$516; found 516.2.

Example 9

1-((2S)-4-{1-[(4,6-Dimethylpyrimidin-5-yl)carbonyl]-4-methylpiperidin-4-yl}-2-methylpiperazin-1-yl)-5-(trifluoromethyl)indan-2-ol

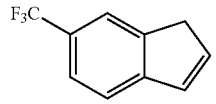 [SMILES: FC(F)(F)c1ccc2c(c1)CC=C2]

Step A 6-(Trifluoromethyl)-1H-indene

A mixture of 5-(trifluoromethyl)indan-1-ol (1.6 g, 7.9 mmol) and p-toluenesulfonic acid (0.02 g, 0.1 mmol) in toluene (20 mL) was refluxed through a Dean-Stark trap for about 3 h. The solution was concentrated in vacuo and the residue was purified by flash chromatography on silica eluting with 5% EtOAc/hexane to afford the desired product as an oil (1.4 g, 96%).

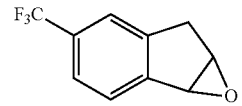

Step B 4-(Trifluoromethyl)-6,6a-dihydro-1aH-indeno[1,2-b]oxirene

To a solution of 6-(trifluoromethyl)-1H-indene (1.1 g, 6 mmol) in anhydrous dichloromethane (80 mL) at −78° C. was added a 5.5 M solution of tert-butyl hydroperoxide in n-decane (1.3 mL) followed by titanium tetrachloride (0.79 mL, 7.2 mmol). After being stirred at −78° C. for 1 h, the resulting brown solution was quenched with a mixture of Et$_2$O/saturated Na$_2$SO$_3$ solution. The mixture was stirred at ambient temperature for 1 h to give a colorless solution. The organic layer was separated and washed with brine, dried over MgSO$_4$ and concentrated to give the crude product (1.2 g) as a solid. LC/MS calculated for C$_{10}$H$_7$F$_3$O: (M+H)$^+$201; found 201.0.

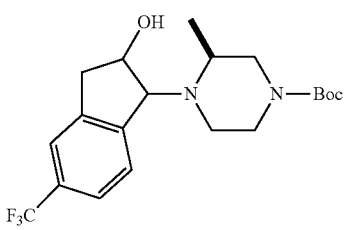 [SMILES: C[C@H]1CN(C(=O)OC(C)(C)C)CCN1C1c2ccc(C(F)(F)F)cc2CC1O]

Step C tert-Butyl (3S)-4-[2-Hydroxy-5-(trifluoromethyl)-2,3-dihydro-1H-inden-1-yl]-3-methylpiperazine-1-carboxylate A mixture of 4-(trifluoromethyl)-6,6a-dihydro-1aH-indeno[1,2-b]oxirene (1.2 g, 6.0 mmol) and tert-butyl (3S)-3-methylpiperazine-1-carboxylate (1.4 g, 7.2 mol) in ethanol (20 mL) was refluxed overnight. Another gram of tert-butyl (3S)-3-methylpiperazine-1-carboxylate was added. The mixture was transferred into a sealed flask and heated to 95° C. for 2 days. The solvent was concentrated and the residue was purified by flash chromatography eluting with 25% EtOAc/hexane, followed by 5% MeOH/EtOAc+0.5% concentrated NH$_4$OH. Two isomers were isolated. Isomer 1 (fast moving isomer): 0.45 g; MS calculated for the C$_{20}$H$_{27}$F$_3$N$_2$O$_3$ (M+H)$^+$401; found 401.1. Isomer 2 (slow moving isomer): 0.38 g; MS found 401.1.

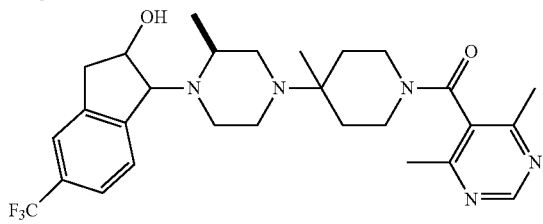 [SMILES: Cc1ncnc(C)c1C(=O)N1CCC(C)(N2CCN(C3c4ccc(C(F)(F)F)cc4CC3O)[C@@H](C)C2)CC1]

Step D 1-((2S)-4-{1-[(4,6-Dimethylpyrimidin-5-yl)carbonyl]-4-methylpiperidin-4-yl}-2-methylpiperazin-1-yl)-5-(trifluoromethyl)indan-2-ol Starting from tert-butyl (3S)-4-[2-hydroxy-5-(trifluoromethyl)-2,3-dihydro-1H-inden-1-yl]-3-methylpiperazine-1-carboxylate (isomer 1 from step C), the title compound was prepared using procedures similar to those described in Example 7. MS calculated for C$_{28}$H$_{36}$F$_3$N$_5$O$_2$: (M+H)$^+$532; found 532.

Example 10

5-[(4-{(3S)-4-[2-Methoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine

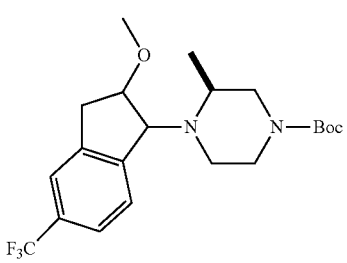 [SMILES: COC1Cc2cc(C(F)(F)F)ccc2C1N1CCN(C(=O)OC(C)(C)C)C[C@@H]1C]

Step A tert-Butyl (3S)-4-[2-Methoxy-5-(trifluoromethyl)-2,3-dihydro-1H-inden-1-yl]-3-methylpiperazine-1-carboxylate To a solution of tert-butyl (3S)-4-[2-hydroxy-5-(trifluoromethyl)-2,3-dihydro-1H-inden-1-yl]-3-methylpiperazine-1-carboxylate (isomer 1 from step C in Example 9) (50 mg, 0.1 mmol) in THF (2 mL) at 0° C. was added NaH (8 mg, 60% in oil, 0.2 mmol). After being stirred for 10 min, MeI (28 mg, 0.2 mmol) was added. The mixture was stirred at ambient temperature for 1 h and quenched with aqueous NH$_4$Cl. The resulting solution was extracted with EtOAc twice. The extracts were washed with brine, dried (MgSO$_4$), filtered and concentrated to give the crude product. LC/MS calculated for C$_{21}$H$_{29}$F$_3$N$_2$O$_3$: (M+H)$^+$415. found 415.2.

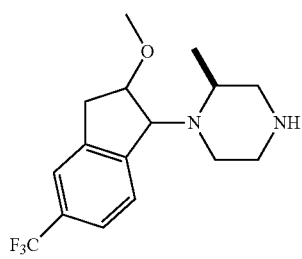 [SMILES: COC1Cc2cc(C(F)(F)F)ccc2C1N1CCNC[C@@H]1C]

Step B (2S)-1-[2-Methoxy-5-(trifluoromethyl)-2,3-dihydro-1H-inden-1-yl]-2-methylpiperazine To tert-butyl (3S)-4-[2-methoxy-5-(trifluoromethyl)-2,3-dihydro-1H-inden-1-yl]-3-methylpiperazine-1-carboxylate (51.8 mg, 0.125 mmol) was added a 4.0 M solution of hydrogen chloride in dioxane (2 mL). The mixture was stirred at room temperature for 1 h and concentrated in vacuo to give the title compound as a dihydrochloride salt. LC/MS calculated for C$_{16}$H$_{22}$ClF$_3$N$_2$O: (M+H)$^+$351; found 351.1.

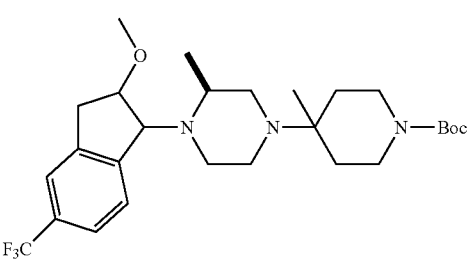 [SMILES: COC1Cc2cc(C(F)(F)F)ccc2C1N1CCN(C2(C)CCN(C(=O)OC(C)(C)C)CC2)C[C@@H]1C]

Step C tert-Butyl 4-{(3S)-4-[2-Methoxy-5-(trifluoromethyl)-2,3-dihydro-1H-inden-1-yl]-3-methylpiperazin-1-yl}-4-methylpiperidine-1-carboxylate To a mixture of (2S)-1-[2-methoxy-5-(trifluoromethyl)-2,3-dihydro-1H-inden-1-yl]-2-methylpiperazine hydrochloride (44 mg, 0.12 mmol) and tert-butyl 4-oxo-1-piperidinecarboxylate (25 mg, 0.12 mmol) in methylene chloride (2 mL) was added triethylamine (0.07 mL, 0.5 mmol), followed by titanium tetraisopropoxide (0.037 mL, 0.12 mmol). The resulting mixture was stirred at room temperature overnight and concentrated to provide the crude enamine.

The crude enamine was dissolved in THF and treated with 1.0 M of diethylaluminum cyanide in toluene (0.15 mL). The mixture was stirred at room temperature overnight and quenched by addition of aqueous NaHCO$_3$ and EtOAc. The resulting solution was filtered through Celite. The filtrate was separated and the organic layer was washed with brine, dried (MgSO$_4$), filtered and concentrated to give the crude cyano compound. LC/MS: 523.2 (M+H)$^+$.

The crude cyano compound was dissolved in THF and treated with a 3.0 M solution of methylmagnesium bromide in ether (0.2 mL) at 0° C. The mixture was stirred at room temperature for 4 h. Another 0.2 mL of methylmagnesium bromide solution was added and the mixture was stirred at room temperature for two days. The reaction was quenched with aqueous NaHCO$_3$ and extracted with EtOAc twice. The extracts were washed with brine, dried (MgSO$_4$), filtered and concentrated. The crude material was purified by flash chromatography on silica eluting with 25% then 50% EtOAc/hexane to give the title compound (25 mg). MS calculated for C$_{27}$H$_{40}$F$_3$N$_3$O$_3$: (M+H)$^+$512; found 512.2.

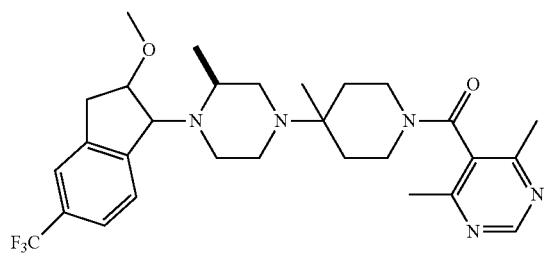 [SMILES: COC1Cc2cc(C(F)(F)F)ccc2C1N1CCN(C2(C)CCN(C(=O)c3c(C)ncnc3C)CC2)C[C@@H]1C]

Step D

5-[(4-{(3S)-4-[2-Methoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine To tert-butyl 4-{(3S)-4-[2-methoxy-5-(trifluoromethyl)-2,3-dihydro-1H-inden-1-yl]-3-methylpiperazin-1-yl}-4-methylpiperidine-1-carboxylate (0.02 g, 0.04 mmol) was added a 4.0 M solution of HCl in 1,4-dioxane (2.0 mL). The resulting mixture was stirred at room temperature for 1 h, concentrated and pumped in vacuo to dryness.

To the above amine hydrochloride was added DMF (2.0 mL), 4,6-dimethyl-pyrimidine-5-carboxylic acid (0.01 g, 0.08 mmol), benzotriazol-1-yloxytris(dimethylamino)phosphonium hexafluorophosphate (0.026 g, 0.059 mmol) and triethylamine (0.02 mL, 0.1 mmol). After being stirred at room temperature overnight, the reaction was quenched with aqueous NaHCO$_3$ and extracted with EtOAc twice. The extracts were washed with brine, dried (MgSO$_4$), filtered and concentrated. The crude material was purified by reverse phase HPLC (10-80% acetonitrile-water with 0.05% TFA, 30 min, 10 ml/min) to give the title compound (25 mg) as a bis-TFA salt. LC/MS calculated for C$_{29}$H$_{38}$F$_3$N$_5$O$_2$: (M+H)$^+$ 546; found 546.2.

Example 11

5-[(4-(3S)-4-[(1R,2R)-2-Ethoxy-5-(trifluoromethyl)-2,3-dihydro-1H-inden-1-yl]-3-methylpiperazin-1-yl-4-methylpiperidin-1-yl)carbonyl]-4,6-dimethylpyrimidine dihydrochloride

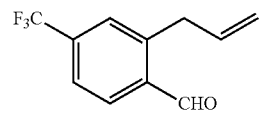

Step A

2-Allyl-4-(trifluoromethyl)benzaldehyde

To a oven dried 5 L 4-neck round bottom flask fitted with overhead stirring, nitrogen needle, 500 mL addition funnel, 250 mL addition funnel and thermometer, tetrahydrofuran (1400 mL) and N,N,N'-trimethylethane-1,2-diamine (105 mL, 0.788 mol) were added. The solution was cooled to −40° C. (dry ice/MeCN bath). n-Butyllithium (1.6 M in hexane, 510 mL) was added to the 500 mL addition funnel and then added to the above solution over 40 minutes (−40 to −35° C.). The colorless solution became light yellow in color. The cold bath was then removed and the reaction mixture was stirred for 30 minutes while being warmed to a temperature of −10° C. The reaction was cooled to −40 to −45° C. and p-trifluoromethylbenzaldehyde (77 mL, 0.56 mol) was added via a syringe to the 250 mL addition funnel. The aldehyde was added dropwise over 15 minutes while reaction temperature was maintained at −40 to −35° C. The reaction became brown in color over the course of the addition. The reaction was stirred at −50 to −40° C. for 30 minutes. The second addition of 1.6 M of n-butyllithium in hexane (400 mL) was carried out over 50 minutes via addition funnel. The reaction mixture was allowed to warm to −25° C. and was maintained at −20 to −30° C. for 3 hours before copper(I) bromide (108 g, 0.738 mol) was added directly via a powder funnel The cold bath was removed and the reaction was allowed to warm and stirred for additional 90 minutes. The reaction was cooled to −30 to −25° C. and a solution of allyl bromide (78 mL, 0.90 mol) in tetrahydrofuran (240 mL) was added dropwise over 40 minutes through the 250 mL addition funnel in portions. After being stirred for 2 h, the reaction was quenched by the addition of methanol (100.0 mL). The cold bath was removed and the mixture was stirred for 5 minutes before 6.00 M of hydrochloric acid solution (300.0 mL) was added (pH=~7). After the mixture was stirred for additional 15 minutes, it was passed through a celite pad, and the celite pad was rinsed with ether. Saturated ammonium chloride (400 mL) was added and the organic phase was collected. Aqueous phase was further extracted with 300 mL ether. The combined organic phase was washed with 400 ml saturated ammonium chloride (400 mL), 1 M sodium bicarbonate (3×400 mL) and brine (400 mL), and dried over magnesium sulfate. After the removal of the drying agent by filtration, the filtrate was concentrated on rotovap to give a brown liquid. Further purification was carried out by distillation to give 105.4 g (85%) of product. $^1$H NMR (400 MHz, CDCl$_3$) δ (ppm) 10.22 (s, 1H), 8.02 (d, 1H), 7.80 (d, 1H), 7.74 (s, 1H), 6.02 (m, 1H), 5.06 (m, 1H), 4.96 (m, 1H), 3.89 (d, 2H).

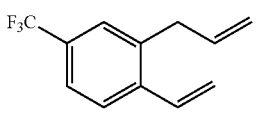

Step B

2-Allyl-4-(trifluoromethyl)-1-vinylbenzene

Triphenylmethylphosphonium bromide (182 g, 0.508 mol) was suspended in diethyl ether (900 mL, 8 mol) and cooled to 0° C. n-Butyllithium (1.60 M in hexane, 289 mL) was added rapidly through a syringe and the resulting mixture warmed to room temperature and stirred overnight (18 h). The stirring was stopped to allow the solids to settle and the top clear solution was transferred via a cannula to a solution of 2-allyl-4-(trifluoromethyl)benzaldehyde (99.0 g, 0.462 mol) in methylene chloride (900 mL), which was being stirred at 0° C. Following the addition, the ice bath was removed and the mixture was heated to reflux for approx. 30 h. After cooling to room temperature, the orange solution was concentrated until a small amount of solvent was present. Silica gel was added to the stirred solution until a thick slurry was obtained. Pentane (500 mL) was added and more solid crashed out. The mixture was plugged through silica gel in a glass fritted vacuum funnel using pentane (1.5 L). The pentane solution was collected into a 3 L round bottom flask. The nearly colorless liquid was then concentrated to give pure diene (78 g, 79.3%); $^1$H NMR (400 MHz, CDCl$_3$) δ (ppm) 7.58 (d, 1H), 7.45 (d, 1H), 7.41 (s, 1H), 6.95 (dd, 1H), 5.95 (m, 1H), 5.72 (d, 1H), 5.41 (d, 1H), 5.11 (d, 1H), 5.00 (d, 1H), 3.48 (d, 2H).

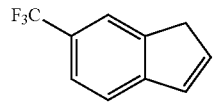

Step C 6-(Trifluoromethyl)-1H-indene

Methylene chloride (0.6 L) was added to a 1 L flask containing 2-allyl-4-(trifluoromethyl)-1-vinylbenzene (80.0 g, 0.377 mol). Bis(tricyclohexylphosphine)benzylidine ruthenium(IV) dichloride (Grubbs catalyst, 1st generation) (3.1 g, 0.0038 mol) was added to the solution and the resulting solution was refluxed overnight (18 h). The solvent was evaporated to give a dark oil, which was passed through a silica gel plug using pentane. After pentane was carefully removed, 57 g (82.8%) of pure product was collected as slight brown oil. $^1$H NMR (400 MHz, CDCl$_3$) δ (ppm) 7.72 (s, 1H), 7.55 (d, 1H), 7.48 (d, 1H), 6.93 (m, 1H), 6.74 (m, 1H), 3.46 (brs, 1H).

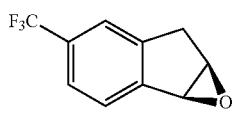

Step D 4-(Trifluoromethyl)-6,6a-dihydro-1aH-indeno[1,2-b]oxirene

To a solution of 2 M sodium hypochlorite in water (200 mL) at 0° C. was added aqueous sodium hydroxide (1 M, 40 mL), 4-(3-phenylpropyl)pyridine N-oxide (6.0 g, 0.03 mol) and a solution of (S,S)-(+)-N,N'-bis(3,5-di-tert-butylsalicylidene)-1,2-cyclohexanediamino-manganese(III) chloride (4.13 g, 0.00651 mol) in dichloromethane (700 mL). The resulting brown solution was allowed to be stirred for 15 min at 0° C. To the cold solution, a solution of 6-(trifluoromethyl)-1H-indene (51 g, 0.24 mol) in dichloromethane (700 mL) was added with simultaneous addition of aqueous sodium hypochlorite (2 M, 200 mL). The reaction was kept at 0° C. and the brown solution remained the same color upon addition of the indene. After 4 h, the organic phase was collected and dried over sodium sulfate. The mixture was plugged through silica gel using pentane. After removal of the solvent, 42 g (88%, 84% ee) of epoxide was obtained. $^1$H NMR (400 MHz, CDCl$_3$) δ (ppm) 7.72 (s, 1H), 7.55 (d, 1H), 7.48 (d, 1H), 6.93 (m, 1H), 6.74 (m, 1H), 3.46 (brs, 1H).

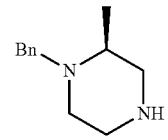

Step E (2S)-1-Benzyl-2-methylpiperazine tert-Butyl (3S)-3-methylpiperazine-1-carboxylate (380.0 g, 1.897 mol) and benzyl bromide (248 mL, 2.09 mol) were mixed in acetonitrile (440 mL). Triethylamine (300.0 mL, 2.152 mol) was carefully added and the mixture was refluxed overnight. After the mixture was cooled down to room temperature, the solid was filtered out. The filtrate was concentrated. The residue was combined with the solid and dissolved in methylene chloride. The methylene chloride solution was washed with 1N NaOH and dried over magnesium sulfate. After the solvent was removed, the residue was directly treated with 6 N HCl at 0° C., and 3 hours later, the solution was basified by slowly adding solid sodium hydroxide. The resulting mixture was extracted with methylene chloride and the extracts were dried over magnesium sulfate. After removal of the solvent, 330 g (91.4%) of product was obtained. The product was used directly for next step. $^1$H NMR (400 MHz, CDCl$_3$) δ (ppm) 7.30 (m, 5H), 4.05 (d, 1H), 3.15 (d, 1H), 2.92 (m, 1H), 2.83 (m, 2H), 2.67 (m, 1H), 2.60 (m, 1H), 2.38 (m, 1H), 2.36 (bs, 2H), 2.06 (m, 1H), 1.14 (d, 3H). MS (EI) 191.1 (M+1).

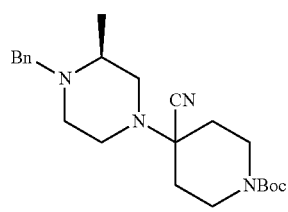 [SMILES: C[C@H]1CN(C2(C#N)CCN(C(=O)OC(C)(C)C)CC2)CCN1Cc1ccccc1]

Step F t-Butyl 4-[(3S)-4-Benzyl-3-methylpiperazin-1-yl]-4-cyanopiperidine-1-carboxylate In a 5 L flask, (2S)-1-benzyl-2-methylpiperazine (260.0 g, 1.366 mol), dichloromethane (1000 mL), t-butyl 4-oxo-1-piperidinecarboxylate (272 g, 1.37 mol) and titanium tetraisopropoxide (480.0 mL, 1.626 mol) were mixed and the mixture was stirred at room temperature for 20 h. The mixture was cooled down to 0° C. and diethylaluminum cyanide in toluene (1.0 M, 1600 mL) was added dropwise. The resulting mixture was stirred at room temperature for 20 h. The reaction content was then split into two 5 L flasks, To each flask, 1 L of ethyl acetate, 500 g of sodium bicarbonate, 150 g of celite were added before they were cooled down to −40° C. using dry ice/acetonitrile. To each flask, 200 mL of saturated aqueous sodium sulfate was then slowly added with vigorous stirring. After the reaction mixture was slowly warmed up to room temperature and stirred for 4 hours, 1 L of methanol was added to each flask. After being stirred overnight, the reaction mixture was filtered through a thin layer of sand. The cake was taken back into a 5 L flask and stirred with 3 L of methanol for 5 hours, and insoluble solid was filtered off. The combined filtrates were concentrated to dryness, and 3 L of methylene chloride was added. Insoluble solid was filtered off. The filtrate was dried with magnesium sulfate, the solvent was removed to give 484 g (88.9%) of product as a slight yellow solid. The crude product was essentially pure and used directly for next step. $^1$H NMR (400 MHz, CDCl$_3$) δ (ppm) 7.32 (m, 5H), 4.04 (d, 1H), 3.95 (brs, 2H), 3.15 (d, 1H), 3.15 (brs, 2H), 2.82 (m, 1H), 2.73 (m, 2H), 2.44 (m, 2H), 2.25 (t, 1H), 2.15 (m, 1H), 2.05 (m, 1H), 1.66 (m, 1H), 1.46 (s, 9H), 1.17 (d, 3H); MS (EI) 399.2 (M+1).

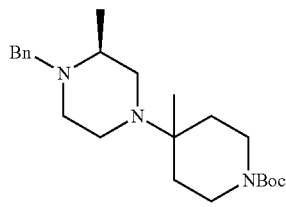 [SMILES: C[C@H]1CN(C2(C)CCN(C(=O)OC(C)(C)C)CC2)CCN1Cc1ccccc1]

Step G t-Butyl 4-[(3S)-4-Benzyl-3-methylpiperazin-1-yl]-4-methylpiperidine-1-carboxylate A solution of tert-butyl 4-[(3S)-4-benzyl-3-methylpiperazin-1-yl]-4-cyanopiperidine-1-carboxylate (242 g, 0.605 mol) in tetrahydrofuran (1.5 L) in a 5 L flask was cooled down to −40° C. using dry ice/acetonitrile. Methylmagnesium bromide (3.0 M in tetrahydrofuran, 800 mL) was slowly added. After the addition, the reaction mixture was slowly warmed up to room temperature and stirred overnight. After cooling down to −40° C. using dry ice/acetonitrile, celite (200 g), and then ethyl acetate (500 mL) were carefully added. After the addition, the mixture was stirred for 4 hours while the temperature slowly rose to room temperature. The reaction mixture was cooled back down to −40° C. again, and water (200 mL), and then methanol (1.5 L) were added. After being stirred at room temperature overnight, the mixture was filtered through a thin layer of sand. The cake was taken back into a 5 L flask and stirred with methanol (2 L) for 5 hours. Insoluble solid was filtered off. The combined filtrates were concentrated to dryness. Methylene chloride (3.5 L) was added. Insoluble solid was filtered off. The filtrate was dried with magnesium sulfate. After the solvent was removed, 436 g (92.6%) of product was obtained as a white sticky solid. The crude product was essentially pure and used directly for next step. MS (EI) 388.3 (M+1).

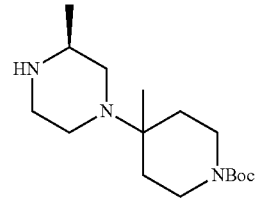

Step H t-Butyl 4-Methyl-4-[(3S)-3-methylpiperazin-1-yl]piperidine-1-carboxylate

A solution of t-butyl 4-[(3S)-4-benzyl-3-methylpiperazin-1-yl]-4-methylpiperidine-1-carboxylate (45.5 g, 0.118 mol) in methanol (320 mL) and acetic acid (35 mL, ~5 equiv) in a 2.25 L Parr bottle was charged with H$_2$ to 60 psi and the mixture shaken for 18 hr. The reaction mixture was filtered through a pad of Celite and the pad was washed with methanol. The filtrate was concentrated under vacuum. The residual oil was dissolved in DCM (500 mL) and washed with aqueous sodium hydroxide (300 mL). The aqueous phase was back-extracted with methylene chloride (200 mL). The combined organic solution was washed with brine (500 mL), dried with sodium sulfate and the solvent was removed under vacuum to give 35 g (100%) of product as a pale yellow viscous oil that slowly crystallized. $^1$H NMR (400 MHz, CDCl$_3$) δ (ppm) 3.44 (m, 2H), 3.36 (m, 2H), 2.97 (dt, 1H), 2.84 (dd, 1H), 2.78 (m, 1H), 2.71 (brd, 2H), 2.16 (dt, 1H), 1.81 (t, 2H), 1.76 (m, 1H), 1.45 (s, 9H), 1.34 (m, 3H), 1.03 (d, 3H), 0.90 (s, 3H); MS (EI) 298.2 (M+1).

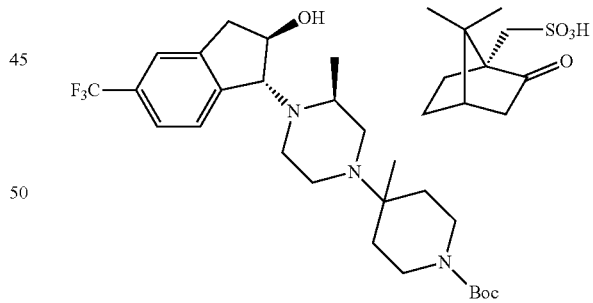

Step I t-Butyl 4-(3S)-4-[(1R,2R)-2-hydroxy-5-(trifluoromethyl)-2,3-dihydro-1H-inden-1-yl]-3-methylpiperazin-1-yl-4-methylpiperidine-1-carboxylate[(1R)-7,7-Dimethyl-2-oxobicyclo[2.2.1]hept-1-yl]methanesulfonic acid salt A mixture of (1aS,6 aR)-4-(trifluoromethyl)-6,6a-dihydro-1aH-indeno[1,2-b]oxirene (118.4 g, 0.5917 mol) and t-butyl 4-methyl-4-[(3S)-3-methylpiperazin-1-yl]piperidine-1-carboxylate (160.00 g, 0.53793 mol) in ethanol (100 mL)

was heated at 70° C. (oil bath temperature) over two days. The mixture was concentrated, and the residue was passed through a silica plug using ethyl acetate containing 1% triethylamine. After the removal of the solvent, 267.67 g of foamy solid was obtained. To this solid, acetonitrile (500 mL) was added and the mixture was stirred for 30 min. To the above mixture, solid [(1R)-7,7-dimethyl-2-oxobicyclo[2.2.1]hept-1-yl]methanesulfonic acid (124.96 g, 0.53793 mol) was added at once. The solution was slowly turned clear, then white solid started crashing out. After overnight stirring, the solid was collected by filtration and washed with acetonitrile and dried to give 232 g of product. The filtrate was neutralized and concentrated, and on the residue a similar salt formation process was performed to give additional 74 g of product. The combined yield was 70%. MS (EI) 498.2 (M+1).

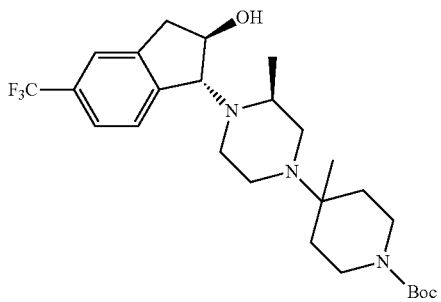

Step J t-Butyl 4-(3S)-4-[(1R,2R)-2-Hydroxy-5-(trifluoromethyl)-2,3-dihydro-1H-inden-1-yl]-3-methylpiperazin-1-yl-4-methylpiperidine-1-carboxylate tert-Butyl 4-(3S)-4-[(1R,2R)-2-hydroxy-5-(trifluoromethyl)-2,3-dihydro-1H-inden-1-yl]-3-methylpiperazin-1-yl-4-methylpiperidine-1-carboxylate[(1R)-7,7-dimethyl-2-oxobicyclo[2.2.1]hept-1-yl]methanesulfonic acid salt (512 g, 0.701 mol) was dissolved in 1 M aqueous sodium hydroxide (1 L), and the solution was extracted with methylene chloride (2×2 L). The combined organic layers were dried over magnesium sulfate and concentrated. The residue was further dried under high vacuum to give off-white foamy solid (346 g. 99.1%). MS (EI) 498.2 (M+1).

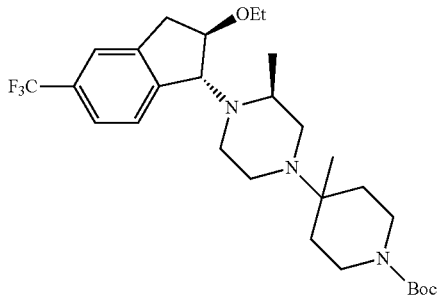 [SMILES: C[C@H]1CN(C2(C)CCN(C(=O)OC(C)(C)C)CC2)CCN1[C@@H]1c2ccc(C(F)(F)F)cc2C[C@H]1O]

Step K t-Butyl 4-(3S)-4-[2-Ethoxy-5-(trifluoromethyl)-2,3-dihydro-1H-inden-1-yl]-3-methylpiperazin-1-yl-4-methylpiperidine-1-carboxylate Sodium hydride (5.225 g, 0.1306 mol) was mixed with dry DMF (150 mL) at 0° C. A solution of t-butyl 4-(3S)-4-[2-hydroxy-5-(trifluoromethyl)-2,3-dihydro-1H-inden-1-yl]-3-methylpiperazin-1-yl-4-methylpiperidine-1-carboxylate (50.0 g, 0.1005 mol) in DMF (100 mL) was added dropwise at 0° C. over 20 min. After the addition, the mixture was stirred for another 20 min before iodoethane (12.06 mL, 0.1507 mol) was added at one portion. After being stirred for 1 h, the reaction content was carefully poured into 500 mL icy water. The mixture was extracted with methylene chloride (500 mL×3). The combined organic layer was washed with brine, and dried over magnesium sulfate. After the removal of the solvent, the residue was dissolved in methylene chloride, and passed through a silica plug with ethyl acetate/hexane/triethylamine 50:50:1 (the plug was presaturated with the same solvent system). After removal of the solvent, 48.4 g (91.6%) of product was obtained as a sticky solid, MS (EI) 526.2 (M+1).

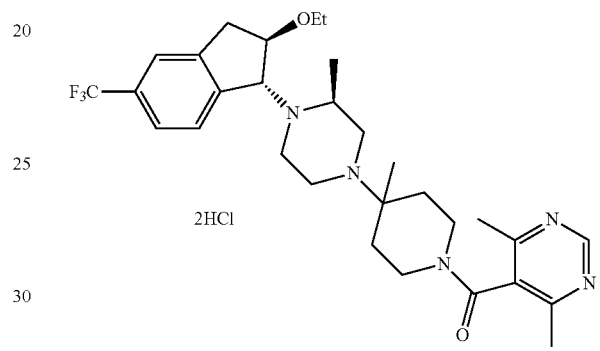

Step L

5-[(4-(3S)-4-[(1R,2R)-2-Ethoxy-5-(trifluoromethyl)-2,3-dihydro-1H-inden-1-yl]-3-methylpiperazin-1-yl-4-methylpiperidin-1-yl)carbonyl]-4,6-dimethylpyrimidine dihydrochloride t-Butyl 4-(3S)-4-[2-ethoxy-5-(trifluoromethyl)-2,3-dihydro-1H-inden-1-yl]-3-methylpiperazin-1-yl-4-methylpiperidine-1-carboxylate (48.4 g, 0.0921 mol) was treated with a 4.0 M solution of hydrogen chloride in 1,4-dioxane (230 mL) at room temperature for 1 h. The reaction mixture was concentrated to dryness and the residue was further dried under high vacuum. The formed amine hydrochloride was mixed with 4,6-dimethyl-pyrimidine-5-carboxylic acid (16.8 g, 0.110 mol) in methylene chloride (100 mL), and then 1-hydroxybenzotriazole (16.80 g, 0.1243 mol), N-(3-dimethylaminopropyl)-N'-ethylcarbodiimide hydrochloride (25.00 g, 0.1304 mol) and triethylamine (65.0 mL, 0.466 mol) were added. The resulting reaction mixture was stirred at room temperature overnight before it was diluted with methylene chloride and washed with aqueous sodium hydroxide (1 M) and brine. The organic layer was collected and dried over magnesium sulfate. After removal of the solvent, the residue was dissolved in methylene chloride (50 mL) and the solution was passed through a silica plug with ethyl acetate containing 1% triethylamine. The solution was concentrated and the residue was dissolved in 900 mL of isopropyl acetate. To the above solution, 185 mL of 1.0 N HCl in isopropyl acetate was slowly added. The mixture slowly turned cloudy, and was stirred overnight. The formed white solid was collected, washed with 40 mL of isopropyl acetate. The cake was air-dried to give 47.0 g (80.7%) of product. MS (EI) 560.3 (M+1).

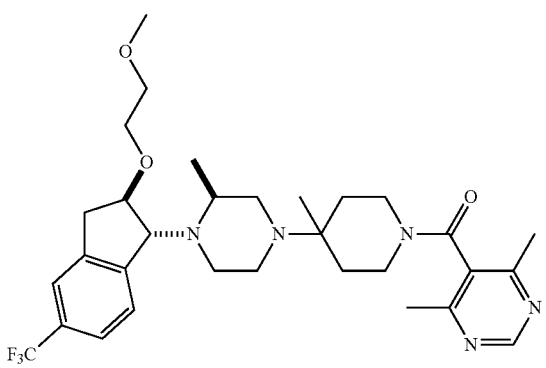

Example 12

5-[(4-{(3S)-4-[(1R,2R)-2-(2-Methoxyethoxy)-5-(trifluoromethyl)-2,3-dihydro-1H-inden-1-yl]-3-methylpiperazin-1-yl}-4-methylpiperidin-1-yl)carbonyl]-4,6-dimethylpyrimidine This compound was prepared substantially as described in Example 11 using appropriate starting materials. MS (M+H)+ 590.

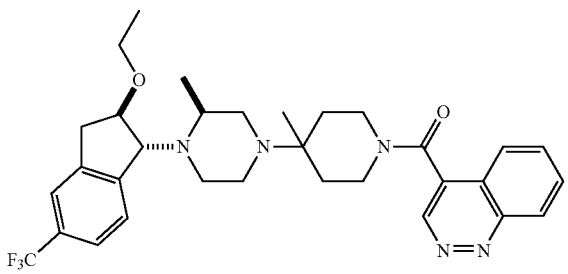

Example 13

4-[(4-{(3S)-4-[(1S,2R)-2-Ethoxy-5-(trifluoromethyl)-2,3-dihydro-1H-inden-1-yl]-3-methylpiperazin-1-yl}-4-methylpiperidin-1-yl)carbonyl]cinnoline This compound was prepared substantially as described in Example 11 using appropriate starting materials. MS (M+H)+ 582.4.

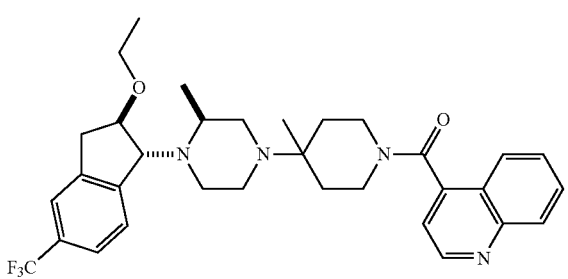

Example 14

4-[(4-{(3S)-4-[(1R,2R)-2-Ethoxy-5-(trifluoromethyl)-2,3-dihydro-1H-inden-1-yl]-3-methylpiperazin-1-yl}-4-methylpiperidin-1-yl)carbonyl]quinoline This compound was prepared substantially as described in Example 11 using appropriate starting materials. MS (M+H)+ 581.4.

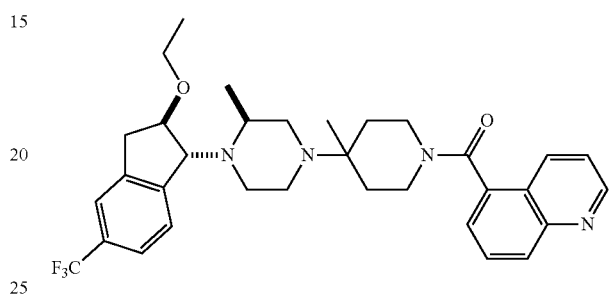

Example 15

5-[(4-{(3S)-4-[(1R,2R)-2-Ethoxy-5-(trifluoromethyl)-2,3-dihydro-1H-inden-1-yl]-3-methylpiperazin-1-yl}-4-methylpiperidin-1-yl)carbonyl]quinoline This compound was prepared substantially as described in Example 11 using appropriate starting materials. MS (M+H)+ 581.4.

Example 16

4-[(4-{(3S)-4-[(1R,2R)-2-Ethoxy-5-(trifluoromethyl)-2,3-dihydro-1H-inden-1-yl]-3-methylpiperazin-1-yl}-4-methylpiperidin-1-yl)carbonyl]-1,8-naphthyridine This compound was prepared substantially as described in Example 11 using appropriate starting materials. MS (M+H)+ 582.4.

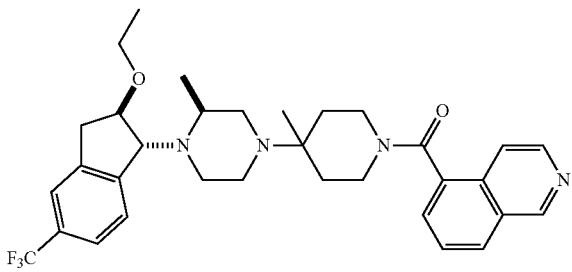

Example 17

5-[(4-{(3S)-4-[(1R,2R)-2-Ethoxy-5-(trifluoromethyl)-2,3-dihydro-1H-inden-1-yl]-3-methylpiperazin-1-yl}-4-methylpiperidin-1-yl)carbonyl]isoquinoline This compound was prepared substantially as described in Example 11 using appropriate starting materials. MS (M+H)+ 581.4.

Example 18

5-[(4-{(3S)-4-[(1R,2R)-5-Bromo-2-ethoxy-2,3-dihydro-1H-inden-1-yl]-3-methylpiperazin-1-yl}-4-methylpiperidin-1-yl)carbonyl]-4,6-dimethylpyrimidine

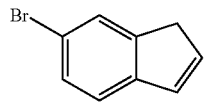

Step A

6-Bromo-1H-indene

A solution of 5-bromoindan-1-ol (5.00 g, 23.5 mmol) and p-Toluenesulfonic acid monohydrate (100 mg, 0.5 mmol) in benzene (150.00 mL) was heated to reflux for 2 h and water was continuously removed from the reaction mixture with a Dean-Stark trap. After cooling to room temperature, the benzene solution was washed with water, dried over anhydrous $Na_2SO_4$ and concentrated under reduced pressure. Purification of the residue by flash chromatography (hexane) yielded pure 5-bromoindene (4.0 g, 87%).

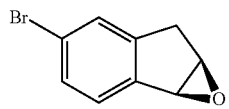 [SMILES: Brc1ccc2c(c1)C[C@H]1O[C@@H]21]

Step B

4-Bromo-6,6a-dihydro-1aH-indeno[1,2-b]oxirene

To a solution of 4-(3-phenylpropyl)pyridine N-oxide (68.88 mg, 0.323 mmol) in methylene chloride (6.00 mL) was added (S,S)-(+)-N,N'-bis(3,5-di-tert-butylsalicylidene)-1,2-cyclohexanediamino-manganese(III) chloride (58.62 mg, 0.09.23 mmol) and 2.0 M of sodium hypochlorite in water (4.00 mL) at 0° C. The resulting brown suspension was stirred at 0° C. for 15 min. To the cooled suspension was added a solution of 6-bromo-1H-indene (900 mg, 4.6141 mmol) in methylene chloride (6.00 mL) at 0° C. with simultaneous addition of 2.0 M of sodium hypochlorite in water (4.00 mL) at 0° C. The reaction was kept at 0° C. for 1 h. The reaction was allowed to warm up to room temperature and then stirred at room temperature overnight. The reaction mixture was poured into brine and then extracted with methylene chloride (4×40 mL). The combined extracts were dried over anhydrous $Na_2SO_4$, filtered and evaporated under reduced pressure. The crude product was used directly for the next reaction. The ratio of the two diastereomers was 8/1.

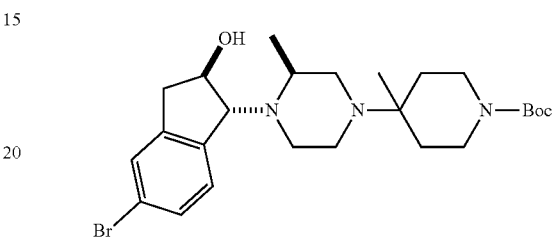

Step C tert-Butyl 4-{(3S)-4-[(1R,2R)-5-Bromo-2-hydroxy-2,3-dihydro-1H-inden-1-yl]-3-methylpiperazin-1-yl}-4-methylpiperidine-1-carboxylate To a solution of 4-bromo-6,6a-dihydro-1aH-indeno[1,2-b]oxirene (247.9 mg, 1.1746 mmol) in ethanol (10.00 mL) was added tert-butyl 4-methyl-4-[(3S)-3-methylpiperazin-1-yl]piperidine-1-carboxylate (349.36 mg, 1.1746 mmol). The reaction mixture was heated to reflux overnight. After cooling down, the mixture was evaporated under reduced pressure. Purification on silica gel with 50% ethyl acetate (1% $NH_4OH$) and hexane afforded the fast moving product as the desired compound (295 mg; 49.4%).

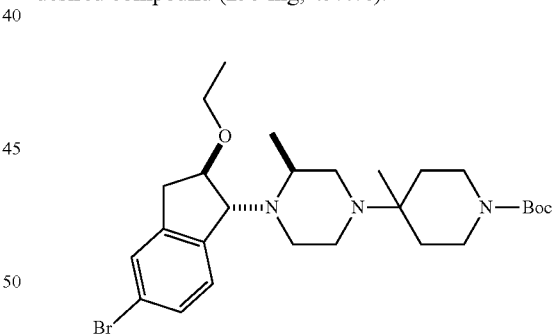

Step D tert-Butyl 4-{(3S)-4-[(1R,2R)-5-Bromo-2-ethoxy-2,3-dihydro-1H-inden-1-yl]-3-methylpiperazin-1-yl}-4-methylpiperidine-1-carboxylate To a solution of tert-butyl 4-{(3S)-4-[(1R,2R)-5-bromo-2-hydroxy-2,3-dihydro-1H-inden-1-yl]-3-methylpiperazin-1-yl}-4-methylpiperidine-1-carboxylate (564 mg, 1.1 mmol) in tetrahydrofuran (20.00 mL) was added sodium hydride (448 mg, 17.75 mmol) at room temperature. After stirring for 10 min, iodoethane (1.42 mL, 17.75 mmol) was added. The reaction mixture was stirred at room temperature overnight and quenched with saturated aqueous ammonium chloride solution (20 mL). The organic layer was separated and the aqueous phase was extracted with ethyl acetate (3×30 mL). The combined extracts were washed with brine, dried over anhydrous Na$_2$SO$_4$, filtered and evaporated under reduced pressure to afford the crude product (488 mg, 82%). LC-MS [M+1]=536.3, 538.8.

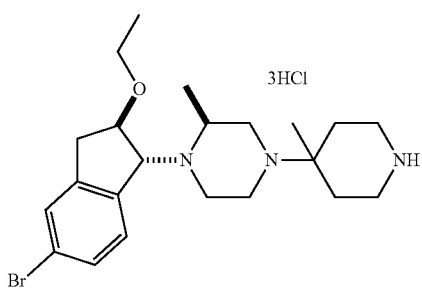

Step E (2S)-1-[(1R,2R)-5-Bromo-2-ethoxy-2,3-dihydro-1H-inden-1-yl]-2-methyl-4-(4-methylpiperidin-4-yl) piperazine Trihydrochloride To a solution of tert-butyl 4-{(3S)-4-[(1R,2R)-5-bromo-2-ethoxy-2,3-dihydro-1H-inden-1-yl]-3-methylpiperazin-1-yl}-4-methylpiperidine-1-carboxylate (50 mg, 0.093 mmol) in tetrahydrofuran (3 mL) was added a 4.00 M solution of hydrogen chloride in 1,4-dioxane (3 mL). The reaction mixture was stirred at room temperature for 1 h. Evaporation under reduced pressure afforded the desired de-Boc product.

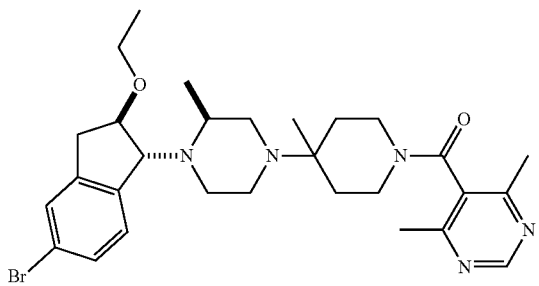

Step F

5-[(4-{(3S)-4-[(1S,2R)-5-Bromo-2-ethoxy-2,3-dihydro-1H-inden-1-yl]-3-methylpiperazin-1-yl}-4-methylpiperidin-1-yl)carbonyl]-4,6-dimethylpyrimidine To a slurry of (2S)-1-[(1R,2R)-5-bromo-2-ethoxy-2,3-dihydro-1H-inden-1-yl]-2-methyl-4-(4-methylpiperidin-4-yl) piperazine trihydrochloride (50 mg, 0.0916 mmol) in methylene chloride (6 mL) were added 4,6-dimethyl-pyrimidine-5-carboxylic acid (27.88 mg, 0.183 mmol), N-(3-dimethylaminopropyl)-N'-ethylcarbodiimide hydrochloride (21.07 mg, 0.11 mmol), 1-hydroxybenzotriazole (13.62 mg, 0.101 mmol) and triethylamine (0.0894 mL, 0.641 mmol). The reaction mixture was stirred at room temperature overnight. Direct chromatography on silica gel with 10% MeOH/EtOAc (1% NH$_4$OH) afforded the desired product (42 mg, 80%). LC-MS [M+1]=570.10; 572.05.

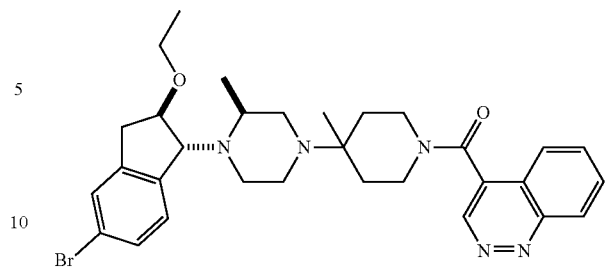

Example 19

4-[(4-{(3S)-4-[(1R,2R)-5-bromo-2-ethoxy-2,3-dihydro-1H-inden-1-yl]-3-methylpiperazin-1-yl}-4-methylpiperidin-1-yl)carbonyl]cinnoline This compound was prepared substantially as described in Example 18 using appropriate starting materials. MS (M+H)$^+$ 592.3, 594.3.

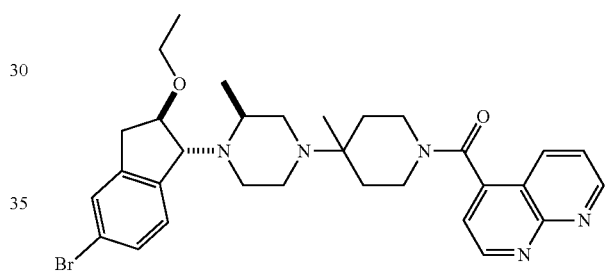

Example 20

4-[(4-{(3S)-4-[(1R,2R)-5-Bromo-2-ethoxy-2,3-dihydro-1H-inden-1-yl]-3-methylpiperazin-1-yl}-4-methylpiperidin-1-yl)carbonyl]-1,8-naphthyridine This compound was prepared substantially as described in Example 18 using appropriate starting materials. MS (M+H)$^+$ 592.3, 594.3.

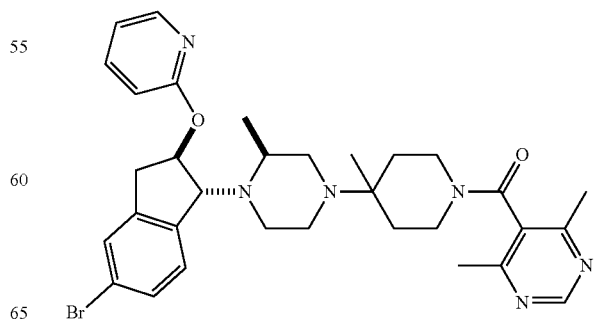

Example 21

5-[(4-{(3S)-4-[(1R,2R)-5-Bromo-2-(pyridin-2-yloxy)-2,3-dihydro-1H-inden-1-yl]-3-methylpiperazin-1-yl}-4-methylpiperidin-1-yl)carbonyl]-4,6-dimethylpyrimidine This compound was prepared substantially as described in Example 18 using appropriate starting materials. MS: (M+H)⁺619.3, 621.3.

Example 22

5-[(4-{(3S)-4-[(1R,2R)-2-Ethoxy-5-(1,3-thiazol-2-yl)-2,3-dihydro-1H-inden-1-yl]-3-methylpiperazin-1-yl}-4-methylpiperidin-1-yl)carbonyl]-4,6-dimethylpyrimidine

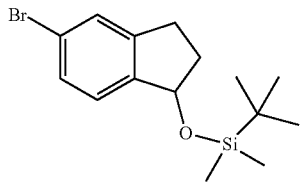 [SMILES: CC(C)(C)[Si](C)(C)OC1CCc2cc(Br)ccc21]

Step A

[(5-Bromo-2,3-dihydro-1H-inden-1-yl)oxy](tert-butyl)dimethylsilane

To a solution of 5-bromoindan-1-ol (4.00 g, 18.8 mmol) in N,N-dimethylformamide (25.00 mL) were added triethylamine (5.23 mL, 37.5 mmol), tert-butyldimethylsilyl chloride (4.244 g, 28.16 mmol) and 4-dimethylaminopyridine (115 mg, 0.939 mmol) at room temperature. The reaction mixture was stirred at room temperature for 3 h. The mixture was diluted with ether (100 mL) and quenched with water. The aqueous phase was extracted with ether (4×40 mL). The combined extracts were washed with brine, dried over anhydrous Na₂SO₄, filtered and evaporated under reduced pressure. Chromatography on silica gel with 5% EtOAc/hexane afforded the desired product (6.05 g, 98%).

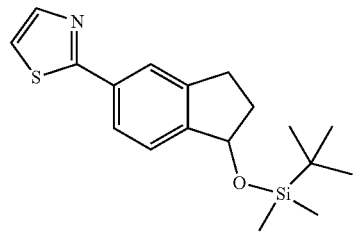 [SMILES: CC(C)(C)[Si](C)(C)OC1CCc2cc(-c3nccs3)ccc21]

Step B 2-(1-{[tert-Butyl(dimethyl)silyl]oxy}-2,3-dihydro-1H-inden-5-yl)-1,3-thiazole To a stirred suspension of zinc (899 mg, 13.75 mmol) in tetrahydrofuran (1.60 mL) was added 1,2-dibromoethane (0.118 mL, 1.37 mmol). The suspension was heated with a heat gun until no evolution of ethylene gas. Chlorotrimethylsilane (0.0698 mL, 0.55 mmol) and a solution of 2-bromothiazole (0.413 mL, 4.58 mmol) in tetrahydrofuran were added. After 15 min [(5-bromo-2,3-dihydro-1H-inden-1-yl)oxy](tert-butyl)dimethylsilane (1.0 g, 3.055 mmol) and tetrakis(triphenylphosphine)palladium(0) (70.6 mg, 0.0611 mmol) dissolved in tetrahydrofuran (8.00 mL) were added. The mixture was stirred for 24 h at reflux and quenched with 15 mL of brine. The organic layer was separated and the aqueous phase was extracted with methylene chloride (25 mL×3). The combined extracts were washed with brine, dried over anhydrous Na₂SO₄, and evaporated under reduced pressure. Chromatography on silica gel with 2.5% EtOAc/hexane afforded the desired coupling product (800 mg, 79%).

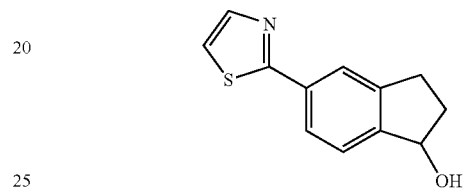

Step C 5-(1,3-Thiazol-2-yl)indan-1-ol

To a solution of 2-(1-{[tert-butyl(dimethyl)silyl]oxy}-2,3-dihydro-1H-inden-5-yl)-1,3-thiazole (630 mg, 1.9 mmol) in tetrahydrofuran (10.00 mL) was added a 1.00 M solution of tetrabutylammonium fluoride, trihydrate in tetrahydrofuran (1.90 mL) at 0° C. The ice bath was removed and the reaction mixture was stirred at room temperature for 1 h. The mixture was diluted with ether, washed with saturated NaCl aqueous solution, dried over anhydrous MgSO₄, filtered and evaporated under reduced pressure to afford the desired product (410 mg, 99%).

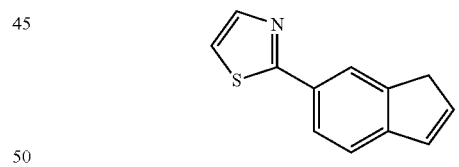

Step D 2-(1H-Inden-6-yl)-1,3-thiazole

To a solution of 5-(1,3-thiazol-2-yl)indan-1-ol (900.00 mg, 0.0041420 mol) in tetrahydrofuran (20.00 mL) was added a 1.0 M solution of hydrogen chloride in water (20.00 mL). The reaction mixture was heated to reflux overnight. After cooling down to room temperature, the reaction was quenched with 30 mL of 1 N NaOH aqueous solution. The organic layer was separated and the aqueous phase was extracted with EtOAc (3×30 mL). The combined extracts were washed with brine, dried over anhydrous MgSO₄, filtered, and evaporated under reduced pressure to afford the desired product (381 mg, 46%). LC-MS [M+1]=200.2.

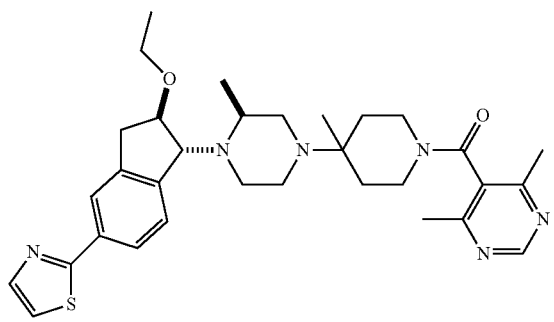

Step E

5-[(4-{(3S)-4-[(1R,2R)-2-Ethoxy-5-(1,3-thiazol-2-yl)-2,3-dihydro-1H-inden-1-yl]-3-methylpiperazin-1-yl}-4-methylpiperidin-1-yl)carbonyl]-4,6-dimethylpyrimidine Starting from the intermediate of step D, the title compound was prepared using procedures analogous to those described for Example 18. MS (M+H) 575.2.

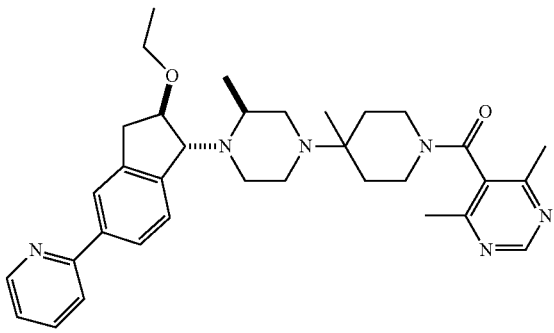

Example 23

5-[(4-{(3S)-4-[(1R,2R)-2-Ethoxy-5-pyridin-2-yl-2,3-dihydro-1H-inden-1-yl]-3-methylpiperazin-1-yl}-4-methylpiperidin-1-yl)carbonyl]-4,6-dimethylpyrimidine The title compound was prepared in a manner analogous to that for Example 22. MS (M+H) 569.3.

Example 24

5-[(4-{(3S)-4-[3-Methoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine

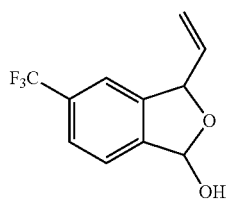

Step A 5-(Trifluormethyl)-3-vinyl-1,3-dihydro-2-benzofuran-1-ol

To a solution of N,N,N'-trimethyl-1,2-ethanediamine (4.76 mL, 37.4 mmol) in tetrahydrofuran (150.00 mL) was added a 1.6 M solution of n-butyllithium in hexane (25.7 mL) at −40° C. The colorless solution became light yellow. The cold bath was removed and the reaction stirred for 30 min while warming to −15° C. The reaction was rechilled at −40° C. and 4-trifluoromethylbenzaldehyde (5.00 mL, 37.4 mmol) was added. The reaction was stirred at −50° C. for 35 min before a second addition of a 1.60 M solution of n-butyllithium in hexane was carried out. The reaction was allowed to warm to −25° C. and maintained at −25° C. for 2 h at which time acrolein (2.75 mL, 41.2 mmol) was added. The reaction mixture was stirred overnight and quenched by addition of 30 mL of 6 N HCl aqueous solution. The organic layer was separated and the aqueous phase was extracted with EtOAc twice (2×30 mL). The combined extracts were washed with brine, dried over $Na_2SO_4$, evaporated in vacuo and purified by flash chromatography to give the desired product (2.4 g, 28% yield). LC-MS [M+1]=231.2.

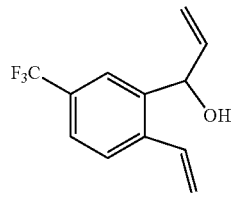 [SMILES: C=Cc1ccc(C(F)(F)F)cc1C(O)C=C]

Step B

1-[5-(Trifluoromethyl)-2-vinylphenyl]prop-2-en-1-ol

Triphenylmethylphosphonium bromide (1.71 g, 4.78 mmol) was dissolved in ether (20.00 mL). After cooling to 0° C., a 1.60 M solution of n-butyllithium in hexane (2.72 mL) was added rapidly by syringe and the resulting orange mixture was warmed to room temperature and stirred overnight. The stirring was stopped to allow the solids to settle and then the yield was transferred via cannula to a solution of 5-(trifluoromethyl)-3-vinyl-1,3-dihydro-2-benzofuran-1-ol (1.00 g, 4.34 mmol) in ether (10.00 mL) while stirring at 0° C. Following the addition, the ice bath was removed and the mixture was heated to reflux overnight. The reaction was allowed to cool and then the solids filtered off and washed with a small amount of ether. Most of the solvents were evaporated and the crude product was loaded onto silica gel and eluted with hexane/EtOAc (10:1) to give the desired product (0.81 g, 82%), LC-MS [M+1]=229.2.

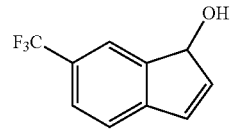

Step C 6-(Trifluoromethyl)-1H-inden-1-ol

To a solution of the 1-[5-(trifluoromethyl)-2-vinylphenyl]prop-2-en-1-ol (462 mg, 2.02 mmol) in methylene chloride (20 mL) under nitrogen was added benzylidene-bis(tricyclohexylphosphine)dichlororuthenium (70 mg, 0.08 mmol). The dark mixture was stirred at 25° C. for 30 min and concentrated. The residue was purified by flash chromatography to give the desired compound (278.1 mg, 68%). LC-MS [M+1]=279.2.

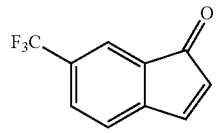

Step D 6-(Trifluoromethyl)-1H-inden-1-one

To a solution of pyridinium chlorochromate (1.08 g, 5.0 mmol) in methylene chloride (15 mL) was added dropwise a solution of 6-(trifluoromethyl)-1H-inden-1-ol (500 mg, 2.498 mmol) in methylene chloride (10 mL). After being stirred for 14 h, ether (30 mL) was added, and the reaction mixture was filtered through silica gel. The filtrate was concentrated in vacuo. The crude material was chromatographed (10:1 hexane/EtOAc) to afford 200 mg (40%) of the product. LC-MS [M+1]=199.2.

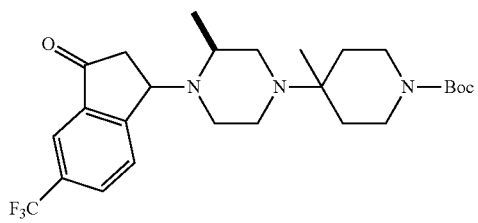 [SMILES: C[C@H]1CN(C2(C)CCN(C(=O)OC(C)(C)C)CC2)CCN1C1CC(=O)c2cc(C(F)(F)F)ccc21]

Step E tert-Butyl 4-Methyl-4-{3-methyl-4-[3-oxo-5-(trifluoromethyl)-2,3-dihydro-1H-inden-1-yl]piperazin-1-yl}piperidine-1-carboxylate A solution of 6-(trifluoromethyl)-1H-inden-1-one (100 mg, 0.505 mmol) and tert-butyl 4-methyl-4-(3-methylpiperazin-1-yl)piperidine-1-carboxylate (420 mg, 1.412 mmol) in carbon tetrachloride (8.00 mL) was heated at 60° C. for 18 h with stirring. After evaporation of solvent, the residue was purified on silica gel to give two diastereomers (3/1 ratio). Yield 180 mg (72%). LC-MS [M+1]=496.4.

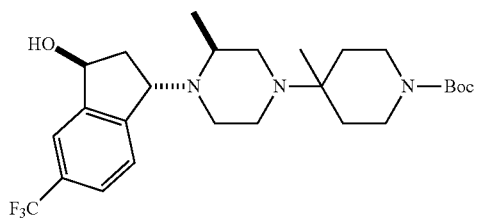 [SMILES: C[C@H]1CN(C2(C)CCN(C(=O)OC(C)(C)C)CC2)CCN1[C@H]1C[C@H](O)c2cc(C(F)(F)F)ccc21]

Step F tert-Butyl 4-{(3S)-4-[3-Hydroxy-5-(trifluoromethyl)-2,3-dihydro-1H-inden-1-yl]-3-methylpiperazin-1-yl}-4-methylpiperidine-1-carboxylate To a solution of tert-butyl 4-methyl-4-{3-methyl-4-[3-oxo-5-(trifluoromethyl)-2,3-dihydro-1H-inden-1-yl]piperazin-1-yl}piperidine-1-carboxylate (100 mg, 0.202 mmol) in ethanol (7 mL) was added sodium borohydride (57 mg, 1.5 mmol). The reaction mixture was stirred at room temperature for 2 h. The solvent was evaporated in vacuo, and the residue was quenched with 10 mL of 1 N aqueous NaOH solution and 10 mL of EtOAc. The organic phase was separated and the aqueous layer was extracted with EtOAc twice (2×15 mL). The combined extracts were washed with brine, dried over $Na_2SO_4$ and evaporated under reduced pressure to give the desired product which was directly used for the next step (93 mg, 92%). LC-MS [M+1]=498.4.

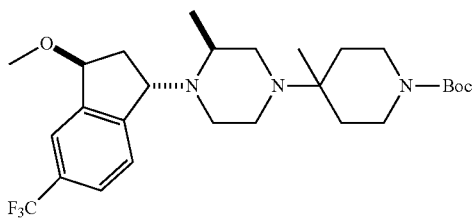

Step G tert-Butyl 4-{(3S)-4-[3-Methoxy-5-(trifluoromethyl)-2,3-dihydro-1H-inden-1-yl]-3-methylpiperazin-1-yl}-4-methylpiperidine-1-carboxylate To a suspension of sodium hydride (150 mg, 3.75 mmol) in tetrahydrofuran (15 mL) was added a solution of tert-butyl 4-{4-[3-hydroxy-5-(trifluoromethyl)-2,3-dihydro-1H-inden-1-yl]-3-methylpiperazin-1-yl}-4-methylpiperidine-1-carboxylate (92 mg, 0.185 mmol) in tetrahydrofuran (5 mL). The reaction mixture was stirred at room temperature for 1 h before methyl iodide (0.50 mL, 8.05 mmol) was added. The reaction was continuously stirred at room temperature overnight and quenched by addition of 10 mL of water and 10 mL of EtOAc. The organic phase was separated and the aqueous layer was extracted with EtOAc twice (2×15 mL). The combined extracts were washed with brine, dried over $Na_2SO_4$, and evaporated under reduced pressure to give the crude product (81 mg, 85%) which was used directly for the next step. LC-MS [M+1]=511.3.

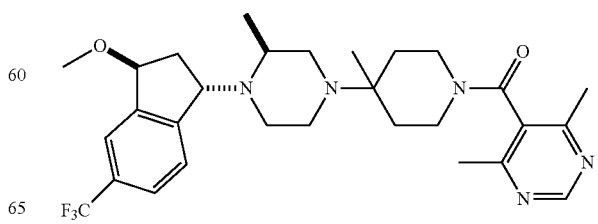

Step H

5-[(4-{(3S)-4-[3-Methoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine tert-Butyl 4-{4-[3-methoxy-5-(trifluoromethyl)-2,3-dihydro-1H-inden-1-yl]-3-methylpiperazin-1-yl}-4-methylpiperidine-1-carboxylate (85 mg, 0.166 mmol) was dissolved in a 4.00 M solution of hydrogen chloride in 1,4-dioxane (2 mL). The mixture was stirred for 1 h and concentrated to dryness and pumped in vacuo.

To a slurry of 4,6-dimethyl-pyrimidine-5-carboxylic acid (50.6 mg, 0.333 mmol) in acetonitrile (4 mL) at 0° C., a drop of DMF (used as catalyst) was added followed by oxalyl chloride (0.028 mL, 0.333 mmol). The resulting slurry was stirred at room temperature for 2 h. To the reaction mixture was added the solution of the above amine hydrochloride in acetonitrile (4 mL) in the presence of triethylamine (0.139 mL, 0.998 mmol) at 0° C. The resulting slurry was heated at 45-50° C. for 6 h and at 80° C. for 3 h. Direct chromatography on silica gel afforded the desired product (71 mg, 78%). LC-MS [M+1]=546.3.

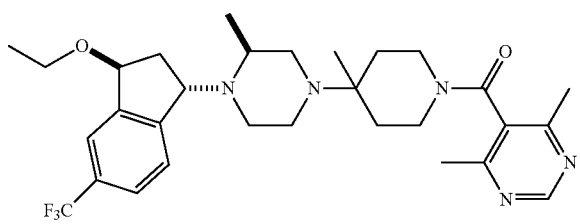 [SMILES: CCO[C@H]1C[C@H](N2CCN(C3(C)CCN(C(=O)c4c(C)ncnc4C)CC3)C[C@@H]2C)c2ccc(C(F)(F)F)cc21]

Example 24

5-[(4-{(3S)-4-[3-Ethoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine The title compound was prepared in a manner analogous to that for Example 23. MS (M+H) 560.2.

Example A

CCR5 Expression

A leukophoresis (Biological Specialty, Colmar, Pa.) was obtained from normal, drug free donors and peripheral blood mononuclear cells (PBMCs) were isolated via density gradient centrifugation. Monocytes were further isolated via centrifugal elutriation. After being washed, the monocytes were re-suspended at $10^6$ cells/ml with RPMI (Invitrogen, Carlsbad, Calif.) supplemented with 10% FBS (Hyclone, Logan, Utah) and 10-20 ng/mL of recombinant human IL-10 (R&D systems, Minneapolis, Minn.) and incubated in the same medium at 37° C. with 5% $CO_2$ for 24-48 hr. CCR5 expression on the IL-10-treated monocytes was then verified by staining the cells with a PE-conjugated anti-human CCR5 antibody ((Pharmingen, San Diego, Calif.), followed by FACS analysis using FACScalibur (BD Biosciences, Bedford, Mass.).

Example B

CCR5 Binding Assay

In a 96 well MultiScreen™ filter plate (Millipore Systems, Billerica, Mass.), $3\times10^5$ IL-10-treated monocytes in 150 μL RPMI (Invitrogen, Carlsbad, Calif.) with 20 mM HEPES (Invitrogen, Carlsbad, Calif.) and 0.3% BSA (Sigma, St Louis, Mo.) were incubated at room temperature for 1 hr. with 0.2 nM $^{125}$I-MIP-1β (Perkin Elmer, Boston, Mass.) and a series concentrations of compound of the invention. Non-specific binding was determined by incubating the cells with 0.3 μM MIP-1β (R&D Systems, Minneapolis, Minn.). The binding reaction was terminated by harvesting the cells onto the filter in the plate on a vacuum manifold (Millipore Systems, Billerica, Mass.). The filter was then washed 5 times with RPMI (Invitrogen, Carlsbad, Calif.) supplemented with 20 mM HEPES (Invitrogen, Carlsbad, Calif.), 0.3% BSA (Sigma, St Louis, Mo.) and 0.4 M NaCl on the vacuum manifold, air dried, and peeled from the plate. The filter dishes corresponding to the sample wells in a filter plate were punched out using the Millipore Punch System (Millipore Systems, Billerica, Mass.). The amount of bound radioactivity on each filter dish was determined by counting on a gamma counter. Specific binding was defined as the total binding minus the non-specific binding. The binding data were evaluated with Prism (GraphPad Software, San Diego, Calif.). Compounds of the invention were found to have a binding affinity of about 1 μM or less according to this assay.

Example C

HIV-1 Entry Assay

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by, for example, Connor et al, *Virology,* 206 (1995), 935-944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

Example D

HIV-1 Replication Assay in MT-4 Cells

Inhibition of HIV-1 NL4.3 (or $III_B$) replication assays can be carried out as previously described (Bridger, et al., *J. Med. Chem.* 42:3971-3981 (1999); De Clercq, et al., *Proc. Natl. Acad. Sci.* 89:5286-5290 (1992); De Clercq, et al., *Antimicrob. Agents Chemother.* 38:668-674 (1994); Bridger, et al. *J. Med. Chem.* 38:366-378 (1995)). To summarize, anti-HIV activity and cytotoxicity measurements are carried out in parallel and are based on the viability of MT-4 cells that are infected with HIV in the presence of various concentrations of the test compounds. After the MT-4 cells are allowed to proliferate for 5 days, the number of viable cells are quantified by a tetrazolium-based calorimetric 3-(4,5-dimethylthiazol-2-yl)-2,5-diphenyltetrazolium bromide (MTT) procedure in 96-well microtrays. Results can be quanitited to yield $EC_{50}$ values which represent the concentration required to protect 50% of the virus-infected cells against viral cytopathicity.

Example E

Chemokine Receptor Inhibition/Binding Assays

The capacity of the compounds of the invention to antagonize chemokine receptor (e.g., CCR2) function can be determined using a suitable screen (e.g., high through-put assay). For example, an agent can be tested in an extracellular acidification assay, calcium flux assay, ligand binding assay or chemotaxis assay (see, for example, Hesselgesser et al., J. Biol. Chem. 273(25):15687-15692 (1998); WO 00/05265 and WO 98/02151, each of which is incorporated herein by reference in its entirety).

In an example assay, a chemokine receptor which can be isolated or recombinantly derived is used which has at least one property, activity or functional characteristic of a mammalian chemokine receptor. The specific property can be a binding property (to, for example, a ligand or inhibitor), a signalling activity (e.g., activation of a mammalian G protein, induction of rapid and transient increase in the concentration of cytosolic free calcium $[Ca^{++}]i$, cellular response function (e.g., stimulation of chemotaxis or inflammatory mediator release by leukocytes), and the like.

In one embodiment, a composition containing a chemokine receptor or variant thereof is maintained under conditions suitable for binding. The receptor is contacted with a compound to be tested, and binding is detected or measured.

In further embodiments, the assay is a cell-based assay in which cells are used that are stably or transiently transfected with a vector or expression cassette having a nucleic acid sequence which encodes the receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation between compounds of the invention and chemokine receptors can be detected directly or indirectly. For example, the compound can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The antagonist activity of test agents can be reported as the inhibitor concentration required for 50% inhibition ($IC_{50}$ values) of specific binding in receptor binding assays using, for example, $^{125}I$-labeled MCP-1, as ligand, and Peripheral Blood Mononuclear Cells (PBMCs) prepared from normal human whole blood via density gradient centrifugation. Specific binding is preferably defined as the total binding (e.g., total cpm on filters) minus the non-specific binding. Non-specific binding is defined as the amount of cpm still detected in the presence of excess unlabeled competitor (e.g., MCP-1).

The human PBMCs described above can be used in a suitable binding assay. For example, 200,000 to 500,000 cells can be incubated with 0.1 to 0.2 nM $^{125}I$-labeled MCP-1, with or without unlabeled competitor (10 nM MCP-1) or various concentrations of compounds to be tested. $^{125}I$-labeled MCP-1, can be prepared by suitable methods or purchased from commercial vendors (Perkin Elmer, Boston Mass.), The binding reactions can be performed in 50 to 250 µl of a binding buffer consisting of 1M HEPES pH 7.2, and 0.1% BSA (bovine serum albumin), for 30 min at room temperature. The binding reactions can be terminated by harvesting the membranes by rapid filtration through glass fiber filters (Perkin Elmer) which can be presoaked in 0.3% polyethyleneimine or Phosphate Buffered Saline (PBS). The filters can be rinsed with approximately 600 µL of binding buffer containing 0.5 M NaCl or PBS, then dried, and the amount of bound radioactivity can be determined by counting on a Gamma Counter (Perkin Elmer).

The capacity of compounds to antagonize chemokine receptor function can also be determined in a leukocyte chemotaxis assay using suitable cells. Suitable cells include, for example, cell lines, recombinant cells or isolated cells which express a chemokine receptor (e.g., CCR2) and undergo chemokine receptor ligand-induced (e.g., MCP-1) chemotaxis. The assay utilizes human peripheral blood mononuclear cells, in a modified Boyden Chamber (Neuro Probe). 500,000 cells in serum free DMEM media (In Vitrogen) are incubated with or without the inhibitors and warmed to 37° C. The chemotaxis chamber (Neuro Probe) is also prewarmed. 400 µL of warmed 10 nM MCP-1 is added to the bottom chamber in all wells expect the negative control which has DMEM added. An 8 micron membrane filter (Neuro Probe) is place on top and the chamber lid is closed. Cells are then added to the holes in the chamber lid which are associated with the chamber wells below the filter membrane. The whole chamber is incubated at 37° C., 5% $CO_2$ for 30 minutes. The cells are then aspirated off, the chamber lid opened, and the filter gently removed. The top of the filter is washed 3 times with PBS and the bottom is left untouched. The filter is air dried and stained with Wright Geimsa stain (Sigma). Filters are counted by microscopy. The negative control wells serve as background and are subtracted from all values. Antagonist potency can be determined by comparing the number of cells that migrate to the bottom chamber in wells which contain antagonist, to the number of cells which migrate to the bottom chamber in MCP-1 control wells.

Compounds of the present invention can be considered active if they have $IC_{50}$ values in the range of about 0.01 to about 500 nM for the above binding assay. In chemotaxis assays, active compounds have $IC_{50}$ values in the range of about 1 to about 3000 nM.

Various modifications of the invention, in addition to those described herein, will be apparent to those skilled in the art from the foregoing description. Such modifications are also intended to fall within the scope of the appended claims. Each reference cited in the present application, including all patents, publications and books, is incorporated herein by reference in its entirety.

What is claimed is:
1. A method of inhibiting activity of a CCR5 comprising contacting CCR5 with a compound of Formula I:

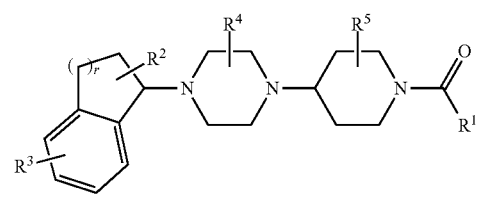

or pharmaceutically acceptable salt thereof, wherein:
$R^1$ is heteroaryl optionally substituted by one or more $R^6$;
$R^2$ is H, halo, cyano, nitro, $C_1$-$C_6$ alkyl, $C_1$-$C_6$ haloalkyl, $C_2$-$C_6$ alkenyl, $C_2$-$C_6$ alkynyl, aryl, heteroaryl, $C_3$-$C_7$ cycloalkyl, heterocycloalkyl, $SOR^7$, $SO_2R^7$, $COR^8$, $OR^9$, $SR^9$, $COOR^9$, $NR^{10}R^{11}$ or $NR^{10}COR^8$;
$R^3$ is F, Cl, Br, I, $C_1$-$C_4$ haloalkyl, $C_1C_4$ haloalkoxy or heteroaryl;
$R^4$ is H, $C_1$-$C_6$ alkyl, $C_2$-$C_6$ alkenyl, $C_2$-$C_6$ alkynyl or $C_1$-$C_6$ haloalkyl;
$R^5$ is H, $C_1$-$C_6$ alkyl, $C_2$-$C_6$ alkenyl, $C_2$-$C_6$ alkynyl or $C_1$-$C_6$ haloalkyl;
$R^6$ is H, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, amino, ($C_1$-$C_6$ alkyl)amino or di($C_1$-$C_6$ alkyl)amino;
$R^7$ is H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl, ($C_3$-$C_7$ cycloalkyl)alkyl, heterocycloalkylalkyl, or $NR^{12}R^{13}$;
$R^8$ is H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl, ($C_3$-$C_7$ cycloalkyl)alkyl, heterocycloalkylalkyl, or $NR^{12}R^{13}$;
$R^9$ is H, $C_1$-$C_6$ alkyl, $C_2$-$C_6$ alkenyl, $C_2$-$C_6$ alkynyl, $C_1$-$C_6$ haloalkyl, alkoxyalkyl, haloalkoxyalkyl, aryloxyalkyl, heteroaryloxyalkyl, cycloalkyloxyalkyl, hetero cycloalkyloxyalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;
$R^{10}$ and $R^{11}$ are each, independently, H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;
or $R^{10}$ and $R^{11}$ together with the N atom to which they are attached form a 3-, 4-, 5-, 6-, or 7-membered heterocycloalkyl group;
$R^{12}$ and $R^{13}$ are each, independently, H, $C_1$-$C_6$ alkyl, $C_2$-$C_6$ alkenyl, $C_2$-$C_6$ alkynyl, $C_1$-$C_6$ haloalkyl, aryl, heteroaryl, $C_3$-$C_7$ cycloalkyl, heterocycloalkyl, arylalkyl, heteroarylalkyl; ($C_3$-$C_7$ cycloalkyl)alkyl or heterocycloalkylalkyl;
or $R^{12}$ and $R^{13}$ together with the N atom to which they are attached form a 3-, 4-, 5-, 6-, or 7-membered heterocycloalkyl group;
r is 1, 2 or 3.

2. The method of claim 1, wherein the compound is 5-[(4-{(3S)-4-[(1R,2R)-2-ethoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine, or a pharmaceutically acceptable salt thereof

3. The method of claim 1, wherein the compound is 5-[(4-{(3S)-4-[(1R,2R)-2-ethoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine dihydrochloride.

4. The method of claim 1, wherein the compound is 5-[(4-{(3S)-4-[(1R,2R)-2-ethoxy-5-(1,3-thiazol-2-yl)-2,3-dihydro-1H-inden-1-yl]-3-methylpiperazin-1-yl}-4-methylpiperidin-1-yl)carbonyl]-4,6-dimethylpyrimidine, or a pharmaceutically acceptable salt thereof.

5. The method of claim 1, wherein the compound is 5-[(4-{4-[2-ethoxy-5-(trifluoromethyl)-2,3-dihydro-1H-inden-1-yl]-3-methylpiperazin-1-yl}-4-methylpiperidin-1-yl)carbonyl]-4,6-dimethylpyrimidine, or a pharmaceutically acceptable salt thereof.

6. The method of claim 1, wherein the compound is 5-[(4-{4-[2-ethoxy-5-(trifluoromethyl)-2,3-dihydro-1H-inden-1-yl]-3-methylpiperazin-1-yl}-4-methylpiperidin-1-yl) carbonyl]-4,6-dimethylpyrimidine dihydrochloride.

7. The method of claim 1, wherein the compound is 5-[(4-{4[2-ethoxy-5-(1,3-thiazol-2-yl)-2,3-dihydro-1H-inden-1-yl]-3-methylpiperazin-1-yl}-4-methylp ip eridin-1-yl)carbonyl]-4,6-dimethylpyrimidine, or a pharmaceutically acceptable salt thereof.

\* \* \* \* \*

UNITED STATES PATENT AND TRADEMARK OFFICE
CERTIFICATE OF CORRECTION

PATENT NO. : 9,067,921 B2
APPLICATION NO. : 14/176781
DATED : June 30, 2015
INVENTOR(S) : Chu-Biao Xue et al.

Page 1 of 1

It is certified that error appears in the above-identified patent and that said Letters Patent is hereby corrected as shown below:

Claims

Col. 72, line 55, in Claim 1, delete "CCR5" and insert -- said CCR5 --

Col. 73, line 6, in Claim 1, delete "$NR^{10}COR^8$;" and insert -- $NR^{10}COR^8$; --

Col. 73, line 7, in Claim 1, delete "$C_1C_4$" and insert -- $C_1$-$C_4$ --

Col. 73, line 19, in Claim 1, delete "heterocycloalkylalkyl,or" and insert -- heterocycloalkylalkyl, or --

Col. 73, lines 26-27, in Claim 1, delete "hetero cycloalkyloxyalkyl," and insert
-- heterocycloalkyloxyalkyl, --

Col. 73, line 30, in Claim 1, delete "$R^{10}$" and insert -- $R^{10}$ --

Col. 73, line 35, in Claim 1, delete "$R^{10}$" and insert -- $R^{10}$ --

Col. 74, line 13, in Claim 2, delete "thereof" and insert -- thereof. --

Col. 74, lines 31-32, in Claim 6, delete "yl) carbonyl]" and insert -- yl)carbonyl] --

Col. 74, lines 34-35, in Claim 7, delete "5-[(4-{4[2-ethoxy" and insert -- 5-[(4-{4-[2-ethoxy --

Col. 74, line 36, in Claim 7, delete "methylp ip eridin" and insert -- methylpiperidin --

Signed and Sealed this
Nineteenth Day of January, 2016

Michelle K. Lee
*Director of the United States Patent and Trademark Office*